(12) United States Patent
Schmitz et al.

(10) Patent No.: US 9,351,741 B2
(45) Date of Patent: May 31, 2016

(54) FLEXIBLE TISSUE REMOVAL DEVICES AND METHODS

(71) Applicant: Amendia, Inc., Marietta, GA (US)

(72) Inventors: Gregory P. Schmitz, Los Gatos, CA (US); Jeffery L. Bleich, Palo Alto, CA (US); Steven A. Spisak, San Jose, CA (US); Roy Leguidleguid, Union City, CA (US); Jefferey Bleam, Boulder Creek, CA (US)

(73) Assignee: Amendia, Inc., Marietta, GA (US)

( * ) Notice: Subject to any disclaimer, the term of this patent is extended or adjusted under 35 U.S.C. 154(b) by 358 days.

(21) Appl. No.: 14/082,052

(22) Filed: Nov. 15, 2013

(65) Prior Publication Data

US 2014/0074097 A1 Mar. 13, 2014

Related U.S. Application Data

(63) Continuation of application No. 13/267,683, filed on Oct. 6, 2011, now Pat. No. 8,585,704, which is a continuation of application No. 11/687,558, filed on Mar. 16, 2007, now Pat. No. 8,062,298, which is a (Continued)

(51) Int. Cl.
*A61B 17/16* (2006.01)
*A61B 17/00* (2006.01)
(Continued)

(52) U.S. Cl.
CPC ....... *A61B 17/1671* (2013.01); *A61B 17/00234* (2013.01); *A61B 17/14* (2013.01); *A61B 17/1659* (2013.01); *A61B 17/1757* (2013.01); *A61B 17/32* (2013.01);

(Continued)

(58) Field of Classification Search
CPC .................. A61B 17/1659; A61B 17/1671
See application file for complete search history.

(56) References Cited

U.S. PATENT DOCUMENTS

| 184,804 A | 11/1876 | Stohlmann |
|---|---|---|
| 289,104 A | 11/1883 | How |

(Continued)

FOREIGN PATENT DOCUMENTS

| CN | 1338911 | 3/2002 |
|---|---|---|
| CN | 101291633 | 10/2008 |

(Continued)

OTHER PUBLICATIONS

Bleich et al.; U.S. Appl. No. 14/180,221 entitled "Flexible tissue rasp," filed Feb. 13, 2014.

(Continued)

*Primary Examiner* — David Bates
(74) *Attorney, Agent, or Firm* — David L. King

(57) ABSTRACT

A device for removing tissue from a patient may include an elongate flexible body having a proximal end, a distal end, and a longitudinal axis therebetween, the elongate body having opposed first and second major surfaces with a lateral orientation across the axis, and a plurality of blades distributed laterally across the first major surface. Each blade may have a first end adjacent the first surface and extending to a cantilevered second end, a first edge between the first and second ends of the blade being oriented toward the distal end of the elongate body, a second edge between the first and second ends of the blade being oriented toward the proximal end of the elongate body, a height of the blade between its first and second ends, and an axial length of the blade between its first and second edges.

22 Claims, 25 Drawing Sheets

Related U.S. Application Data continuation-in-part of application No. 11/429,377, filed on May 4, 2006, now Pat. No. 8,048,080.

(60) Provisional application No. 60/869,070, filed on Dec. 7, 2006.

(51) Int. Cl.
  *A61B 17/14* (2006.01)
  *A61B 17/17* (2006.01)
  *A61B 17/32* (2006.01)
  *A61B 17/34* (2006.01)
  *A61B 17/02* (2006.01)

(52) U.S. Cl.
  CPC ............ *A61B 17/3421* (2013.01); *A61B 17/02* (2013.01); *A61B 17/32002* (2013.01); *A61B 17/320016* (2013.01); *A61B 2017/00261* (2013.01); *A61B 2017/00867* (2013.01); *A61B 2017/143* (2013.01); *A61B 2017/145* (2013.01); *A61B 2017/320004* (2013.01); *A61B 2017/32006* (2013.01); *A61B 2017/3488* (2013.01)

(56) References Cited

U.S. PATENT DOCUMENTS

| | | |
|---|---|---|
| 863,389 A | 8/1907 | Harkin |
| 1,039,487 A | 9/1912 | Casebolt |
| 1,201,467 A | 10/1916 | Hoglund |
| 1,374,638 A | 4/1921 | De Cew et al. |
| 1,543,195 A | 6/1925 | Thygesen |
| 1,690,812 A | 11/1928 | Bertels |
| 1,938,200 A | 12/1933 | Wells |
| 2,243,757 A | 5/1941 | Kohls et al. |
| 2,269,749 A | 1/1942 | Wilkie |
| 2,372,553 A | 3/1945 | Coddington |
| 2,437,697 A | 3/1948 | Kalom |
| 2,516,882 A | 8/1950 | Kalom |
| 2,704,064 A | 5/1955 | Fizzell |
| 2,820,281 A | 1/1958 | Amsen |
| 2,843,128 A | 7/1958 | Storz |
| 2,982,005 A | 5/1961 | Booth |
| 3,124,824 A | 3/1964 | Lutz |
| RE25,582 E | 5/1964 | Davies |
| 3,150,470 A | 9/1964 | Barron |
| 3,200,814 A | 8/1965 | Taylor et al. |
| 3,214,824 A | 11/1965 | Brown |
| 3,389,447 A | 6/1968 | Theobald et al. |
| 3,491,776 A | 1/1970 | Fleming |
| 3,495,590 A | 2/1970 | Zeiller |
| 3,528,152 A | 9/1970 | Funakubo et al. |
| 3,624,484 A | 11/1971 | Colyer |
| 3,640,280 A | 2/1972 | Slanker et al. |
| 3,651,844 A | 3/1972 | Barnes |
| 3,664,329 A | 5/1972 | Naylor |
| 3,682,162 A | 8/1972 | Colyer |
| 3,699,729 A | 10/1972 | Garvey et al. |
| 3,752,166 A | 8/1973 | Lyon et al. |
| 3,774,355 A | 11/1973 | Dawson et al. |
| 3,830,226 A | 8/1974 | Staub et al. |
| 3,835,859 A | 9/1974 | Roberts et al. |
| 3,956,858 A | 5/1976 | Catlin et al. |
| 3,957,036 A | 5/1976 | Normann |
| 3,978,862 A | 9/1976 | Morrison |
| 3,999,294 A | 12/1976 | Shoben |
| 4,015,931 A | 4/1977 | Thakur |
| 4,099,519 A | 7/1978 | Warren |
| 4,108,182 A | 8/1978 | Hartman et al. |
| 4,160,320 A | 7/1979 | Wikoff |
| 4,172,440 A | 10/1979 | Schneider et al. |
| 4,203,444 A | 5/1980 | Bonnell et al. |
| 4,207,897 A | 6/1980 | Lloyd et al. |
| 4,259,276 A | 3/1981 | Rawlings |
| 4,405,061 A | 9/1983 | Bergandy |
| D273,806 S | 5/1984 | Bolesky et al. |
| 4,464,836 A | 8/1984 | Hissa |
| 4,502,184 A | 3/1985 | Karubian |
| 4,515,168 A | 5/1985 | Chester et al. |
| 4,518,022 A | 5/1985 | Valdes et al. |
| 4,545,374 A | 10/1985 | Jacobson |
| 4,573,448 A | 3/1986 | Kambin |
| 4,580,545 A | 4/1986 | Dorsten |
| 4,590,949 A | 5/1986 | Pohndorf |
| 4,616,660 A | 10/1986 | Johns |
| 4,621,636 A | 11/1986 | Fogarty |
| 4,625,725 A | 12/1986 | Davison et al. |
| 4,660,571 A | 4/1987 | Hess et al. |
| 4,678,459 A | 7/1987 | Onik et al. |
| 4,690,642 A | 9/1987 | Kyotani |
| 4,700,702 A | 10/1987 | Nilsson |
| 4,709,699 A | 12/1987 | Michael et al. |
| 4,741,343 A | 5/1988 | Bowman |
| 4,750,249 A | 6/1988 | Richardson |
| 4,794,931 A | 1/1989 | Yock |
| 4,808,157 A | 2/1989 | Coombs |
| 4,817,628 A | 4/1989 | Zealear et al. |
| 4,856,193 A | 8/1989 | Grachan |
| 4,867,155 A | 9/1989 | Isaacson |
| 4,872,452 A | 10/1989 | Alexson |
| 4,873,978 A | 10/1989 | Ginsburg |
| 4,883,460 A | 11/1989 | Zanetti |
| 4,894,063 A | 1/1990 | Nashe |
| 4,912,799 A | 4/1990 | Coleman, Jr. |
| RE33,258 E | 7/1990 | Onik et al. |
| 4,943,295 A | 7/1990 | Hartlaub et al. |
| 4,946,462 A | 8/1990 | Watanabe |
| 4,957,117 A | 9/1990 | Wysham |
| 4,962,766 A | 10/1990 | Herzon |
| 4,973,329 A | 11/1990 | Park et al. |
| 4,990,148 A | 2/1991 | Worrick, III et al. |
| 4,994,036 A | 2/1991 | Biscoping et al. |
| 4,994,072 A | 2/1991 | Bhate et al. |
| 4,995,200 A | 2/1991 | Eberhart |
| 5,019,082 A | 5/1991 | Frey et al. |
| 5,025,787 A | 6/1991 | Sutherland et al. |
| 5,026,379 A | 6/1991 | Yoon |
| 5,026,386 A | 6/1991 | Michelson |
| 5,078,137 A | 1/1992 | Edell et al. |
| 5,089,003 A | 2/1992 | Fallin et al. |
| 5,100,424 A | 3/1992 | Jang et al. |
| 5,108,403 A | 4/1992 | Stern |
| 5,123,400 A | 6/1992 | Edgerton |
| 5,125,928 A | 6/1992 | Parins et al. |
| 5,147,364 A | 9/1992 | Comparetto |
| 5,152,749 A | 10/1992 | Giesy et al. |
| 5,161,534 A | 11/1992 | Berthiaume |
| 5,163,939 A | 11/1992 | Winston |
| 5,176,649 A | 1/1993 | Wakabayashi |
| 5,178,145 A | 1/1993 | Rea |
| 5,178,161 A | 1/1993 | Kovacs |
| 5,191,888 A | 3/1993 | Palmer et al. |
| 5,195,507 A | 3/1993 | Bilweis |
| 5,201,704 A | 4/1993 | Ray |
| 5,215,105 A | 6/1993 | Kizelshteyn et al. |
| 5,219,358 A | 6/1993 | Bendel et al. |
| 5,234,435 A | 8/1993 | Seagrave, Jr. |
| 5,242,418 A | 9/1993 | Weinstein |
| 5,250,035 A | 10/1993 | Smith et al. |
| 5,255,691 A | 10/1993 | Otten |
| 5,271,415 A | 12/1993 | Foerster et al. |
| 5,281,218 A | 1/1994 | Imran |
| 5,284,153 A | 2/1994 | Raymond et al. |
| 5,284,154 A | 2/1994 | Raymond et al. |
| 5,300,077 A | 4/1994 | Howell |
| 5,325,868 A | 7/1994 | Kimmelstiel |
| 5,341,807 A | 8/1994 | Nardella |
| 5,351,679 A | 10/1994 | Mayzels et al. |
| 5,353,784 A | 10/1994 | Nady-Mohamed |
| 5,353,789 A | 10/1994 | Schlobohm |
| 5,353,802 A | 10/1994 | Ollmar |
| 5,360,441 A | 11/1994 | Otten |
| 5,365,928 A | 11/1994 | Rhinehart et al. |

(56) References Cited

U.S. PATENT DOCUMENTS

| | | |
|---|---|---|
| 5,374,261 A | 12/1994 | Yoon |
| 5,383,879 A | 1/1995 | Phillips |
| 5,385,146 A | 1/1995 | Goldreyer |
| 5,387,218 A | 2/1995 | Meswania |
| 5,396,880 A | 3/1995 | Kagan et al. |
| 5,421,348 A | 6/1995 | Larnard |
| 5,423,331 A | 6/1995 | Wysham |
| 5,437,661 A | 8/1995 | Rieser |
| 5,439,464 A | 8/1995 | Shapiro |
| 5,441,044 A | 8/1995 | Tovey et al. |
| 5,441,510 A | 8/1995 | Simpson et al. |
| 5,454,815 A | 10/1995 | Geisser et al. |
| 5,456,254 A | 10/1995 | Pietroski et al. |
| 5,496,325 A | 3/1996 | McLees |
| 5,512,037 A | 4/1996 | Russell et al. |
| 5,515,848 A | 5/1996 | Corbett, III et al. |
| 5,531,749 A | 7/1996 | Michelson |
| 5,534,009 A | 7/1996 | Lander |
| 5,546,958 A | 8/1996 | Thorud et al. |
| 5,554,110 A | 9/1996 | Edwards et al. |
| 5,555,892 A | 9/1996 | Tipton |
| 5,560,372 A | 10/1996 | Cory |
| 5,562,695 A | 10/1996 | Obenchain |
| 5,571,181 A | 11/1996 | Li |
| 5,582,618 A | 12/1996 | Chin et al. |
| 5,591,170 A | 1/1997 | Spievack et al. |
| 5,598,848 A | 2/1997 | Swanson et al. |
| 5,620,447 A | 4/1997 | Smith et al. |
| 5,630,426 A | 5/1997 | Eggers et al. |
| 5,634,475 A | 6/1997 | Wolvek |
| 5,643,304 A | 7/1997 | Schechter et al. |
| 5,651,373 A | 7/1997 | Mah |
| 5,656,012 A | 8/1997 | Sienkiewicz |
| 5,680,860 A | 10/1997 | Imran |
| 5,681,324 A | 10/1997 | Kammerer et al. |
| 5,697,889 A | 12/1997 | Slotman et al. |
| 5,709,697 A | 1/1998 | Ratcliff et al. |
| 5,725,530 A | 3/1998 | Popken |
| 5,735,792 A | 4/1998 | Vanden Hoek et al. |
| 5,755,732 A | 5/1998 | Green et al. |
| 5,759,159 A | 6/1998 | Masreliez |
| 5,762,629 A | 6/1998 | Kambin |
| 5,766,168 A | 6/1998 | Mantell |
| 5,769,865 A | 6/1998 | Kermode et al. |
| 5,775,331 A | 7/1998 | Raymond et al. |
| 5,779,642 A | 7/1998 | Nightengale |
| 5,788,653 A | 8/1998 | Lorenzo |
| 5,792,044 A | 8/1998 | Foley et al. |
| 5,795,308 A | 8/1998 | Russin |
| 5,800,350 A | 9/1998 | Coppleson et al. |
| 5,803,902 A | 9/1998 | Sienkiewicz et al. |
| 5,803,904 A | 9/1998 | Mehdizadeh |
| 5,807,263 A | 9/1998 | Chance |
| 5,810,744 A | 9/1998 | Chu et al. |
| 5,813,405 A | 9/1998 | Montano, Jr. et al. |
| 5,824,040 A | 10/1998 | Cox et al. |
| 5,830,151 A | 11/1998 | Hadzic et al. |
| 5,830,157 A | 11/1998 | Foote |
| 5,830,188 A | 11/1998 | Abouleish |
| 5,833,692 A | 11/1998 | Cesarini et al. |
| 5,836,810 A | 11/1998 | Åsum |
| 5,836,948 A | 11/1998 | Zucherman et al. |
| 5,843,110 A | 12/1998 | Dross et al. |
| 5,846,196 A | 12/1998 | Siekmeyer et al. |
| 5,846,244 A | 12/1998 | Cripe |
| 5,851,191 A | 12/1998 | Gozani |
| 5,851,209 A | 12/1998 | Kummer et al. |
| 5,851,214 A | 12/1998 | Larsen et al. |
| 5,853,373 A | 12/1998 | Griffith et al. |
| 5,865,844 A | 2/1999 | Plaia et al. |
| 5,868,767 A | 2/1999 | Farley et al. |
| 5,879,353 A | 3/1999 | Terry |
| 5,885,219 A | 3/1999 | Nightengale |
| 5,895,417 A | 4/1999 | Pomeranz et al. |
| 5,897,583 A | 4/1999 | Meyer et al. |
| 5,899,909 A | 5/1999 | Claren et al. |
| 5,904,657 A | 5/1999 | Unsworth et al. |
| 5,916,173 A | 6/1999 | Kirsner |
| 5,918,604 A | 7/1999 | Whelan |
| 5,919,190 A | 7/1999 | VanDusseldorp |
| 5,928,158 A | 7/1999 | Aristides |
| 5,941,822 A | 8/1999 | Skladnev et al. |
| 5,961,522 A | 10/1999 | Mehdizadeh |
| 5,972,013 A | 10/1999 | Schmidt |
| 5,976,110 A | 11/1999 | Greengrass et al. |
| 5,976,146 A | 11/1999 | Ogawa et al. |
| 6,002,964 A | 12/1999 | Feler et al. |
| 6,004,326 A | 12/1999 | Castro et al. |
| 6,004,330 A | 12/1999 | Middleman et al. |
| 6,010,493 A | 1/2000 | Snoke |
| 6,015,406 A | 1/2000 | Goble et al. |
| 6,022,362 A | 2/2000 | Lee et al. |
| 6,030,383 A | 2/2000 | Benderev |
| 6,030,401 A | 2/2000 | Marino |
| 6,038,480 A | 3/2000 | Hrdlicka et al. |
| 6,048,345 A | 4/2000 | Berke et al. |
| 6,068,642 A | 5/2000 | Johnson et al. |
| 6,073,051 A | 6/2000 | Sharkey et al. |
| 6,099,514 A | 8/2000 | Sharkey et al. |
| 6,102,930 A | 8/2000 | Simmons, Jr. |
| 6,106,558 A | 8/2000 | Picha |
| 6,113,534 A | 9/2000 | Koros et al. |
| D432,384 S | 10/2000 | Simons |
| 6,132,387 A | 10/2000 | Gozani et al. |
| 6,136,014 A | 10/2000 | Sirimanne et al. |
| 6,142,993 A | 11/2000 | Whayne et al. |
| 6,142,994 A | 11/2000 | Swanson et al. |
| 6,146,380 A | 11/2000 | Racz et al. |
| 6,152,894 A | 11/2000 | Kubler |
| 6,169,916 B1 | 1/2001 | West |
| 6,205,360 B1 | 3/2001 | Carter et al. |
| 6,214,001 B1 | 4/2001 | Casscells et al. |
| 6,214,016 B1 | 4/2001 | Williams et al. |
| 6,236,892 B1 | 5/2001 | Feler |
| 6,251,115 B1 | 6/2001 | Williams et al. |
| 6,256,540 B1 | 7/2001 | Panescu et al. |
| 6,259,945 B1 | 7/2001 | Epstein et al. |
| 6,261,582 B1 | 7/2001 | Needham et al. |
| 6,266,551 B1 | 7/2001 | Osadchy et al. |
| 6,266,558 B1 | 7/2001 | Gozani et al. |
| 6,267,760 B1 | 7/2001 | Swanson |
| 6,272,367 B1 | 8/2001 | Chance |
| 6,277,094 B1 | 8/2001 | Schendel |
| 6,280,447 B1 | 8/2001 | Marino et al. |
| 6,292,702 B1 | 9/2001 | King et al. |
| 6,298,256 B1 | 10/2001 | Meyer |
| 6,312,392 B1 | 11/2001 | Herzon |
| 6,324,418 B1 | 11/2001 | Crowley et al. |
| 6,324,432 B1 | 11/2001 | Rigaux et al. |
| 6,325,764 B1 | 12/2001 | Griffith et al. |
| 6,334,068 B1 | 12/2001 | Hacker |
| 6,343,226 B1 | 1/2002 | Sunde et al. |
| 6,358,254 B1 | 3/2002 | Anderson |
| 6,360,750 B1 | 3/2002 | Gerber et al. |
| 6,364,886 B1 | 4/2002 | Sklar |
| 6,368,324 B1 | 4/2002 | Dinger et al. |
| 6,370,411 B1 | 4/2002 | Osadchy et al. |
| 6,370,435 B2 | 4/2002 | Panescu et al. |
| 6,383,509 B1 | 5/2002 | Donovan et al. |
| 6,390,906 B1 | 5/2002 | Subramanian |
| 6,391,028 B1 | 5/2002 | Fanton et al. |
| 6,416,505 B1 | 7/2002 | Fleischman et al. |
| 6,423,071 B1 | 7/2002 | Lawson |
| 6,423,080 B1 | 7/2002 | Gellman et al. |
| 6,425,887 B1 | 7/2002 | McGuckin et al. |
| 6,436,101 B1 | 8/2002 | Hamada |
| 6,442,848 B1 | 9/2002 | Dean |
| 6,446,621 B1 | 9/2002 | Svensson |
| 6,451,335 B1 | 9/2002 | Goldenheim et al. |
| 6,454,767 B2 | 9/2002 | Alleyne |
| 6,464,682 B1 | 10/2002 | Snoke |
| 6,466,817 B1 | 10/2002 | Kaula et al. |
| 6,468,289 B1 | 10/2002 | Bonutti |
| 6,470,209 B2 | 10/2002 | Snoke |

(56) References Cited

U.S. PATENT DOCUMENTS

| | | | |
|---|---|---|---|
| 6,478,805 B1 | 11/2002 | Marino et al. | |
| 6,487,439 B1 | 11/2002 | Skladnev et al. | |
| 6,488,636 B2 | 12/2002 | Bryan et al. | |
| 6,491,646 B1 | 12/2002 | Blackledge | |
| 6,500,128 B2 | 12/2002 | Marino | |
| 6,500,189 B1 | 12/2002 | Lang et al. | |
| 6,512,958 B1 | 1/2003 | Swoyer et al. | |
| 6,516,223 B2 | 2/2003 | Hofmann | |
| 6,527,786 B1 | 3/2003 | Davis et al. | |
| 6,533,749 B1 | 3/2003 | Mitusina et al. | |
| 6,535,759 B1 | 3/2003 | Epstein et al. | |
| 6,540,742 B1 | 4/2003 | Thomas et al. | |
| 6,540,761 B2 | 4/2003 | Houser | |
| 6,546,270 B1 | 4/2003 | Goldin et al. | |
| 6,558,353 B2 | 5/2003 | Zohmann | |
| 6,562,033 B2 | 5/2003 | Shah et al. | |
| 6,564,078 B1 | 5/2003 | Marino et al. | |
| 6,564,079 B1 | 5/2003 | Cory et al. | |
| 6,564,088 B1 | 5/2003 | Soller et al. | |
| 6,569,160 B1 | 5/2003 | Goldin et al. | |
| 6,575,979 B1 | 6/2003 | Cragg | |
| 6,579,291 B1 | 6/2003 | Keith et al. | |
| 6,584,345 B2 | 6/2003 | Govari | |
| 6,592,559 B1 | 7/2003 | Pakter et al. | |
| 6,595,932 B2 | 7/2003 | Ferrera | |
| 6,597,955 B2 | 7/2003 | Panescu et al. | |
| 6,606,523 B1 | 8/2003 | Jenkins | |
| 6,607,530 B1 | 8/2003 | Carl et al. | |
| 6,609,018 B2 | 8/2003 | Cory et al. | |
| 6,610,066 B2 | 8/2003 | Dinger et al. | |
| 6,620,129 B2 | 9/2003 | Stecker et al. | |
| 6,622,731 B2 | 9/2003 | Daniel et al. | |
| 6,624,510 B1 | 9/2003 | Chan et al. | |
| 6,626,916 B1 | 9/2003 | Yeung et al. | |
| 6,632,184 B1 | 10/2003 | Truwit | |
| 6,638,233 B2 | 10/2003 | Corvi et al. | |
| RE38,335 E | 11/2003 | Aust et al. | |
| 6,648,883 B2 | 11/2003 | Francischelli et al. | |
| 6,666,874 B2 | 12/2003 | Heitzmann et al. | |
| 6,673,063 B2 | 1/2004 | Brett | |
| 6,673,068 B1 | 1/2004 | Berube | |
| 6,678,552 B2 | 1/2004 | Pearlman | |
| 6,682,535 B2 | 1/2004 | Hoogland | |
| 6,682,536 B2 | 1/2004 | Vardi et al. | |
| 6,699,246 B2 | 3/2004 | Zucherman et al. | |
| 6,723,049 B2 | 4/2004 | Skladnev et al. | |
| 6,726,531 B1 | 4/2004 | Harrel | |
| 6,726,685 B2 | 4/2004 | To et al. | |
| 6,733,496 B2 | 5/2004 | Sharkey et al. | |
| 6,736,835 B2 | 5/2004 | Pellegrino et al. | |
| 6,746,451 B2 | 6/2004 | Middleton et al. | |
| 6,752,814 B2 | 6/2004 | Gellman et al. | |
| 6,760,616 B2 | 7/2004 | Hoey et al. | |
| 6,772,012 B2 | 8/2004 | Ricart et al. | |
| 6,776,765 B2 | 8/2004 | Soukup et al. | |
| 6,788,966 B2 | 9/2004 | Kenan et al. | |
| 6,790,210 B1 | 9/2004 | Cragg et al. | |
| 6,805,695 B2 | 10/2004 | Keith et al. | |
| 6,805,697 B1 | 10/2004 | Helm et al. | |
| 6,807,444 B2 | 10/2004 | Tu et al. | |
| 6,830,561 B2 | 12/2004 | Jansen et al. | |
| 6,830,570 B1 | 12/2004 | Frey et al. | |
| 6,832,111 B2 | 12/2004 | Tu et al. | |
| 6,845,264 B1 | 1/2005 | Skladnev et al. | |
| 6,847,849 B2 | 1/2005 | Mamo et al. | |
| 6,851,430 B2 | 2/2005 | Tsou | |
| 6,865,409 B2 | 3/2005 | Getsla et al. | |
| 6,872,204 B2 | 3/2005 | Houser | |
| 6,875,221 B2 | 4/2005 | Cull | |
| 6,882,879 B2 | 4/2005 | Rock | |
| 6,884,220 B2 | 4/2005 | Aviv et al. | |
| 6,890,353 B2 | 5/2005 | Cohn et al. | |
| 6,899,716 B2 | 5/2005 | Cragg | |
| 6,907,884 B2 | 6/2005 | Pellegrino et al. | |
| 6,911,003 B2 | 6/2005 | Anderson et al. | |
| 6,911,016 B2 | 6/2005 | Balzum et al. | |
| 6,916,328 B2 | 7/2005 | Brett | |
| 6,923,813 B2 | 8/2005 | Phillips et al. | |
| 6,929,647 B2 | 8/2005 | Cohen | |
| 6,949,104 B2 | 9/2005 | Griffis et al. | |
| 6,953,461 B2 | 10/2005 | McClurken et al. | |
| 6,962,587 B2 | 11/2005 | Johnson et al. | |
| 6,971,986 B2 | 12/2005 | Staskin et al. | |
| 6,972,199 B2 | 12/2005 | Lebouitz et al. | |
| 6,973,342 B1 | 12/2005 | Swanson | |
| 6,976,986 B2 | 12/2005 | Berube | |
| 6,991,643 B2 | 1/2006 | Saadat | |
| 6,994,693 B2 | 2/2006 | Tal | |
| 6,997,934 B2 | 2/2006 | Snow et al. | |
| 6,999,820 B2 | 2/2006 | Jordan | |
| 7,001,333 B2 | 2/2006 | Hamel et al. | |
| 7,008,431 B2 | 3/2006 | Simonson | |
| 7,010,352 B2 | 3/2006 | Hogan | |
| 7,011,635 B1 | 3/2006 | Delay | |
| 7,011,663 B2 | 3/2006 | Michelson | |
| 7,014,616 B2 | 3/2006 | Ferrera | |
| 7,033,373 B2 | 4/2006 | de la Torre et al. | |
| 7,041,099 B2 | 5/2006 | Thomas et al. | |
| 7,047,084 B2 | 5/2006 | Erickson et al. | |
| 7,048,682 B2 | 5/2006 | Neisz et al. | |
| 7,050,848 B2 | 5/2006 | Hoey et al. | |
| 7,063,682 B1 | 6/2006 | Whayne et al. | |
| 7,070,556 B2 | 7/2006 | Anderson et al. | |
| 7,070,596 B1 | 7/2006 | Woloszko et al. | |
| 7,079,883 B2 | 7/2006 | Marino et al. | |
| 7,081,122 B1 | 7/2006 | Reiley et al. | |
| 7,087,053 B2 | 8/2006 | Vanney | |
| 7,087,058 B2 | 8/2006 | Cragg | |
| 7,107,104 B2 | 9/2006 | Keravel et al. | |
| 7,118,576 B2 | 10/2006 | Gitis et al. | |
| 7,141,019 B2 | 11/2006 | Pearlman | |
| 7,166,073 B2 | 1/2007 | Ritland | |
| 7,166,081 B2 | 1/2007 | McKinley | |
| 7,166,107 B2 | 1/2007 | Anderson | |
| 7,169,107 B2 | 1/2007 | Jersey-Willuhn et al. | |
| 7,169,147 B2 | 1/2007 | Nosel | |
| 7,189,240 B1 * | 3/2007 | Dekel | A61B 17/14 606/84 |
| 7,198,598 B2 | 4/2007 | Smith et al. | |
| 7,198,626 B2 | 4/2007 | Lee et al. | |
| 7,207,949 B2 | 4/2007 | Miles et al. | |
| 7,211,082 B2 | 5/2007 | Hall et al | |
| 7,214,186 B2 | 5/2007 | Ritland | |
| 7,214,197 B2 | 5/2007 | Prass | |
| 7,216,001 B2 | 5/2007 | Hacker et al. | |
| 7,223,278 B2 | 5/2007 | Davison et al. | |
| 7,236,832 B2 | 6/2007 | Hemmerling et al. | |
| 7,239,911 B2 | 7/2007 | Scholz | |
| 7,270,658 B2 | 9/2007 | Woloszko et al. | |
| 7,282,061 B2 | 10/2007 | Sharkey et al. | |
| 7,337,005 B2 | 2/2008 | Kim et al. | |
| 7,337,006 B2 | 2/2008 | Kim et al. | |
| 7,470,236 B1 | 12/2008 | Kelleher et al. | |
| 7,494,473 B2 | 2/2009 | Eggers et al. | |
| 7,503,920 B2 | 3/2009 | Siegal | |
| 7,507,218 B2 | 3/2009 | Aliski et al. | |
| 7,553,307 B2 | 6/2009 | Bleich et al. | |
| 7,555,343 B2 | 6/2009 | Bleich | |
| 7,578,819 B2 | 8/2009 | Bleich et al. | |
| 7,617,006 B2 | 11/2009 | Metzler et al. | |
| 7,641,658 B2 | 1/2010 | Shaolian et al. | |
| 7,648,521 B2 | 1/2010 | Hestad | |
| 7,655,026 B2 | 2/2010 | Justis et al. | |
| 7,666,186 B2 | 2/2010 | Harp | |
| 7,666,209 B2 | 2/2010 | Zucherman et al. | |
| 7,738,968 B2 | 6/2010 | Bleich | |
| 7,738,969 B2 | 6/2010 | Bleich | |
| 7,740,631 B2 | 6/2010 | Bleich et al. | |
| 7,857,813 B2 | 12/2010 | Schmitz et al. | |
| 7,887,538 B2 | 2/2011 | Bleich et al. | |
| 7,918,849 B2 | 4/2011 | Bleich et al. | |
| 7,938,830 B2 | 5/2011 | Saadat et al. | |
| 7,959,577 B2 | 6/2011 | Schmitz et al. | |
| 7,963,915 B2 | 6/2011 | Bleich | |

(56) References Cited

U.S. PATENT DOCUMENTS

| | | |
|---|---|---|
| 8,048,080 B2 | 11/2011 | Bleich et al. |
| 8,062,298 B2 | 11/2011 | Schmitz et al. |
| 8,062,300 B2 | 11/2011 | Schmitz et al. |
| 8,092,456 B2 | 1/2012 | Bleich et al. |
| 8,192,435 B2 | 6/2012 | Bleich et al. |
| 8,192,436 B2 | 6/2012 | Schmitz et al. |
| 8,221,397 B2 | 7/2012 | Bleich et al. |
| 8,257,356 B2 | 9/2012 | Bleich et al. |
| 8,303,516 B2 | 11/2012 | Schmitz et al. |
| 8,366,712 B2 | 2/2013 | Bleich et al. |
| 8,394,102 B2 | 3/2013 | Garabedian et al. |
| 8,398,641 B2 | 3/2013 | Wallace et al. |
| 8,409,206 B2 | 4/2013 | Wallace et al. |
| 8,419,653 B2 | 4/2013 | Bleich et al. |
| 8,430,881 B2 | 4/2013 | Bleich et al. |
| 8,551,097 B2 | 10/2013 | Schmitz et al. |
| 8,568,416 B2 | 10/2013 | Schmitz et al. |
| 8,579,902 B2 | 11/2013 | Bleich et al. |
| 8,585,704 B2 | 11/2013 | Schmitz et al. |
| 8,613,745 B2 | 12/2013 | Bleich |
| 8,617,163 B2 | 12/2013 | Bleich |
| 2001/0014806 A1 | 8/2001 | Ellman et al. |
| 2001/0025192 A1 | 9/2001 | Gerber et al. |
| 2001/0039419 A1 | 11/2001 | Francischelli et al. |
| 2001/0049527 A1 | 12/2001 | Cragg |
| 2001/0053885 A1 | 12/2001 | Gielen et al. |
| 2002/0016555 A1 | 2/2002 | Ritchart et al. |
| 2002/0019637 A1 | 2/2002 | Frey et al. |
| 2002/0022788 A1 | 2/2002 | Corvi et al. |
| 2002/0022873 A1 | 2/2002 | Erickson et al. |
| 2002/0029060 A1 | 3/2002 | Hogendijk |
| 2002/0106681 A1 | 8/2002 | Wexler et al. |
| 2002/0128700 A1 | 9/2002 | Cross |
| 2002/0138091 A1 | 9/2002 | Pflueger |
| 2002/0165590 A1 | 11/2002 | Crowe et al. |
| 2002/0183647 A1 | 12/2002 | Gozani et al. |
| 2003/0015203 A1 | 1/2003 | Makower et al. |
| 2003/0023190 A1 | 1/2003 | Cox |
| 2003/0045808 A1 | 3/2003 | Kaula et al. |
| 2003/0045937 A1 | 3/2003 | Ginn |
| 2003/0074037 A1 | 4/2003 | Moore et al. |
| 2003/0105503 A1 | 6/2003 | Marino |
| 2003/0109871 A1 | 6/2003 | Johnson et al. |
| 2003/0113906 A1 | 6/2003 | Sangha et al. |
| 2003/0130655 A1 | 7/2003 | Woloszko et al. |
| 2003/0130738 A1 | 7/2003 | Hovda et al. |
| 2003/0167021 A1 | 9/2003 | Shimm |
| 2003/0187368 A1 | 10/2003 | Sata et al. |
| 2003/0188749 A1 | 10/2003 | Nichols et al. |
| 2003/0208206 A1 | 11/2003 | Gitis et al. |
| 2003/0212400 A1 | 11/2003 | Bloemer et al. |
| 2003/0225412 A1 | 12/2003 | Shiraishi |
| 2003/0225415 A1 | 12/2003 | Richard |
| 2004/0006379 A1 | 1/2004 | Brett |
| 2004/0006391 A1 | 1/2004 | Reiley |
| 2004/0019359 A1 | 1/2004 | Worley et al. |
| 2004/0024399 A1 | 2/2004 | Sharps et al. |
| 2004/0030330 A1 | 2/2004 | Brassell et al. |
| 2004/0049179 A1 | 3/2004 | Francischelli et al. |
| 2004/0049208 A1 | 3/2004 | Hill et al. |
| 2004/0054368 A1 | 3/2004 | Truckai et al. |
| 2004/0059247 A1 | 3/2004 | Urmey |
| 2004/0064058 A1 | 4/2004 | McKay |
| 2004/0067000 A1 | 4/2004 | Bates et al. |
| 2004/0097927 A1 | 5/2004 | Yeung et al. |
| 2004/0102721 A1 | 5/2004 | McKinley |
| 2004/0106940 A1 | 6/2004 | Shaolian et al. |
| 2004/0111084 A1 | 6/2004 | Brett |
| 2004/0116977 A1 | 6/2004 | Finch et al. |
| 2004/0122433 A1 | 6/2004 | Loubens et al. |
| 2004/0122459 A1 | 6/2004 | Harp |
| 2004/0122482 A1 | 6/2004 | Tung et al. |
| 2004/0127893 A1 | 7/2004 | Hovda |
| 2004/0127963 A1 | 7/2004 | Uchida et al. |
| 2004/0133208 A1 | 7/2004 | Weikel et al. |
| 2004/0143165 A1 | 7/2004 | Alleyne |
| 2004/0143280 A1 | 7/2004 | Suddaby |
| 2004/0162609 A1 | 8/2004 | Hossainy et al. |
| 2004/0167444 A1 | 8/2004 | Laroya et al. |
| 2004/0167553 A1 | 8/2004 | Simpson et al. |
| 2004/0181150 A1 | 9/2004 | Evans et al. |
| 2004/0199159 A1 | 10/2004 | Lee et al. |
| 2004/0199166 A1 | 10/2004 | Schmieding et al. |
| 2004/0225233 A1 | 11/2004 | Frankowski |
| 2004/0260358 A1 | 12/2004 | Vaughan et al. |
| 2005/0027199 A1 | 2/2005 | Clarke |
| 2005/0033393 A1 | 2/2005 | Daglow |
| 2005/0049592 A1 | 3/2005 | Keith et al. |
| 2005/0060006 A1 | 3/2005 | Pflueger et al. |
| 2005/0075578 A1 | 4/2005 | Gharib et al. |
| 2005/0149034 A1 | 7/2005 | Assell et al. |
| 2005/0149035 A1 | 7/2005 | Pimenta et al. |
| 2005/0149154 A1 | 7/2005 | Cohen et al. |
| 2005/0171587 A1 | 8/2005 | Daglow et al. |
| 2005/0182454 A1 | 8/2005 | Gharib et al. |
| 2005/0187537 A1 | 8/2005 | Loeb et al. |
| 2005/0197661 A1 | 9/2005 | Carrison et al. |
| 2005/0203599 A1 | 9/2005 | Garabedian et al. |
| 2005/0209610 A1 | 9/2005 | Carrison |
| 2005/0209617 A1 | 9/2005 | Koven et al. |
| 2005/0209622 A1 | 9/2005 | Carrison |
| 2005/0216023 A1 | 9/2005 | Aram et al. |
| 2005/0222598 A1 | 10/2005 | Ho et al. |
| 2005/0222647 A1 | 10/2005 | Wahlstrand et al. |
| 2005/0234425 A1 | 10/2005 | Miller et al. |
| 2005/0256423 A1 | 11/2005 | Kirsner |
| 2005/0261692 A1 | 11/2005 | Carrison et al. |
| 2005/0267529 A1 | 12/2005 | Crockett et al. |
| 2005/0277942 A1 | 12/2005 | Kullas et al. |
| 2005/0283148 A1 | 12/2005 | Janssen et al. |
| 2005/0283204 A1 | 12/2005 | Buhlmann et al. |
| 2006/0004369 A1 | 1/2006 | Patel et al. |
| 2006/0015035 A1 | 1/2006 | Rock |
| 2006/0025702 A1 | 2/2006 | Sterrantino et al. |
| 2006/0025703 A1 | 2/2006 | Miles et al. |
| 2006/0025797 A1 | 2/2006 | Lock et al. |
| 2006/0030854 A1 | 2/2006 | Haines |
| 2006/0036211 A1 | 2/2006 | Solsberg et al. |
| 2006/0036271 A1 | 2/2006 | Schomer et al. |
| 2006/0036272 A1 | 2/2006 | Solsberg et al. |
| 2006/0058732 A1 | 3/2006 | Harp |
| 2006/0064101 A1 | 3/2006 | Arramon |
| 2006/0079919 A1 | 4/2006 | Harp |
| 2006/0085048 A1 | 4/2006 | Cory et al. |
| 2006/0085049 A1 | 4/2006 | Cory et al. |
| 2006/0089650 A1 | 4/2006 | Nolde |
| 2006/0089688 A1 | 4/2006 | Panescu |
| 2006/0095026 A1 | 5/2006 | Ricart et al. |
| 2006/0095028 A1 | 5/2006 | Bleich |
| 2006/0122458 A1 | 6/2006 | Bleich |
| 2006/0122620 A1 | 6/2006 | Kim |
| 2006/0122653 A1 | 6/2006 | Bradley et al. |
| 2006/0122654 A1 | 6/2006 | Bradley et al. |
| 2006/0129201 A1 | 6/2006 | Lee et al. |
| 2006/0142753 A1 | 6/2006 | Francischelli et al. |
| 2006/0149278 A1 | 7/2006 | Abdou |
| 2006/0161189 A1 | 7/2006 | Harp |
| 2006/0173374 A1 | 8/2006 | Neubardt et al. |
| 2006/0184175 A1 | 8/2006 | Schomer et al. |
| 2006/0195107 A1 | 8/2006 | Jones et al. |
| 2006/0200153 A1 | 9/2006 | Harp |
| 2006/0200154 A1 | 9/2006 | Harp |
| 2006/0200155 A1 | 9/2006 | Harp |
| 2006/0200219 A1 | 9/2006 | Thrope et al. |
| 2006/0206115 A1 | 9/2006 | Schomer et al. |
| 2006/0206117 A1 | 9/2006 | Harp |
| 2006/0206118 A1 | 9/2006 | Kim et al. |
| 2006/0206178 A1 | 9/2006 | Kim |
| 2006/0224060 A1 | 10/2006 | Garell et al. |
| 2006/0224078 A1 | 10/2006 | Hoey et al. |
| 2006/0235451 A1 | 10/2006 | Schomer et al. |
| 2006/0235452 A1 | 10/2006 | Schomer et al. |
| 2006/0264952 A1 | 11/2006 | Nelson et al. |
| 2006/0264994 A1 | 11/2006 | Schomer et al. |

(56) References Cited

U.S. PATENT DOCUMENTS

| | | |
|---|---|---|
| 2006/0276720 A1 | 12/2006 | McGinnis et al. |
| 2006/0276802 A1 | 12/2006 | Vresilovic et al. |
| 2006/0276836 A1 | 12/2006 | Bergin et al. |
| 2007/0010717 A1 | 1/2007 | Cragg |
| 2007/0016097 A1 | 1/2007 | Farquhar et al. |
| 2007/0016185 A1 | 1/2007 | Tullis et al. |
| 2007/0027464 A1 | 2/2007 | Way et al. |
| 2007/0027514 A1 | 2/2007 | Gerber |
| 2007/0049962 A1 | 3/2007 | Marino et al. |
| 2007/0055215 A1 | 3/2007 | Tran et al. |
| 2007/0055262 A1 | 3/2007 | Tomita et al. |
| 2007/0055263 A1 | 3/2007 | Way et al. |
| 2007/0073356 A1 | 3/2007 | Rooney et al. |
| 2007/0106219 A1 | 5/2007 | Grabinsky |
| 2007/0123766 A1 | 5/2007 | Whalen, III et al. |
| 2007/0123890 A1 | 5/2007 | Way et al. |
| 2007/0162044 A1 | 7/2007 | Marino |
| 2007/0162061 A1 | 7/2007 | Way et al. |
| 2007/0162062 A1 | 7/2007 | Norton et al. |
| 2007/0166345 A1 | 7/2007 | Pavcnik et al. |
| 2007/0168007 A1 | 7/2007 | Kuzma et al. |
| 2007/0198019 A1 | 8/2007 | Schomer et al. |
| 2007/0213583 A1 | 9/2007 | Kim et al. |
| 2007/0213584 A1 | 9/2007 | Kim et al. |
| 2007/0213734 A1 | 9/2007 | Bleich et al. |
| 2007/0213795 A1 | 9/2007 | Bradley et al. |
| 2007/0255162 A1 | 11/2007 | Abboud et al. |
| 2007/0255369 A1 | 11/2007 | Bonde et al. |
| 2007/0270795 A1 | 11/2007 | Francischelli et al. |
| 2007/0270865 A1 | 11/2007 | Arnin et al. |
| 2007/0276286 A1 | 11/2007 | Miller |
| 2007/0276390 A1 | 11/2007 | Solsberg et al. |
| 2007/0282217 A1 | 12/2007 | McGinnis et al. |
| 2007/0299403 A1 | 12/2007 | Crowe et al. |
| 2007/0299459 A1 | 12/2007 | Way et al. |
| 2008/0015582 A1 | 1/2008 | DiPoto et al. |
| 2008/0033465 A1 | 2/2008 | Schmitz et al. |
| 2008/0051812 A1 | 2/2008 | Schmitz et al. |
| 2008/0058874 A1 | 3/2008 | Westlund et al. |
| 2008/0086034 A1 | 4/2008 | Schmitz et al. |
| 2008/0091227 A1 | 4/2008 | Schmitz et al. |
| 2008/0097465 A1 | 4/2008 | Rollins et al. |
| 2008/0103504 A1 | 5/2008 | Schmitz et al. |
| 2008/0119711 A1 | 5/2008 | Nikumb et al. |
| 2008/0125621 A1 | 5/2008 | Gellman et al. |
| 2008/0125709 A1 | 5/2008 | Chang et al. |
| 2008/0140153 A1 | 6/2008 | Burdulis |
| 2008/0140169 A1 | 6/2008 | Imran |
| 2008/0146867 A1 | 6/2008 | Gellman et al. |
| 2008/0147084 A1 | 6/2008 | Bleich et al. |
| 2008/0161809 A1 | 7/2008 | Schmitz et al. |
| 2008/0161810 A1 | 7/2008 | Melkent |
| 2008/0188850 A1 | 8/2008 | Mody et al. |
| 2008/0197024 A1 | 8/2008 | Simpson et al. |
| 2008/0200912 A1 | 8/2008 | Long et al. |
| 2008/0221383 A1 | 9/2008 | Way et al. |
| 2008/0221586 A1 | 9/2008 | Garcia-Bengochea et al. |
| 2008/0288005 A1 | 11/2008 | Jackson |
| 2008/0312660 A1 | 12/2008 | Bleich et al. |
| 2008/0319459 A1 | 12/2008 | Al-najjar |
| 2009/0018507 A1 | 1/2009 | Schmitz et al. |
| 2009/0018610 A1 | 1/2009 | Gharib et al. |
| 2009/0082763 A1 | 3/2009 | Quick et al. |
| 2009/0105604 A1 | 4/2009 | Bertagnoli et al. |
| 2009/0138056 A1 | 5/2009 | Anderson et al. |
| 2009/0143829 A1 | 6/2009 | Shluzas |
| 2009/0171381 A1 | 7/2009 | Schmitz et al. |
| 2009/0177112 A1 | 7/2009 | Gharib et al. |
| 2009/0182382 A1 | 7/2009 | Justis et al. |
| 2009/0209879 A1 | 8/2009 | Kaula et al. |
| 2010/0004654 A1 | 1/2010 | Schmitz et al. |
| 2010/0057087 A1 | 3/2010 | Cha |
| 2010/0094231 A1 | 4/2010 | Bleich et al. |
| 2010/0331883 A1 | 12/2010 | Schmitz et al. |
| 2011/0004207 A1 | 1/2011 | Wallace et al. |
| 2011/0060314 A1 | 3/2011 | Wallace et al. |
| 2011/0112539 A1 | 5/2011 | Wallace et al. |
| 2011/0160731 A1 | 6/2011 | Bleich et al. |
| 2011/0160772 A1 | 6/2011 | Arcenio et al. |
| 2011/0190772 A1 | 8/2011 | Saadat et al. |
| 2012/0016368 A1 | 1/2012 | Bleich et al. |
| 2012/0065639 A1 | 3/2012 | Schmitz et al. |
| 2012/0123294 A1 | 5/2012 | Sun et al. |
| 2012/0143206 A1 | 6/2012 | Wallace et al. |
| 2012/0191003 A1 | 7/2012 | Garabedian et al. |
| 2012/0239041 A1 | 9/2012 | Bleich et al. |
| 2013/0012831 A1 | 1/2013 | Schmitz et al. |
| 2013/0053853 A1 | 2/2013 | Schmitz et al. |
| 2013/0150855 A1 | 6/2013 | Bleich et al. |
| 2013/0150856 A1 | 6/2013 | Mimran et al. |
| 2013/0172895 A1 | 7/2013 | Wallace et al. |
| 2013/0310837 A1 | 11/2013 | Saadat et al. |

FOREIGN PATENT DOCUMENTS

| | | |
|---|---|---|
| DE | 3209403 A1 | 9/1983 |
| DE | 4036804 A1 | 5/1992 |
| EP | 359883 A1 | 3/1990 |
| EP | 1304080 A2 | 4/2003 |
| EP | 1340467 A2 | 9/2003 |
| EP | 1207794 B1 | 5/2004 |
| EP | 1315463 B1 | 5/2005 |
| EP | 1611851 A1 | 1/2006 |
| EP | 1006885 B1 | 9/2006 |
| FR | 2706309 | 12/1994 |
| GB | 1460837 A | 1/1977 |
| JP | 2960140 B2 | 10/1999 |
| JP | 23116868 | 4/2003 |
| JP | 24065380 A2 | 3/2004 |
| RU | 2107459 | 3/1998 |
| WO | WO92/22259 A2 | 12/1992 |
| WO | WO96/22057 A1 | 7/1996 |
| WO | WO97/14362 A1 | 4/1997 |
| WO | WO97/34536 A2 | 9/1997 |
| WO | WO99/18866 A1 | 4/1999 |
| WO | WO99/21500 A1 | 5/1999 |
| WO | WO00/67651 A1 | 11/2000 |
| WO | WO01/08571 A1 | 2/2001 |
| WO | WO0108571 * | 2/2001 |
| WO | WO01/62168 A2 | 8/2001 |
| WO | WO02/07901 A1 | 1/2002 |
| WO | WO02/34120 A2 | 5/2002 |
| WO | WO02/076311 A2 | 10/2002 |
| WO | WO03/026482 A2 | 4/2003 |
| WO | WO03/066147 A1 | 8/2003 |
| WO | WO2004/002331 A1 | 1/2004 |
| WO | WO2004/028351 A2 | 4/2004 |
| WO | WO2004/043272 A1 | 5/2004 |
| WO | WO2004/056267 A1 | 7/2004 |
| WO | WO2004/078066 A2 | 9/2004 |
| WO | WO2004/080316 A1 | 9/2004 |
| WO | WO2004/096080 A2 | 11/2004 |
| WO | WO2005/009300 A1 | 2/2005 |
| WO | WO2005/057467 A2 | 6/2005 |
| WO | WO2005/077282 A1 | 8/2005 |
| WO | WO2005/089433 A2 | 9/2005 |
| WO | WO2006/009705 A2 | 1/2006 |
| WO | WO2006/015302 A1 | 2/2006 |
| WO | WO2006/017507 A2 | 2/2006 |
| WO | WO2006/039279 A2 | 4/2006 |
| WO | WO2006/042206 A2 | 4/2006 |
| WO | WO2006/044727 A2 | 4/2006 |
| WO | WO2006/047598 A1 | 5/2006 |
| WO | WO2006/058079 A2 | 6/2006 |
| WO | WO2006/058195 A2 | 6/2006 |
| WO | WO2006/062555 A2 | 6/2006 |
| WO | WO2006/086241 A2 | 8/2006 |
| WO | WO2006/099285 A2 | 9/2006 |
| WO | WO2006/102085 A2 | 9/2006 |
| WO | WO2007/008709 A2 | 1/2007 |
| WO | WO2007/021588 A1 | 2/2007 |
| WO | WO2007/022194 A2 | 2/2007 |

(56) References Cited

FOREIGN PATENT DOCUMENTS

| WO | WO2007/059343 A2 | 2/2007 |
|---|---|---|
| WO | WO2007/067632 A2 | 6/2007 |
| WO | WO2008/008898 A2 | 1/2008 |

OTHER PUBLICATIONS

Schmitz et al.; U.S. Appl. No. 14/195,197 entitled "Tissue modification devices," filed Mar. 3, 2014.
Leguidleguid et al.; U.S. Appl. No. 14/209,418 entitled "Tissue Modification Devices," filed Mar. 13, 2014.
Abdel-Wanis et al., "Tumor growth potential after tumoral and instrumental contamination: an in-vivo comparative study of T-saw, Gigli saw, and scalpel," Journal of orthopaedic science, Sep. 2001, vol. 6, 424-429.
Barer Malvin, "Instrument to Enhance Passage of the Gigli Saw," Journal of Pediatric Orthopedics, Raven Press, New York, Nov. 1984, 4:762-763.
Baumgart et al., "Indikation and Technik der Knochendurchtrennung," Der Chirurg, Nov. 1998, vol. 69:1188-1196. (in German with Eng Summary).
Bohinski et al., "Novel use of a threadwire saw for high sacral amputation," Journal of neurosurgery: Spine, Jul. 2005, vol. 3(1): 71-78.
Brunori et al., "Celebrating the centennial (1894-1994): Leonardo Gigli and his wire saw," J. Neurosurg, Jun. 1995, 82(6):1086-1090.
Burrows, Harold, "Surgical instruments and appliances used in operations," Faber and Faber, London, Jan. 1937, total pp. 4.
Codman Laminectomy Shaver (a Johnson & Johnson company www.codman.com) catalogue, pp. 416-431, [online] Retrieved from the internet: <URL: http:llwww.codman.com/PDFs/Catalog_04_R.pdf>; date of publication unknown; available to applicants at least as of Nov. 22, 2006.
Dammann, Gordon, Pictorial Encyclopedia of Civil War Medical Instruments and Equipment, Pictorial Histories Publishing Company, Missoula, Montana, Apr. 1, 1983, Total pp. 2.
Edwards et al; "T-Saw Laminoplasty for the Management of Cervical Spondylotic Myelopathy," SPINE, Lippincott Williams & Wilkins, Inc., Jul. 15, 2000, vol. 25(14): 1788-1794.
Ellman Int. Disc-FX System Accessories K052241 [online] Retrieved from the Internet: <URL: http://www.ellman.com/medical/>; 1 page; date of publication unknown; available to applicants at least as of Nov. 22, 2006.
Eralp et al., "A comparison of two osteotomy techniques for tibial lengthening," Archives of orthopaedic and trauma surgery, Jun. 2004, vol. 124: pp. 298-300.
Fessler Richard G, "Minimally Invasive Microendoscopic Decompressive Laminotomy for Lumbar Stenosis," American Association of Neurological Surgeons, 2006, Online CME course, 26 pages total, [Retrieved on Jun. 29, 2006 from the internet http://www.aans.emedtrain.com/lumbar_stenosis/lumbarStenosis.swf.
Fujita et al., "Chordoma in the Cervical Spine Managed with En Bloc Excision," SPINE, Lippincott Williams & Wilkins, Inc., Sep. 1, 1999, 24 (17):1848-1851.
Goel, Atul, "Neurosurgical forum, Supraorbital Craniotomy," Journal of Neurosurgery, Oct. 1994, vol. 81, 642-643.
Gore Smoother User Manual, W. L. Gore & Associates, Inc. Flagstaff, AZ, Dec. 1999,Total pp. 3.
Hara et al., "En Bloc Laminoplasty Performed with Threadwire Saw: Technical Note," Neurosurgery, Jan. 2001, vol. 48, No. 1, pp. 235-239.
Hata et al; "A less invasive surgery for rotator cuff tear: Mini-open repair," Journal of Shoulder and Elbow Surgery, Jan. 2001, vol. 10 No. 1, 11-16.
Berkowitz, "The Cervical Spine Surgery Atlas", 2004, Lippincott Williams & Wilkins; 2nd Edition; pp. 203-206, & 208; Dec. 2003.
Honl et al; "The Use of Water-Jetting Technology in Prostheses Revision Surgery...," J. Biomed Mater Res (Applied Biomaterials),
John Wiley & Sons, Inc, 2000, 53(6): 781-790 (year of pub. is sufficiently earlier than effective U.S. filing date & any foreign priority date).
Integra Ruggles TM Kerrison Rongeurs [online]; Retrieved from the internet: <URL: http://www.integra-Is.com/products!? product=22> on Oct. 17, 2006; 2 pages.
Jun, Byung-Yoon, "Posterior Lumbar Interbody Fusion With Restoration of Lamina and Facet Fusion," SPINE, Lippincott Williams & Wilkins, Inc., Apr. 15, 2000, vol. 25, No. 8, pp. 917-922.
Kawahara et al., "Recapping T-Saw Laminoplasty for Spinal Cord Tumors," SPINE, Jul. 1, 1999, vol. 24 No. 13, pp. 1363-1370.
Martin-Benlloch et al., "Expansive Laminoplasty as a Method for Managing Cervical Multilevel Spondylotic Myelopathy," SPINE, Lippincott Williams & Wilkins, Inc., Apr. 1, 2003, vol. 28, No. 7, pp. 680-684.
Miyamoto et al., "Kyphectomy Using a Surgical Threadwire (T-saw) for Kyphotic Deformity in a Child With Myelomeningocele," SPINE, Lippincott Williams & Wilkins, Inc., May 15, 2003, vol. 28, No. 10, pp. E187-E190.
Mopec Bone-Cutting tool, Product brochure; Dec. 15, 2005; Total pp. 4.
Nakagiri et al., "Thoracoscopic Rib Resection Using a Gigli Saw," The Annals of Thoracic Surgery, Aug. 2005, vol. 80, pp. 755-756.
Osaka et al., "Clinical significance of a wide excision policy for sacrococcygeal chordoma," J Cancer Res Clin Oncol, Dec. 16, 2005, Total pp. 6.
Paktiss et al., "Afghan Percutaneous Osteotomy," Journal of Pediatric Orthopaedics, Raven Press Ltd, New York, Jul.-Aug. 1993, vol. 13, No. 4, 531-533.
Paley et al., "Percutaneous Osteotomies," Orthopedic Clinics of North America, Oct. 1991, vol. 22, No. 4, pp. 613-624.
Pancoast, Joseph, "A Treatise on Operative Surgery," Carey and Hart, Philadelphia, (year of publication is sufficiently earlier than the effective U.S. filing date and any foreign priority date) 1844, Total pp. 11.
Park et al; "Cases of the Excision of Carious Joints," John Scrymgeour, Glasgow, (year of publication is sufficiently earlier than the effective U.S. filing date and any foreign priority date) 1806, Total pp. 6.
Peavy et al., "Comparison of Cortical Bone Ablations by Using Infrared Laser Wavelengths 2.9 to 9.2 µm, Lasers in Surgery and Medicine," (year of publication is sufficiently earlier than the effective U.S. filing date and any foreign priority date) 1999, vol. 26, pp. 421-434.
Peltier, Leonard Orthopedics: A History and Iconography, Norman Publishing, San Francisco, Feb. 1, 1993, Total pp. 3.
Reckling Frederick, "Modified Stethoscope Earpiece Makes Excellent Gigli Saw Guide," J Bone and Joint Surgery Am, Dec. 1972, 54-A(8), 1787-1788.
Rutkow, Ira, "Surgery: An Illustrated History," Mosby'Year Book, Inc., St. Louis, Oct. 1, 1993, Total pp. 4.
Schwieger et al., "Abrasive Water Jet Cutting as a New Procedure for Cutting Cancellous Bones'In Vitro Testing in Comparison with the Oscillating Saw," Wiley Interscience, www.interscience,wiley.com, Sep. 20, 2004, pp. 223-228.
Sen et al., The reliability of percutaneous osteotomy with the Gigli saw technique in the proximal tibia;36(2); pp. 136-140; (year of publication is sufficiently earlier than the effective U.S. filing date and any foreign priority date) 2002, (Turkish w/ Eng Trans.).
Shiraishi et al., "Results of Skip Laminectomy—Minimum 2-Year Follow-up Study Compared With Open-Door Laminoplasty," Spine, Lippincott Williams & Wilkins, Inc., Dec. 15, 2003, vol. 28, No. 24, pp. 2667-2672.
Shiraishi T., "A new technique for exposure of the cervical spine laminae. Technical note," Journal of neurosurgery. Spine, Jan. 2002, vol. 96(1), 122-126.
Shiraishi T., Skip laminectomy—a new treatment for cervical spondylotic myelopathy, preserving bilateral muscular attachments to the spinous processes: a preliminary report, Spine, Mar.-Apr. 2002, vol. 2(2), pp. 108-115.
Skippen et al., "The Chain Saw R A Scottish Invention," Scottish Medical Journal, May 2004, vol. 49(2), 72-75.

(56) References Cited

OTHER PUBLICATIONS

Stevens et al., "Calvarial Bone Graft Harvest Using the Gigli Saw," Journal of Oral and Maxillofacial Surgery, Jun. 1998, vol. 56(6): 798-799.

Takada et al., "Unusual Metastasis to the Cauda Equina From Renal Cell Carcinoma," SPINE, Lippincott Williams & Wilkins, Inc; Mar. 15, 2003, vol. 28 No. 6, pp. E114-E117.

Tomita et al., "Expansive Midline T-Saw Laminoplasty (Modified Spinour Process-Splitting) for the Management of Cervical Myelopathy," SPINE, Lippincott Williams & Wilkins, Inc; Jan. 1, 1998, 23(1): 32-37.

Tomita et al., "The Threadwire Saw: a New Device for Cutting Bone," The Journal of Bone and Joint Surgery, Dec. 1996, vol. 78(12): 1915-1917.

Tomita et al., "The Use of the T-Saw for Expansive Midline laminoplasty in the Treatment of Cervical Myelopathy," Orthopedics and Traumatology, vol. 10, No. 3, pp. 169-178, Sep. 2002.

Tomita et al., "Total en bloc spondylectomy and circumspinal decompression for solitary spinal metastasis," Paraplegia, Jan. 1994, 32(1):36-46.

Tomita K. et al., "Total en bloc spondylectomy for solitary spinal metastases," International Orthopaedics (SICOT), Oct. 1994, 18(5): 291-298.

Truax, Charles, "The Mechanics of Surgery," Chicago, IL; (year of publication is sufficiently earlier than the effective U.S. filing date and any foreign priority date) 1899, Total pp. 3.

US Surgical Kerrison Spinal Rongeur K943116 [online] Retrieved from the internet: <URL: http://www.ussurg.com/uss/index.html> Nov. 22, 2006; 1 page.

Wilkins, Robert H, "Neurosurgical Classics," Johnson Reprint Corporation, New York, (year of publication is sufficiently earlier than the effective U.S. filing date and any foreign priority date) 1965, pp. 377-382.

Zeppelin Laminectomy Rongeur K901372, [online] Retrieved from the internet: <URL: http://www.zeppelin-medical.com/download/instruments.pdf>, Oct. 24, 2006; 1 page.

Schmitz et al.; U.S. Appl. No. 14/023,893 entitled "Tissue Access Guidewire System and Method," filed Sep. 11, 2013.

Leguidleguid et al.; U.S. Appl. No. 14/061,641 entitled "Tissue Modification Devices," filed Oct. 23, 2013.

Schmitz et al.; U.S. Appl. No. 14/064,085 entitled "Access and Tissue Modification Systems and Methods," filed Oct. 25, 2013.

\* cited by examiner

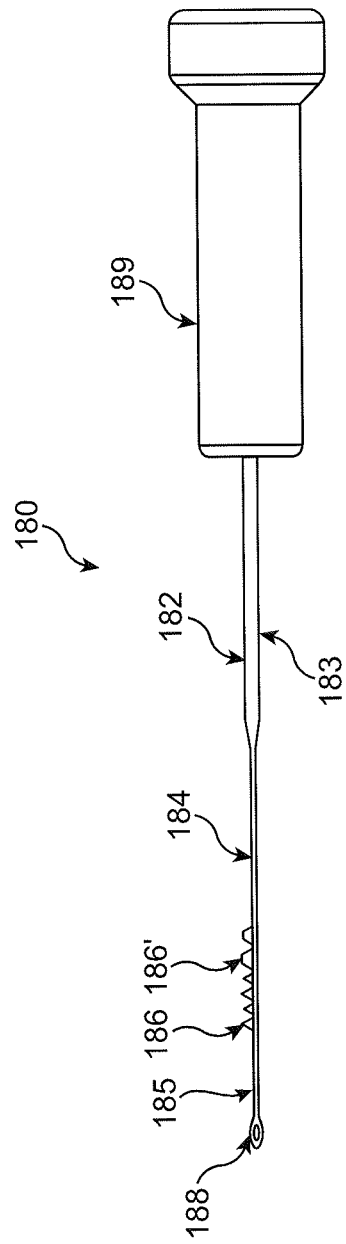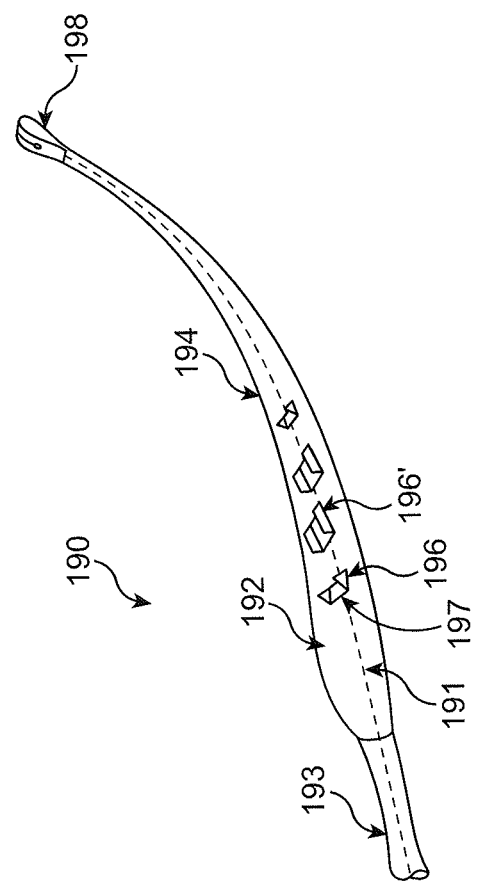

FLEXIBLE TISSUE REMOVAL DEVICES AND METHODS

CROSS REFERENCE TO RELATED APPLICATIONS

The present application is a continuation of U.S. patent application Ser. No. 13/267,683, titled "Flexible Tissue Removal Devices and Methods," filed Oct. 6, 2011, Publication No. US-2012-0022538-A1, which is a continuation of U.S. patent application Ser. No. 11/687,558, titled "Flexible Tissue Removal Devices and Methods," filed Mar. 16, 2007, now U.S. Pat. No. 8,062,298, which is a continuation-in-part of U.S. patent application Ser. No. 11/429,377, titled "Flexible Tissue Rasp," filed May 4, 2006, now U.S. Pat. No. 8,048,080, each of which is herein incorporated by reference in its entirety. U.S. patent application Ser. No. 11/687,558 also claims priority from U.S. Provisional Patent Application Ser. No. 60/869,070, titled "Flexible Tissue Removal Devices and Methods," filed Dec. 7, 2006, which is herein incorporated by reference in its entirety.

The present application is related to, but does not claim priority from, PCT Patent Application Pub. No. PCT/US2005/037136, titled "Devices and Methods for Selective Surgical Removal of Tissue, filed Oct. 15, 2005, which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND OF THE INVENTION

The present invention relates generally to medical/surgical devices and methods. More specifically, the present invention relates to flexible tissue modification devices and methods.

A significant number of surgical procedures involve modifying tissue in a patient's body, such as by removing, cutting, shaving, abrading, shrinking, ablating or otherwise modifying tissue. Minimally invasive (or "less invasive") surgical procedures often involve modifying tissue through one or more small incisions or percutaneous access, and thus may be more technically challenging procedures. Some of the challenges of minimally invasive tissue modification procedures include working in a smaller operating field, working with smaller devices, and trying to operate with reduced or even no direct visualization of the tissue (or tissues) being modified. For example, using arthroscopic surgical techniques for repairing joints such as the knee or the shoulder, it may be quite challenging to modify certain tissues to achieve a desired result, due to the required small size of arthroscopic instruments, the confined surgical space of the joint, lack of direct visualization of the surgical space, and the like. It may be particularly challenging in some surgical procedures, for example, to cut or contour bone or ligamentous tissue with currently available minimally invasive tools and techniques. For example, trying to shave a thin slice of bone off a curved bony surface, using a small-diameter tool in a confined space with little or no ability to see the surface being cut, as may be required in some procedures, may be incredibly challenging or even impossible using currently available devices.

One area of surgery which would likely benefit from the development of less invasive techniques is the treatment of spinal stenosis. Spinal stenosis occurs when nerve tissue and/or the blood vessels supplying nerve tissue in the spine become impinged by one or more structures pressing against them, causing symptoms. The most common form of spinal stenosis occurs in the lower (or lumbar) spine and can cause severe pain, numbness and/or loss of function in the lower back and/or one or both lower limb.

FIG. 1 is a top view of a vertebra with the cauda equina (the bundle of nerves that extends from the base of the spinal cord) shown in cross section and two nerve roots branching from the cauda equina to exit the central spinal canal and extend through intervertebral foramina on either side of the vertebra. Spinal stenosis can occur when the spinal cord, cauda equina and/or nerve root(s) are impinged by one or more tissues in the spine, such as buckled or thickened ligamentum flavum, hypertrophied facet joint (shown as superior articular processes in FIG. 1), osteophytes (or "bone spurs") on vertebrae, spondylolisthesis (sliding of one vertebra relative to an adjacent vertebra), facet joint synovial cysts, and/or collapse, bulging or herniation of an intervertebral disc. Impingement of neural and/or neurovascular tissue in the spine by one or more of these tissues may cause pain, numbness and/or loss of strength or mobility in one or both of a patient's lower limbs and/or of the patient's back.

In the United States, spinal stenosis occurs with an incidence of between 4% and 6% (or more) of adults aged 50 and older and is the most frequent reason cited for back surgery in patients aged 60 and older. Patients suffering from spinal stenosis are typically first treated with conservative approaches such as exercise therapy, analgesics, anti-inflammatory medications, and epidural steroid injections. When these conservative treatment options fail and symptoms are severe, as is frequently the case, surgery may be required to remove impinging tissue and decompress the impinged nerve tissue.

Lumbar spinal stenosis surgery involves first making an incision in the back and stripping muscles and supporting structures away from the spine to expose the posterior aspect of the vertebral column. Thickened ligamentum flavum is then exposed by complete or partial removal of the bony arch (lamina) covering the back of the spinal canal (laminectomy or laminotomy). In addition, the surgery often includes partial or complete facetectomy (removal of all or part of one or more facet joints), to remove impinging ligamentum flavum or bone tissue. Spinal stenosis surgery is performed under general anesthesia, and patients are usually admitted to the hospital for five to seven days after surgery, with full recovery from surgery requiring between six weeks and three months. Many patients need extended therapy at a rehabilitation facility to regain enough mobility to live independently.

Removal of vertebral bone, as occurs in laminectomy and facetectomy, often leaves the effected area of the spine very unstable, leading to a need for an additional highly invasive fusion procedure that puts extra demands on the patient's vertebrae and limits the patient's ability to move. Unfortunately, a surgical spine fusion results in a loss of ability to move the fused section of the back, diminishing the patient's range of motion and causing stress on the discs and facet joints of adjacent vertebral segments. Such stress on adjacent vertebrae often leads to further dysfunction of the spine, back pain, lower leg weakness or pain, and/or other symptoms. Furthermore, using current surgical techniques, gaining sufficient access to the spine to perform a laminectomy, facetectomy and spinal fusion requires dissecting through a wide incision on the back and typically causes extensive muscle damage, leading to significant post-operative pain and lengthy rehabilitation. Thus, while laminectomy, facetectomy, and spinal fusion frequently improve symptoms of neural and neurovascular impingement in the short term, these procedures are highly invasive, diminish spinal function, drastically disrupt normal anatomy, and increase long-term morbidity above levels seen in untreated patients.

Therefore, it would be desirable to have less invasive methods and devices for modifying target tissue in a spine to help ameliorate or treat spinal stenosis, while inhibiting unwanted damage to non-target tissues. Ideally, such techniques and devices would reduce neural and/or neurovascular impingement without removing significant amounts of vertebral bone, joint, or other spinal support structures, thereby avoiding the need for spinal fusion and, ideally, reducing the long-term morbidity resulting from currently available surgical treatments. It may also be advantageous to have minimally invasive or less invasive tissue modification devices capable of treating target tissues in parts of the body other than the spine. At least some of these objectives will be met by the present invention.

SUMMARY OF THE INVENTION

In various embodiments, devices, systems and methods of the present invention provide minimally invasive or less invasive modification of tissue in a patient. For the purposes of this application, the phrase "tissue modification" includes any type of tissue modification, such as but not limited to removing, cutting, shaving, abrading, shrinking, ablating, shredding, sanding, filing, contouring, carving, melting, heating, cooling, desiccating, expanding, moving, delivering medication or other substance(s) to tissue and/or delivering an implantable device (such as a stent) to tissue.

In one aspect of the present invention, a device for removing tissue from a patient may include: an elongate flexible body having a proximal end, a distal end, and a longitudinal axis therebetween, the elongate body having opposed first and second major surfaces with a lateral orientation across the axis; and a plurality of blades distributed laterally across the first major surface. Each blade may have a first end adjacent the first surface and extending to a cantilevered second end, a first edge between the first and second ends of the blade being oriented toward the distal end of the elongate body, a second edge between the first and second ends of the blade being oriented toward the proximal end of the elongate body, a height of the blade between its first and second ends, and an axial length of the blade between its first and second edges. The first edge and/or the second edge may comprise a cutting edge so as to axially cut the ligament when the first surface is urged toward the ligament and the elongate body advances along a path toward one end of the elongate body. Both the height and the axial length of each blade may be greater than a transverse width of the blade.

In some embodiments, each blade of the device may have an associated base extending along and affixed to the first surface with an angle or bend therebetween. Additionally, in some embodiments, at least some of the bases may be disposed laterally between a first associated blade and a second associated blade. In some embodiments, both the first edge and the second edge of each blade may comprise a cutting edge so as to axially cut the ligament and effect removal of the ligament when the elongate body reciprocates along the path.

In one embodiment, the tissue may comprise ligament tissue disposed over a curved bone surface, the second ends of at least some of the blades may comprise bone-cutting tips and extend to a distal bone-engagement height from the first surface, and tension forces appliable manually to the proximal and distal ends of the elongate body may urge the bone cutting tips through the ligament and into the bone when the first surface bends over the ligament tissue and the elongate body is reciprocated axially. In some embodiments, the first surface, when bending over the bone surface, may have an active region with blades that can be urged into the ligament, and the manual tension forces divided by a combined surface area of the bone cutting tips within the active region may be at least about 30,000 psi.

In an alternative embodiment, the tissue may comprise ligament tissue disposed over a curved bone surface, the second ends of at least some of the blades may comprise bone-protecting surfaces and extend to a bone protecting height from the first surface, and tension forces appliable manually to the proximal and distal ends of the elongate body may result in sliding of the bone-protecting surfaces along the bone surface so as to inhibit removal of the bone when the first surface bends over the ligament tissue and the elongate body is reciprocated axially.

In another alternative embodiment, the tissue may comprise ligament tissue disposed over a curved bone surface, the second ends of at least some of the blades may comprise bone-contacting edges and extend to a bone-contacting height from the first surface, a first amount of tension force appliable manually to the proximal and distal ends of the elongate body may result in sliding of the bone-contacting edges along the bone surface so as to inhibit removal of the bone when the first surface bends over the ligament tissue and the elongate body is reciprocated axially, and a second amount of tension force appliable manually to the proximal and distal ends of the elongate body may cause the bone-contacting edges to cut bone when the first surface bends over the ligament tissue and the elongate body is reciprocated axially.

In some embodiments, a frontal surface area of the first or second edge of each blade may be less than a side surface area of each blade. In some embodiments, a side of each blade between its two edges may form an angle with the first surface of the elongate body of between about 45 degrees and about 90 degrees, and the side of each blade may be aligned at an angle of between about 0 degrees and about 45 degrees relative to the longitudinal axis of the elongate body. Even more preferably, in some embodiments, the side of each blade may form an angle with the first surface of between about 60 degrees and about 90 degrees, and the side of each blade may be aligned at an angle of between about 0 degrees and about 30 degrees relative to the longitudinal axis of the elongate body. In some embodiments, at least two blades may be aligned at different angles relative to the longitudinal axis of the elongate body.

In some embodiments, the elongate body may be configured to bend over a curved surface. In some embodiments, at least some of the blades may be axially offset from one another along the longitudinal axis of the elongate body.

In some embodiments, the device may be configured to modify spinal tissue, and the elongate body may be configured to extend into the patient's body, along a curved path through an intervertebral foramen of the spine, and out of the patient's body, such that a flexible portion of the elongate body of the device extends through the intervertebral foramen. In some embodiments, a height of each blade may be at least equal to a thickness of a ligamentum flavum of the spine.

In some embodiments, the elongate body may include a rigid shaft, a flexible portion extending from one end of the shaft, a guidewire coupler on or in the flexible portion, and a first handle coupled with an end of the shaft opposite the flexible portion. Optionally, the device may further include a guidewire configured to couple with the guidewire coupler and a second handle configured to couple with the guidewire outside the patient.

In various alternative embodiments, the second end of each blade may have a shape such as but not limited to a pointed tip, a flat edge, a round edge, a serrated edge, a saw-toothed edge or a curved edge. In some embodiments, second ends of at least two blades may have different shapes, relative to one another. In some embodiments, at least two blades may have different heights, relative to one another. In some embodiments, the blades may be fixedly attached to the first major surface.

In another aspect of the present invention, a device for removing tissue from a patient may include an elongate flexible body having a proximal end, a distal end, and a longitudinal axis therebetween, the elongate body having opposed first and second major surfaces with a lateral orientation across the axis and a plurality of blades distributed laterally across the first major surface, each blade having a first end adjacent the first surface and extending to a cantilevered second end. Each blade may substantially in-line with the longitudinal axis of the elongate body. Additionally, each blade may be substantially vertical relative to the first surface. By "substantially in-line," it is meant that a side of each blade is aligned at an angle of between about 0 degrees and about 45 degrees relative to the longitudinal axis of the elongate body. By "substantially vertical," it is meant that each blade forms an angle with the first surface of the elongate body of between about 45 degrees and about 90 degrees. In some preferred embodiments, the side of each blade may be aligned at an angle of between about 0 degrees and about 30 degrees relative to the longitudinal axis of the elongate body, and the side of each blade may form an angle with the first surface of between about 60 degrees and about 90 degrees.

In another aspect of the present invention, a method for removing target tissue from a patient may involve advancing an elongate flexible body along a path between the target tissue and a non-target tissue, the flexible body having a plurality of laterally offset, cantilevered blades extending therefrom, and advancing the blades through the target tissue by moving the elongate body axially along the path so as to form laterally offset cuts in the target tissue. In some embodiments, the target tissue may comprise ligament tissue disposed over bone, advancing the elongate body may involve advancing along a curved path, and the method may further involve applying pulling force at or near opposite ends of the elongate body to urge the laterally offset blades into the ligament tissue, such that at least one of the blades contacts the bone beneath the ligament.

In some embodiments, advancing the blades involves reciprocating the elongate body along the curved path. Some embodiments may further involve reciprocating the elongate body to remove a portion of the bone. In some embodiments, the elongate body may be advanced into an intervertebral foramen of the patient's spine, the target ligament tissue may comprise ligamentum flavum, and the non-target tissue may comprise neural tissue. Optionally, such a method may further include steering the elongate body sideways within the intervertebral foramen during the advancing step. In some embodiments, at least some of the blades may be angled relative to the longitudinal axis of the elongate body, and advancing the blades through the target tissue may cause cantilevered ends of the blades to ride along the bone to cause the elongate body to move sideways within the intervertebral foramen.

In some embodiments, the elongate body may be advanced percutaneously into the patient by pulling the device behind a guidewire. Some embodiments may further involve inhibiting damage to the non-target tissue with an atraumatic surface of the elongate body configured to contact the non-target tissue when the blades contact target tissue. Some embodiments of the method may further involve collecting cut tissue between at least some of the blades.

In another aspect of the present invention, a method for removing ligamentum flavum tissue in a spine of a patient to treat spinal stenosis may involve: advancing a flexible elongate body of a tissue modification device along a curved path through an intervertebral foramen in the spine, between ligamentum flavum and neural tissue; applying pulling force at or near opposite ends of the elongate body to advance at least one cantilevered, laterally offset blade coupled with a first major surface of the elongate body through the ligamentum flavum to contact vertebral bone, wherein each blade is substantially in-line with a longitudinal axis of the elongate body, and wherein each blade is substantially vertical relative to a the first major surface; and reciprocating the elongate body to remove ligamentum flavum tissue, wherein reciprocating the device while applying the force causes at least one of the blades to ride along the bone and move the elongate body laterally in the intervertebral foramen, relative to the longitudinal axis of the elongate body. In some embodiments, the method may further involve inhibiting damage to the neural tissue with an atraumatic second major surface of the elongate body opposite the first major surface.

These and other aspects and embodiments are described more fully below in the Detailed Description, with reference to the attached Drawings.

BRIEF DESCRIPTION OF THE DRAWINGS

FIG. 24 is a side view of a tissue modification device with vertically oriented blades, according to one embodiment of the present invention;

FIG. 25 is a perspective view of a flexible portion of a tissue modification device with vertically oriented blades, according to one embodiment of the present invention;

DETAILED DESCRIPTION OF THE INVENTION

Various embodiments of tissue modification devices and systems, as well as methods for making and using same, are provided. Although much of the following description and accompanying drawing figures generally focuses on surgical procedures in spine, in alternative embodiments, devices, systems and methods of the present invention may be used in any of a number of other anatomical locations in a patient's body. For example, in some embodiments, flexible tissue modification devices of the present invention may be used in minimally invasive procedures in the shoulder, elbow, wrist, hand, hip, knee, foot, ankle, other joints, or other anatomical locations in the body. Similarly, although some embodiments may be used to remove or otherwise modify ligamentum flavum and/or bone in a spine to treat spinal stenosis, in alternative embodiments, any of a number of other tissues may be modified to treat any of a number of other conditions. For example, in various embodiments, treated tissues may include but are not limited to ligament, tendon, bone, tumor, cyst, cartilage, scar, osteophyte, inflammatory tissue and the like. Non-target tissues may include neural tissue and/or neurovascular tissue in some embodiments or any of a number of other tissues and/or structures in other embodiments. In one alternative embodiment, for example, a flexible tissue modification device may be used to incise a transverse carpal ligament in a wrist while inhibiting damage to the median nerve, to perform a minimally invasive carpal tunnel release procedure. Thus, various embodiments described herein may be used to modify any of a number of different tissues, in any of a number of anatomical locations in the body, to treat any of a number of different conditions.

Figure 1:
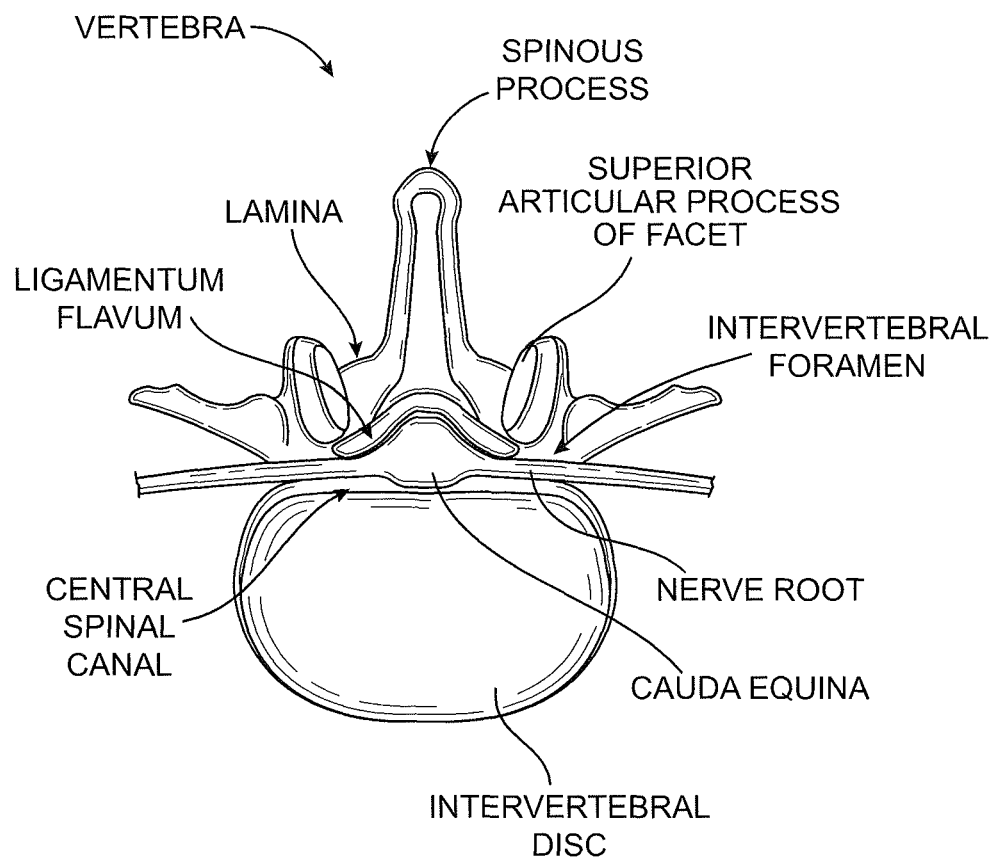
FIG. 1 is a top view of a vertebra with the cauda equina shown in cross section and two nerve roots branching from the cauda equina to exit the central spinal canal and extend through intervertebral foramina on either side of the vertebra.
Figure 2A:
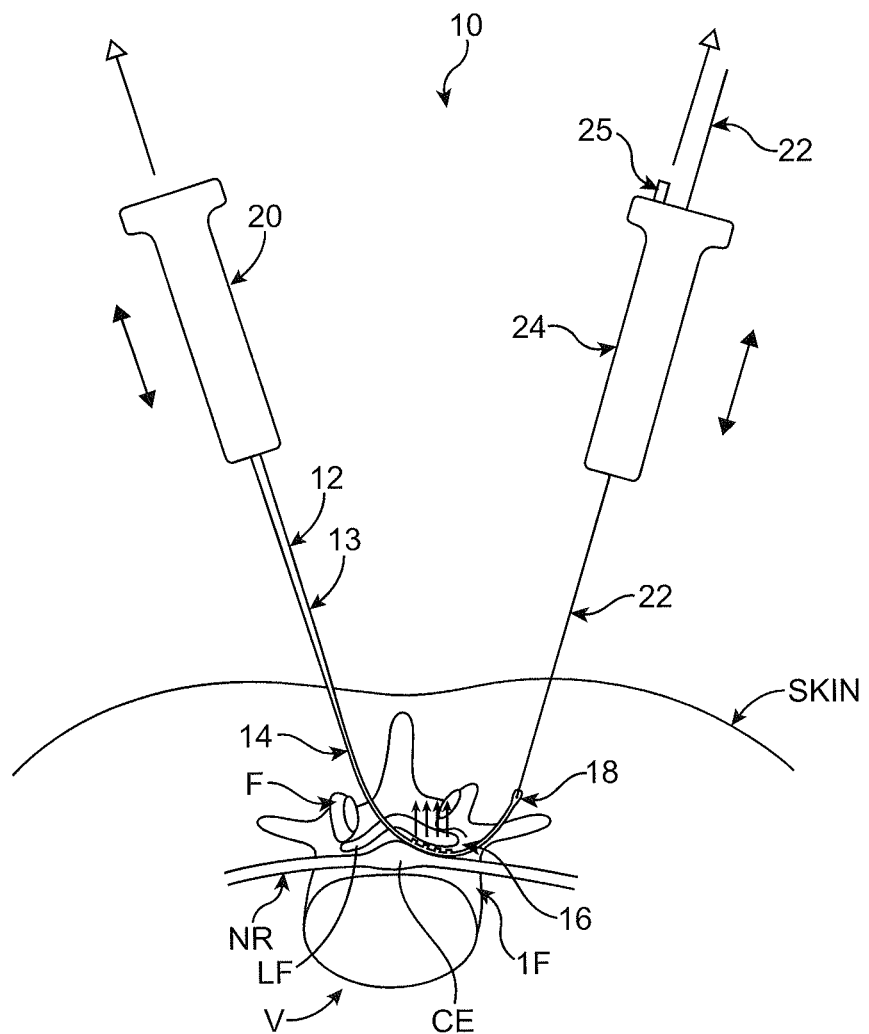
FIG. 2A is a cross-sectional view of a patient's back and a side view of a flexible tissue modification device in position in a spine, according to one embodiment of the present invention.

With reference now to FIG. 2A, a tissue modification device 10 according to one embodiment may suitably include a proximal handle 20 coupled with a shaft 12 having a proximal, rigid portion 13 and a distal, flexible portion 14 on which one or more tissue modifying members 16 may be disposed. A guidewire coupler 18 may be formed in (or attached to) flexible portion 14 at or near its distal end, for coupling with a guidewire 22, which in turn may be coupled with a guidewire handle 24 (or "distal handle"), which may include a tightening lever 25 for tightening handle 24 around guidewire 22.

Device 10 is shown percutaneously placed in position for performing a tissue modification procedure in a patient's spine, with various anatomical structures shown including a vertebra V, cauda equina CE, ligamentum flavum LF, nerve root NR, facet F, and intervertebral foramen IF. Various embodiments of device 10 may be used in the spine to remove ligamentum flavum LF, facet bone F, bony growths, or some combination thereof, to help decompress cauda equina CE and/or nerve root NR tissue and thus help treat spinal stenosis and/or neural or neurovascular impingement. Although this use of device 10 will not be continuously repeated for every embodiment below, any of the described embodiments may be used to remove ligamentum flavum alone, bone alone, or a combination of ligament and bone in the spine to treat neural impingement, neurovascular impingement and/or spinal stenosis.

In one embodiment of a method for modifying tissue using device 10, a distal end of 22 guidewire may be placed into the patient, along a curved path between target and non-target tissue, and out of the patient. A distal portion of guidewire 22 may then be coupled with guidewire handle 24, such as by passing guidewire 22 through a central bore in handle 24 and tightening handle 24 around guidewire 22 via tightening lever 25 or other tightening means. A proximal end of guidewire 22 may then be coupled with coupling member 18 and used to pull distal shaft portion 14 between target and non-target tissues. In some embodiments, device 10 may be advanced into the patient percutaneously, while in alternative embodiments, device 10 may be advanced through a small incision or larger incision. Once advanced into the patient, flexible distal shaft portion 14 may be advanced along a curved path between the target and non-target tissues, and in some instances may be pulled at least partway into an intervertebral foramen IF of the spine.

Proximal handle 20 and guidewire handle 24 may be pulled (or "tensioned"—solid/single-tipped arrows) to urge tissue modifying members 16 against the target tissue (in this case, ligamentum flavum LF). Generally, tissue modifying members 16 may be fixedly attached to (or formed in) one side or surface of distal portion 14, while an opposite side or portion of distal portion 14 faces non-target tissue, such as cauda equina CE and/or nerve root NR. The opposite side of distal portion 14 will generally be atraumatic and/or include an atraumatic cover, coating, shield, barrier, tissue capture member or the like. With tensioning force applied to device 10, handles 20, 24 may be used to reciprocate device 10 back and forth (solid/double-tipped arrows) to cause tissue modifying members 16 to cut, remove, shred or otherwise modify the target tissue. In various embodiments, for example, target tissue may include only ligamentum flavum LF, only bone, or a combination of both.

Reciprocation and tensioning may be continued until a desired amount of tissue is removed. Removed target tissue, in some embodiments, may be collected, captured or trapped between tissue modifying members 16 and/or in one or more tissue capture members or chambers (not shown). When a desired amount of target tissue has been removed, which may be determined, for example, by tactile feedback provided to the surgeon by device 10, by radiographic imaging, and/or by direct visualization (such as in an open surgical case), guidewire 22 may be released from distal handle 24, and device 10 may be removed from the patient's back. If desired, device 10 may be passed into the patient's spine again for additional tissue modification, and/or other devices may be passed into the spine.

Additional details of various methods for inserting and using device 10 are provided below. For further explanation of guidewire systems and methods for inserting devices to remove or otherwise modify tissue, reference may also be made to U.S. patent application Ser. No. 11/468,247 (now U.S. Pat. No. 7,857,813) and Ser. No. 11/468,252 (Publication No. US-2008-0086034-A1), both titled "Tissue Access Guidewire System and Method," and both filed Aug. 29, 2006, the full disclosures of which are herein incorporated by reference in their entirety.

Figure 2B:
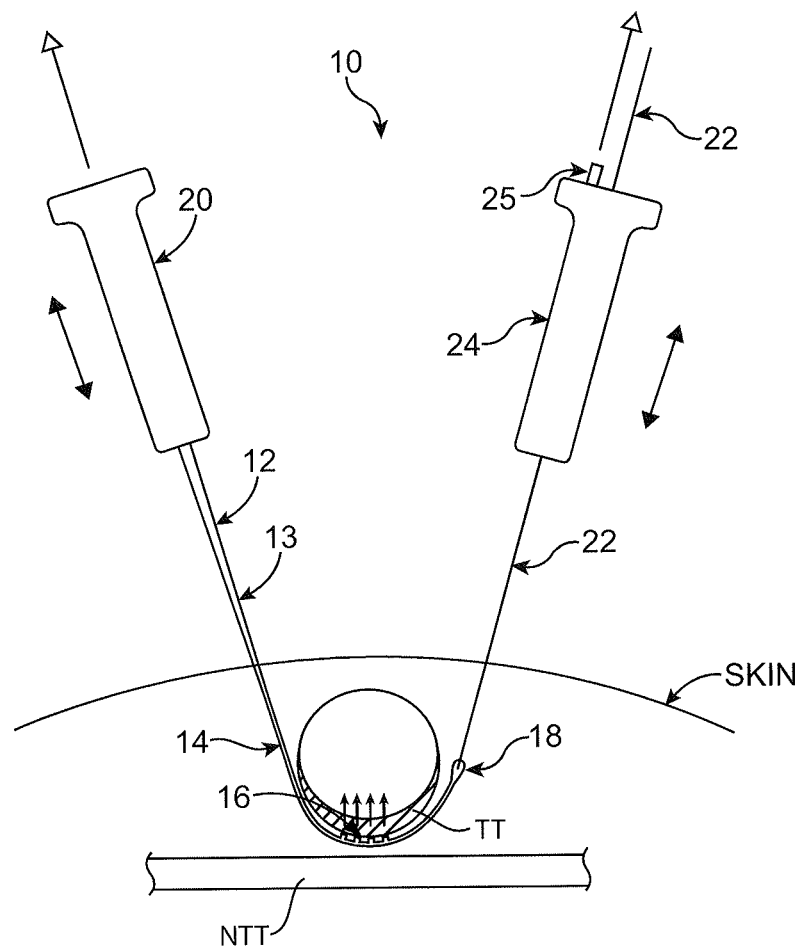
FIG. 2B is a diagrammatic view of a generic portion of a patient's body, showing target and non-target tissue, with the device of FIG. 2A in position to modify target tissue, according to one embodiment of the present invention.

Referring now to FIG. 2B, in various embodiments, device 10 may be used in parts of the body other than spine to remove target tissue TT while avoiding harm to non-target tissue NTT. For example, target tissue TT may include soft tissue adhering to bone, such as ligament and/or cartilage, and/or may include bone. Non-target tissue NTT may include any nervous tissue, vascular tissue, an organ, or any other tissue that a surgeon may desire to leave unharmed by a surgical procedure. In one embodiment, for example, device 10 may be used to perform a minimally invasive carpal tunnel release procedure by releasing the transverse carpal ligament without damaging the median nerve. In some embodiments, such a procedure may be performed percutaneously with or without an endoscope. In other embodiments, device 10 may be used to remove cartilage and/or ligament from a knee or shoulder in a minimally invasive procedure. In yet another embodiment, device 10 may be used to perform a minimally invasive bunionectomy. Therefore, although the following discussion focuses primarily on various uses of alternative embodiments of device 10 in spine, any of a number of other anatomical structures may be operated upon in different embodiments.

Figure 2C:
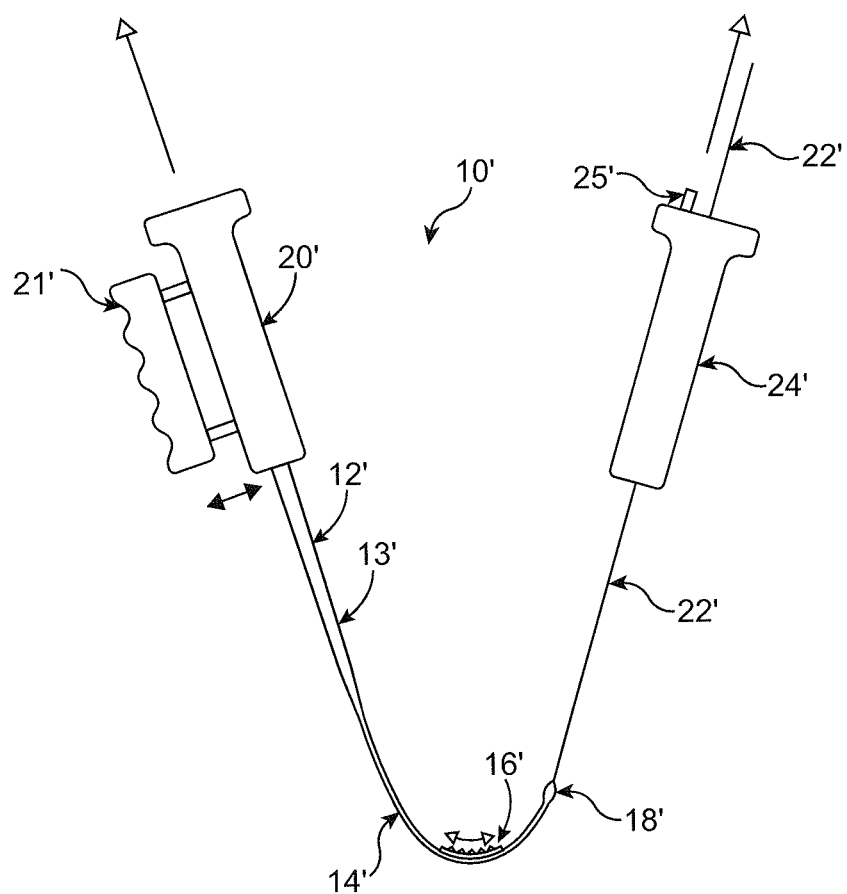
FIG. 2C is a side view of a tissue modification device, according to an alternative embodiment of the present invention.

Referring now to FIG. 2C, in an alternative embodiment, a tissue modification device 10' may suitably include a proximal handle 20', including a squeeze actuator 21' and coupled with a shaft 12' having a proximal, rigid portion 13' and a distal, flexible portion 14'. One or more tissue modifying members 16' may be moveably coupled with one side of flexible portion 14', and a guidewire coupler 18' may be formed in (or attached to) flexible portion 14' at or near its distal end, for coupling with a guidewire 22' and thus a distal handle 24' with a tightening lever 25'.

In this alternative embodiment, squeeze actuator 21' may be coupled with moveable tissue modifying members 16' by any suitable means, such that actuating actuator 21' (double-headed, solid-tipped arrow) causes tissue modifying members 16' to reciprocate back and forth (double-headed, hollow-tipped arrow). In use, therefore, device 10' as a whole may be held relatively stationary, while tissue modifying members 16' are reciprocated. Proximal handle 20' and rigid proximal shaft portion 13' may be used to steer device 10' relative to target tissue, and of course device 10' may be moved in and out of the patient and/or the target tissue, but it may also be possible to hold device 10' relatively stationary while reciprocating tissue modifying members 16'. In various embodiments, squeeze actuator 21' may be replaced with any suitable mechanical actuator, such as a trigger, lever or the like.

Figure 2D:
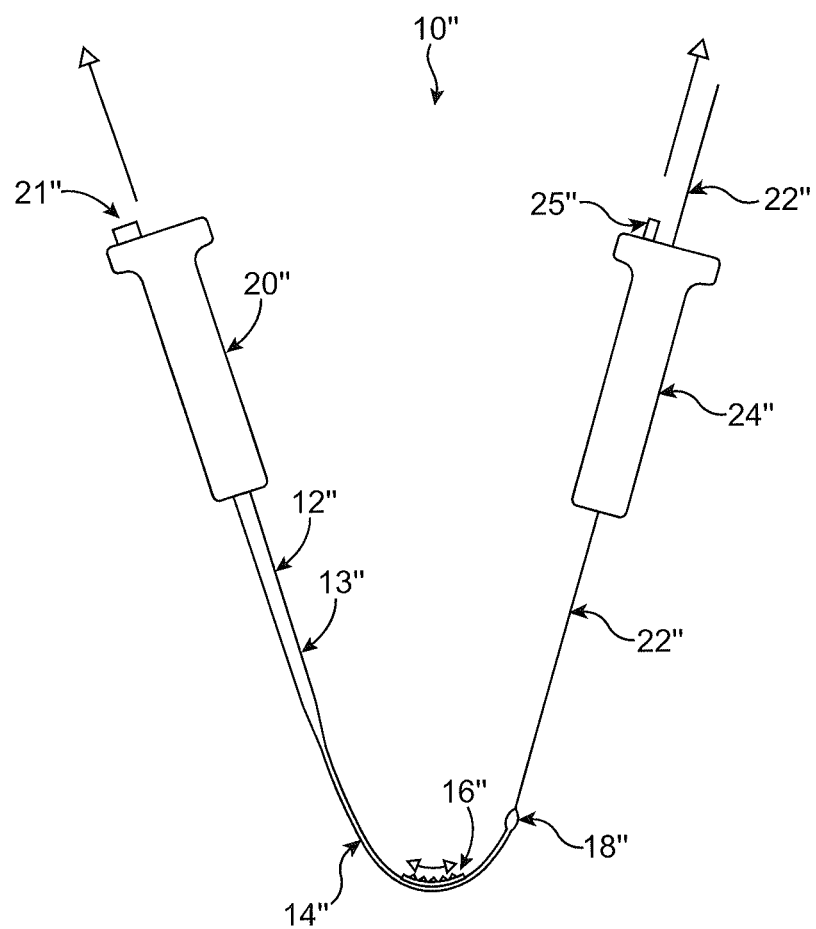
FIG. 2D is a side view of a tissue modification device, according to another alternative embodiment of the present invention.

With reference now to FIG. 2D, in another alternative embodiment, a tissue modification device 10" may be similar to the previous embodiment but may include, instead of squeeze actuator 21', a button actuator 21" and a powered drive mechanism within handle 20". Pressing button actuator 21" may activate tissue modifying members 16" to reciprocate back and forth to modify tissue. In various alternative embodiments, button 21" may be replaced with any suitable actuator, such as a trigger, switch, dial or the like.

Figure 3A:
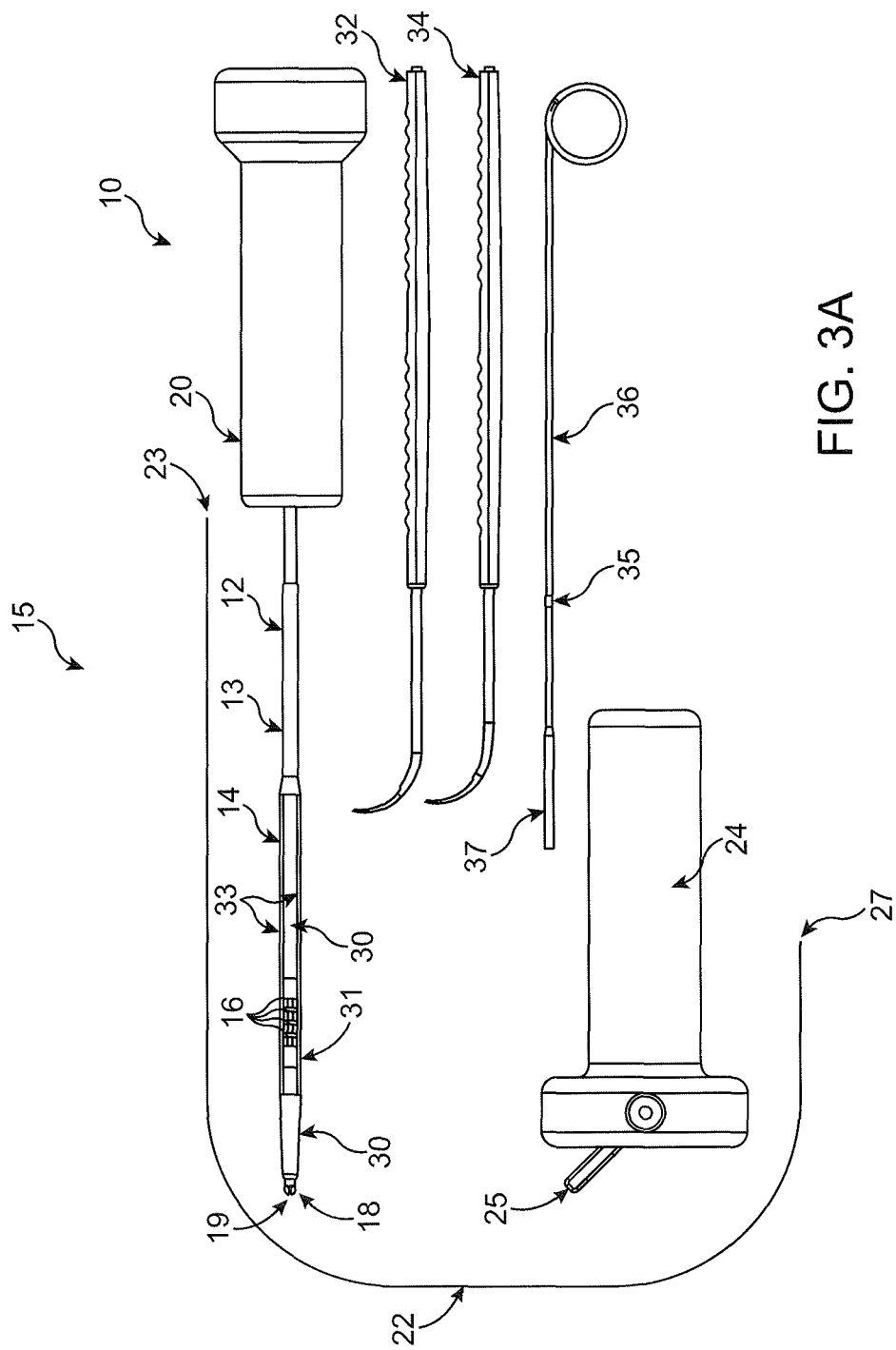
FIG. 3A is a view of a kit or system for modifying tissue, according to one embodiment of the present invention.

With reference now to FIG. 3A, in some embodiments tissue modification device 10 may be provided as a system (or "kit"), including the various components described above in reference to FIGS. 2A and 2B. In some embodiments, a tissue modification system 15 or kit may suitably include device 10 of FIGS. 2A and 2B, as well as one or more additional devices or components. For example, multiple guidewires 22 may be provided as part of system 15. In some embodiments, system 15 may also include one or more guidewire passage probes 32, 34 and a curved, flexible guide member 36. In one embodiment, for example, an ipsilateral access probe 32 and a contralateral access probe 34 may be provided. Curved guide member 36 is generally configured to pass through a lumen in each of probes 32, 34 and includes an inner lumen through which guidewire 22 may be passed. Guide member 36 may further include one or more depth marks 35 to indicate to a surgeon when guide member 36 has been passed a certain distance into probe 32, 34 and a stop 37 to limit passage of guide member 36 farther into probe 32, 34. In an alternative embodiment (not shown), such as might be used in a completely percutaneous procedure, probes 32, 34 may be replaced with an introducer needle, such as but not limited to a 14 gauge Touhy epidural needle or other size or type of epidural needle. In such an embodiment, guide member 36 may be designed to pass through the bore of the needle. For further description of various probe and guide member devices, reference may be made to U.S. patent application Ser. No. 11/468,247 (now U.S. Pat. No. 7,857,813) and Ser. No. 11/468,252 (Publication No. US-2008-0086034-A1). Further reference may be made to U.S. patent application Ser. No. 11/457,416, titled "Spinal Access and Neural Localization," and filed Jul. 13, 2006, now U.S. Pat. No. 7,578,819; and Ser. No. 60/823,594, titled "Surgical Probe and Method of Making," and filed Aug. 25, 2006, the full disclosures of which are herein incorporated by reference in their entirety.

Guidewire 22 may be made of any suitable material, such as nitinol or stainless steel, and may include a sharp distal tip 23, to facilitate passage of guidewire 22 through tissue, and a proximal shaped end 27 for coupling with guidewire coupler 18. Further details of various guidewire 22 embodiments and distal handle 24 are provided, for example, in U.S. patent application Ser. No. 11/468,247 (now U.S. Pat. No. 7,857, 813) and Ser. No. 11/468,252 (Publication No. US-2008-0086034-A1), which were previously incorporated by reference.

Figure 3B:
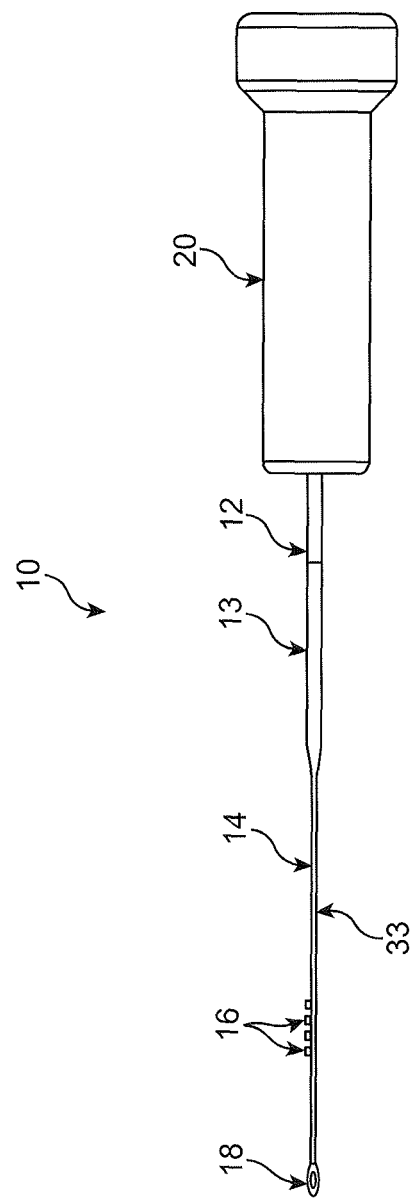
FIG. 3B is a side view of a portion of the kit of FIG. 3B.

FIGS. 3A and 3B show proximal handle 20 and shaft 12 in greater detail than in previous figures. In the embodiment shown, four tissue modifying members 16 are fixedly attached to one side of flexible distal shaft portion 14, each comprising grooved blades with bi-directional cutting edges. In various alternative embodiments, any number of tissue modifying members 16 may be included, such as from one to twenty tissue modifying members 16. Furthermore, tissue modifying members 16 may have any of a number of different configurations, some of which are described below, such as unidirectional blades, bi-directional blades, teeth, hooks, barbs, hooks, pieces of Gigli saw (or other wire saw), wires, meshes, woven material, knitted material, braided material, planes, graters, raised bumps, other abrasive surfaces, other abrasive materials, deliverable substances and/or the like.

In various embodiments, proximal shaft portion 13, distal shaft portion 14, tissue modifying members 16 and guidewire coupler 18 may be made of any suitable material (or materials), and may be made from one piece of material as a single extrusion or from separate pieces attached together. For example, in many embodiments, all of shaft 12 and guidewire coupler 18 may be made from one piece of material, and tissue modifying members 16 may be attached to distal shaft portion 14, such as by welding. In alternative embodiments, however, guidewire coupler 18 may be a separate piece attached to distal shaft portion 14 and/or tissue modifying members 16 may be formed in (rather than attached to) distal shaft portion 14. In yet another embodiment, distal shaft portion 14 may comprise a flat piece of material coupled with rigid proximal shaft portion 13, such as by welding. In some embodiments, shaft 12 may be formed from one piece of material, and distal shaft portion 14 may be flattened to derive its shape and flexibility. In some embodiments, one or more slits may be formed in distal shaft portion 14, to enhance its flexibility. In some embodiments, proximal shaft portion 13 may have a cylindrical shape. In some embodiments proximal shaft portion 13, distal shaft portion 14, or both may be hollow. Alternatively, any portion of shaft 12 may be solid in some embodiments, such as to give proximal shaft portion 13 added rigidity.

In one embodiment, guidewire coupler 18 may include a slot 19, shaped to receive and hold guidewire proximal shaped end 27. In various embodiments, slot 19 may be located on the top surface of distal shaft portion 14, as shown, or on the bottom surface. For further description of various embodiments of guidewire couplers, reference may be made to U.S. patent application Ser. Nos. 11/468,247 and 11/468, 252. In some embodiments, an atraumatic cover 30 may be disposed over part of distal shaft portion 14, forming atraumatic edges 33 and an aperture 31 through which tissue modifying members 16 protrude. Cover 30 may be made of any suitable atraumatic material, such as any of a number of different polymers. In some embodiments, cover 30 may also serve to collect cut tissue. Cover 30 may be made of any suitable material, such as a polymer, examples of which are provided below. In some embodiments, cover 30 may be made from a porous or semi-permeable material and/or one or multiple holes may be formed in cover 30 to allow fluid to pass through cover 30, thus allowing a greater amount of solid material to be packed into a tissue collection portion of cover 30.

FIG. 3B is a side view of device 10. Tissue modifying members 16 may be seen extending above atraumatic edges 33 of cover 30 and having cutting edges facing both proximally and distally. In alternative embodiments, tissue modifying members 16 may have only uni-directional cutting edges, such as facing only proximally or only distally. In the embodiment shown, guidewire coupler 18 is formed as a loop at the distal end of distal shaft portion 14. Guidewire shaped end 27 may generally fit into slot 19 (not visible in FIG. 3B) to reside within the loop of guidewire coupler 18 during use. In other embodiments, guidewire coupler 18 may comprise a separate piece attached to the top side or bottom side of distal shaft portion 14. Examples of such embodiments are described further in U.S. patent application Ser. No. 11/468,247 (now U.S. Pat. No. 7,857,813) and Ser. No. 11/468,252 (Publication No. US-2008-0086034-A1).

The various components of device 10, including proximal handle 20, shaft 12, tissue modifying members 16, guidewire coupler 18, and cover 30, may be fabricated from any suitable material or combination of materials. Suitable materials include, for example, metals, polymers, ceramics, or composites thereof. Suitable metals may include, but are not limited to, stainless steel (303, 304, 316, 316 L), nickel-titanium alloy, tungsten carbide alloy, or cobalt-chromium alloy, for example, Elgiloy® (Elgin Specialty Metals, Elgin, Ill., USA), Conichrome® (Carpenter Technology, Reading, Pa., USA), or Phynox® (Imphy SA, Paris, France). Suitable polymers include, but are not limited to, nylon, polyester, Dacron®, polyethylene, acetal, Delrin® (DuPont, Wilmington, Del.), polycarbonate, nylon, polyetheretherketone (PEEK), and polyetherketoneketone (PEKK). Ceramics may include, but are not limited to, aluminas, zirconias, and carbides. In some embodiments, one or more portions of shaft 12, for example, may be reinforced with carbon fiber, fiberglass or the like.

Referring now to FIGS. 4A-4E, one embodiment of a method for modifying tissue using flexible tissue modification device 10 is demonstrated in greater detail. In these figures, a patient's skin, target tissue TT and non-target tissue NTT are shown diagrammatically, rather than as specific structures. In one embodiment, the method of FIGS. 4A-4E may be employed in the spine, to remove ligamentum flavum, bone or both, with device 10 passing through an intervertebral foramen between two vertebrae, as shown in FIG. 2A. In other embodiments, other tissue in other areas of the body may be removed.

Figure 4A:
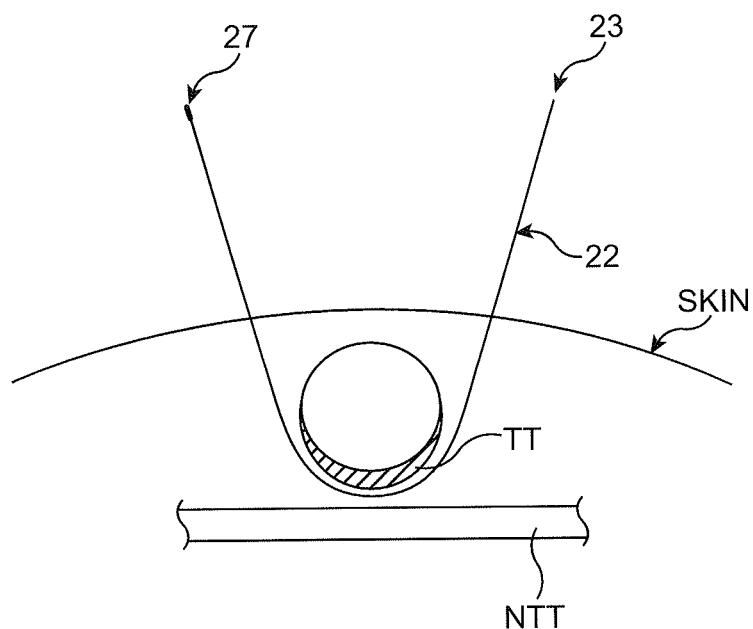
FIGS. 4A-4E demonstrate a method for inserting and using a flexible tissue modification device to modify tissue while inhibiting damage to non-target tissue, according to one embodiment of the present invention.

As shown in FIG. 4A, guidewire 22 with sharp tip 23 and shaped end 27 may be passed into the skin, between target and non-target tissue, and out of the skin. Methods for passing guidewire 22 are described further, for example, in U.S. patent application Ser. No. 11/457,416 (now U.S. Pat. No. 7,578,819), Ser. No. 11/468,247 (now U.S. Pat. No. 7,857,813) and Ser. No. 11/468,252 (Publication No. US-2008-0086034-A1), which were previously incorporated by reference. As described in those references, in various embodiments, guidewire 22 may be placed using a percutaneous method, such as with a needle, or using an open method, such as with a probe. In some embodiments, localization of neural tissue, such as with nerve stimulation on a guidewire passing probe or guidewire passing guide member may be used, to confirm that guidewire 22 is passed between target and non-target tissue.

In some embodiments where the method is performed in the spine, one or more substances or devices may be placed into the epidural space of the spine before or after placing guidewire 22, to create additional space between target tissues, such as ligamentum flavum, and non-target tissues, such as cauda equina and nerve root. Substances may include, for example, any of a number of fluids or gels, such as radiographic contrast medium. Devices may include, for example, a barrier or shield device. Injection of substances into the epidural space to create a safety zone is described in U.S. patent application Ser. No. 11/193,557 (Publication No. 2006/0036211), titled "Spinal Ligament Modification Kit," assigned to X-Sten, Inc., and filed Jul. 29, 2005, the full disclosure of which is hereby incorporated by reference. Various barrier devices for placement in the spine are described, for example, in U.S. patent application Ser. No. 11/405,859, titled "Tissue Modification Barrier Devices and Methods," and filed Apr. 17, 2005, Publication No. US-2007-0213734-A1, the full disclosure of which is herein incorporated by reference in its entirety.

Figure 4B:
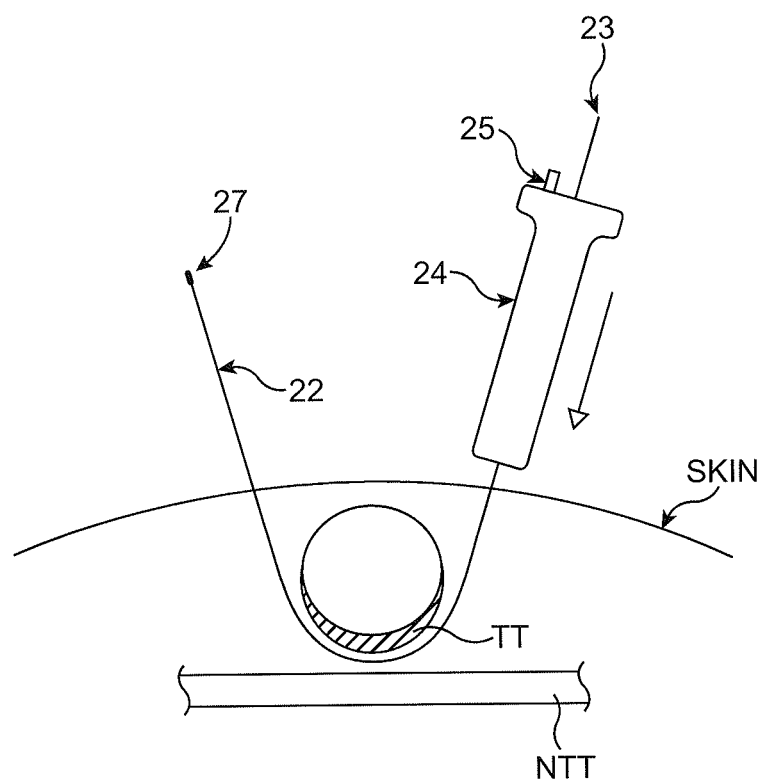

Referring to FIG. 4B, distal handle 24 may be passed over sharp tip 23 and tightened around guidewire 22, such as by moving tightening lever 25. Distal handle 24 may be coupled with guidewire 22 at this point in the process or at a later point, according to various embodiments.

Figure 4C:
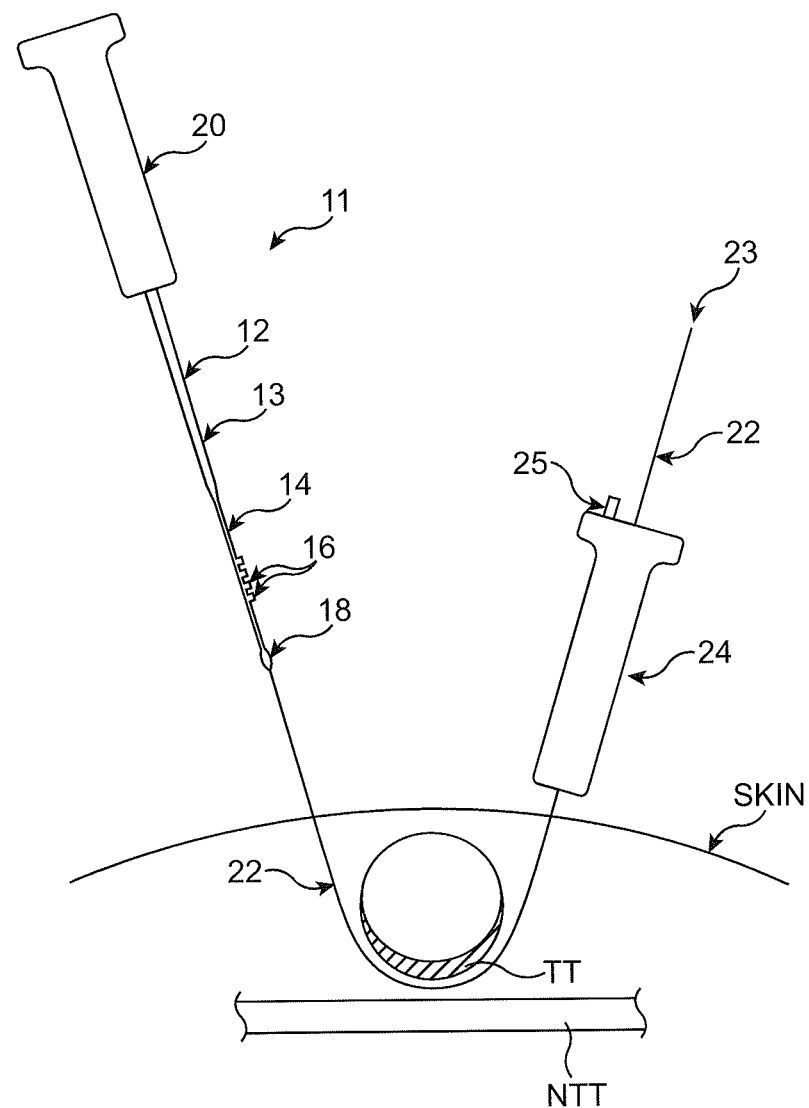

As shown in FIG. 4C, guidewire 22 may next be coupled with proximal device portion 11, by coupling shaped guidewire end 27 (not visible) with guidewire coupler 18. In the embodiment shown, for example, guidewire shaped end 27 may be placed into coupling member 18 (hollow-tipped arrow).

Figure 4D:
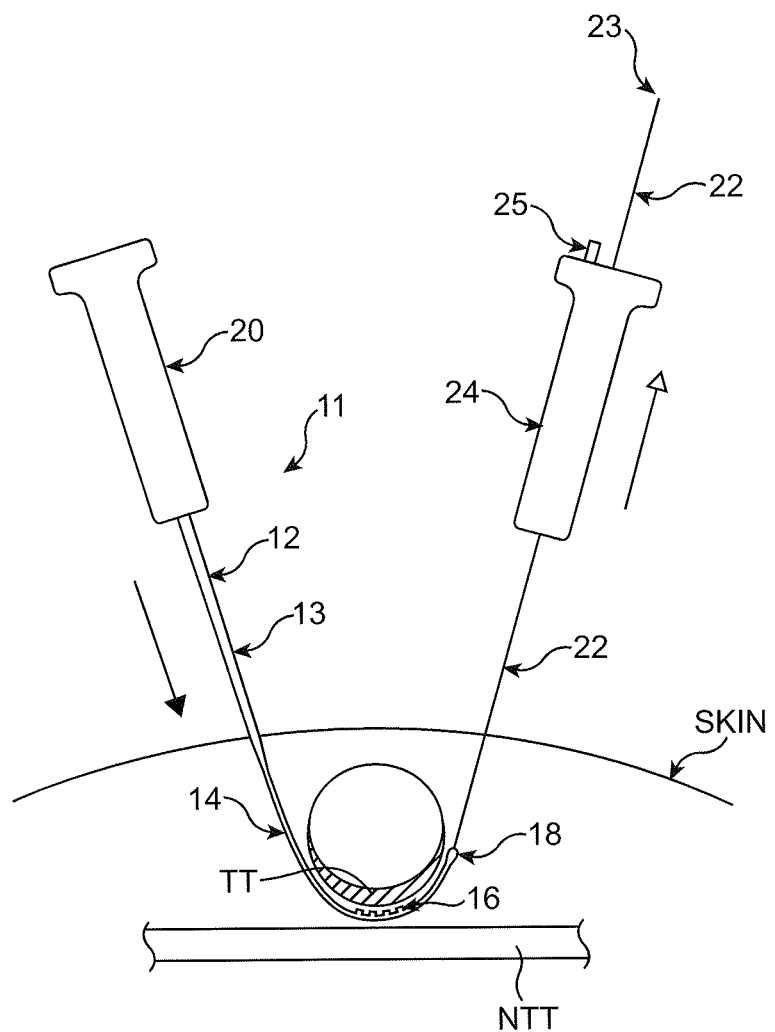

Referring to FIG. 4D, distal handle 24 may then be pulled (hollow-tipped arrow) to pull device 10 into the patient and to thus position tissue modifying members 16 in contact with target tissue TT. In some embodiments, such as when device 10 is used in a spinal procedure and passes through an intervertebral foramen, a surgeon or other physician user may use tactile feedback of device 10 passing into the foramen, such as when coupling member 18 and/or tissue modifying members 16 pass into the foramen, to determine when tissue modifying members 16 are positioned in a desired location relative to target tissue TT. Alternatively or additionally, a surgeon may confirm that a desired placement has been achieved by using radiographic imaging, such as fluoroscopy, direct visualization, such as in an open surgical case, or a combination of multiple methods.

In some embodiments in which device 10 is used in the spine to treat spinal stenosis and/or neural or neurovascular impingement, device 10 may be passed into the patient and to a position for modifying tissue without removing any vertebral bone. More specifically, in some embodiments, device 10 may be advanced into the patient, through an intervertebral foramen, and out of the patient without removing bone. This is contrary to the majority of current surgical methods for treating spinal stenosis, which typically include removal of at least some vertebral bone, such as performing a laminotomy or laminectomy, and which often remove significant amounts of vertebral lamina, spinous process, facet and/or pedicle bony tissue, simply to access the surgical site. In one embodiment, for example, device 10 may be advanced percutaneously into the patient, used to remove ligamentum flavum only, and withdrawn from the patient, without removing any vertebral bone.

Figure 4E:
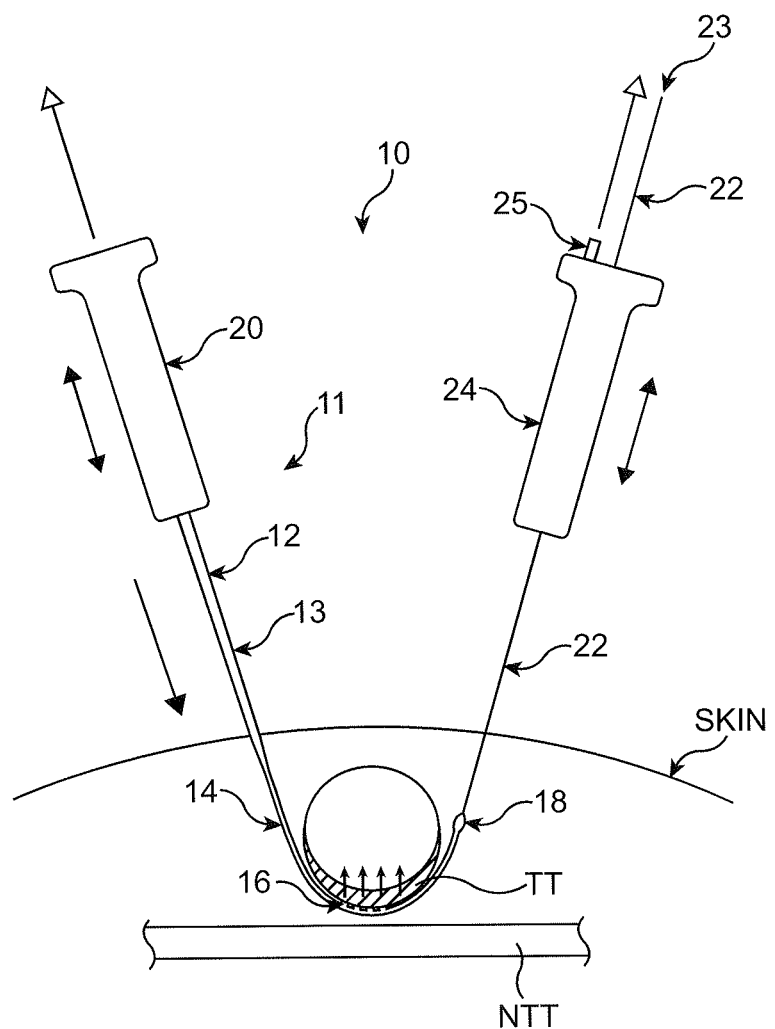

As shown in FIG. 4E, once tissue modifying members 16 are positioned as desired, relative to target tissue TT, proximal handle 20 and guidewire handle 24 may be pulled (hollow-tipped arrows) to urge tissue modifying members 16 against target tissue TT (solid-tipped, single-headed arrows). While maintaining pulling/tensioning force, handles 20, 24 may be used to reciprocate device 10 back and forth (solid-tipped, double-headed arrows) to remove target tissue TT. During a procedure, rigid proximal shaft portion 13 may be used to help steer device 10, or more specifically flexible distal shaft portion 14, relative to the target TT. For example, rigid shaft portion 13 may be used to move flexible portion 14 laterally or to pivot shaft 12 about an axis located along flexible portion 14. In one embodiment, for example, rigid portion 13 may be used to manipulate flexible portion 14 within an intervertebral foramen, such as by pivoting shaft 12 or moving flexible portion 14 laterally in a caudal and/or cephalad direction, relative to the patient. The rigidity of rigid proximal shaft portion 13 may generally facilitate such steering, as compared to a completely flexible device.

When a desired amount of tissue is removed, device 10 may be removed from the patient, such as by detaching guidewire handle 24 from guidewire 22 and pulling proximal handle 20 to withdraw device 10 and guidewire 22 out of the patient. In some embodiments, device 10 or an additional device may be reinserted into the patient and used in a second location to remove additional tissue. For example, in a spinal stenosis treatment procedure, device 10 may be used to remove tissue from (and thus decompress) a first intervertebral foramen and then may be removed and reinserted to remove tissue from a second foramen. This process may be repeated to remove tissue from any number of foramina. In one embodiment, device 10 may include a guidewire lumen, so that a guidewire may be placed into a second foramen while device 10 is in the epidural space of the patient. Device 10 may then be removed along with the first guidewire 22, attached to the second guidewire, and reinserted into the second foramen to remove tissue. In some embodiments, tissue may be removed from device 10 before reinserting device 10 into the patient to remove more tissue.

Figure 5A:
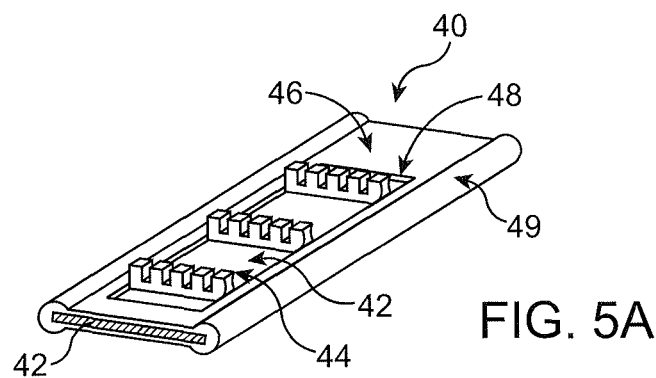
FIG. 5A is a perspective view of a flexible portion of a tissue modification device, according to one embodiment of the present invention.
Figure 5B:
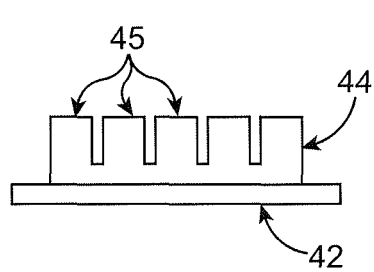
FIGS. 5B and 5C are end-on and side views of blade and substrate portions of the portion of the device of FIG. 5A.
Figure 5C:
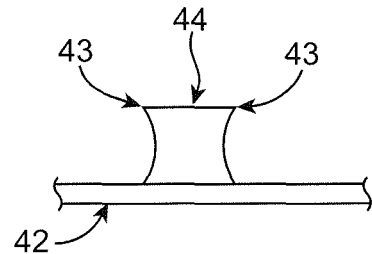

Referring now to FIGS. 5A-5C, a flexible distal portion 40 of a flexible tissue modification device is shown, in various views. In FIGS. 5A-5C and 6-25, various alternative embodiments of a flexible distal portion of a tissue modification device are shown in a generally straight configuration. However, all embodiments shown are flexible and thus may assume a curved configuration. The embodiments are shown in straight configuration for ease of illustration only.

In one embodiment, flexible distal portion 40 may include a substrate 42 (or "flexible, distal shaft portion"), multiple tissue modifying members 44 coupled with substrate 42, and an atraumatic cover 46 disposed over substrate 42 and forming an aperture 48 and atraumatic bumpers 49. FIG. 5B is an end-on view of substrate 42 and one of cutting members 44, which includes multiple teeth 45. FIG. 5C is a side view of substrate 42 and one of cutting members 44, showing that each cutting member 44 has two cutting edges 43 in this embodiment.

The embodiment of FIG. 5A includes three cutting members 44 comprising blades with multiple teeth 45 with grooves between them. Cutting members 44 in this and other embodiments may include any suitable material, such as but not limited to stainless steel or any of the materials listed previously above. Any number of cutting members 44 may be used, such as from one to twenty cutting members in various embodiments. Cutting members 44 may have any suitable height and may be spaced apart from one another at any suitable distances. In one embodiment, for example, cutting members 44 may have a height designed to protrude just slightly above the height of bumpers 49, so that cutting members 44 can cut tissue but do not protrude so high as to inhibit advancement or positioning of device in the patient. In some embodiments, cutting members 44 may be constructed as separate pieces and attached to substrate 42, such as by welding or gluing with adhesive. In some embodiments, cutting members 44 may be built by stacking layers of material to one another and attaching the stacks to form one piece. Cover 46 may be coupled with substrate using any known or later invented manufacturing technique, such as thermoforming, injection molding or the like.

In various alternative embodiments of distal portion 40 of FIGS. 5A-5C, as well as in all embodiments described below and alternatives thereto, any number of cutting members 44 may be used, cutting members 44 may be made of any suitable material, and cutting members may be disposed along substrate 42 in any configuration, pattern or the like. Therefore, various alternative materials, numbers, patterns and the like of cutting members 44 will not be listed repeatedly for each alternative embodiment.

Figure 6:
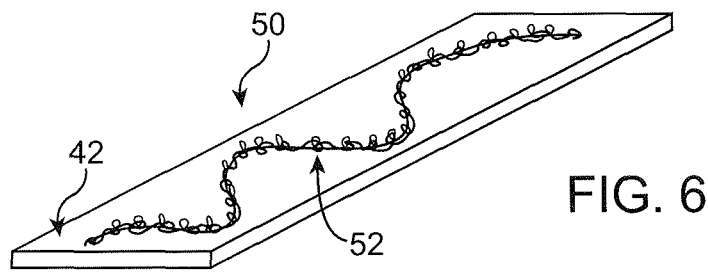
FIG. 6 is a perspective view of a portion of a flexible substrate and a wire saw tissue modifying member of a tissue modification device, according to one embodiment of the present invention.

Referring now to FIG. 6, in another embodiment, a distal portion of a flexible tissue modification device 50 may include substrate 42 and a wire saw 52 coupled with substrate 42, such as by welding. In FIG. 6, as well as in subsequent FIGS. 7-22, only a portion of each device embodiment including substrate 42 and one or more cutting members is shown, to simplify the drawing figures and description. Any of these embodiments may also include an atraumatic cover and/or other features, but for simplicity's sake, these features are not shown. Referring to the embodiment of FIG. 6, wire saw 52 may comprise any wire saw currently known or later invented, such as a Gigli saw, and may be attached to substrate 42 in any suitable pattern or configuration, such as in an S-shape pattern, as shown, or a zig-zag, straight-line or other pattern.

Figure 7:
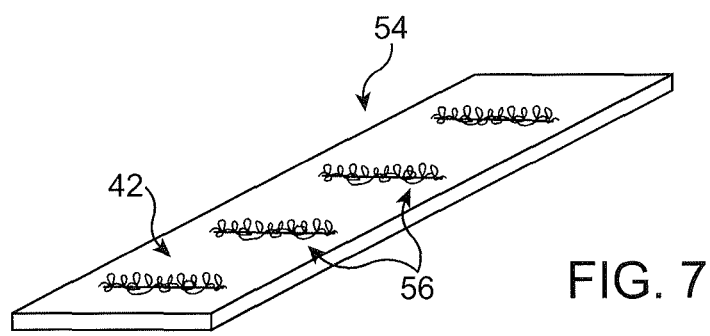
FIG. 7 is a perspective view of a portion of a flexible substrate and multiple wire saw tissue modifying members of a tissue modification device, according to an alternative embodiment of the present invention.

With reference to FIG. 7, in an alternative embodiment, a distal portion of a flexible tissue modification device 54 may include multiple pieces of wire saw 56 coupled with substrate 42. Again, these pieces of saw 56 may be attached in any pattern and by any means, such as by welding, and may comprise Gigli saw or other types of wire saw.

Figure 8:
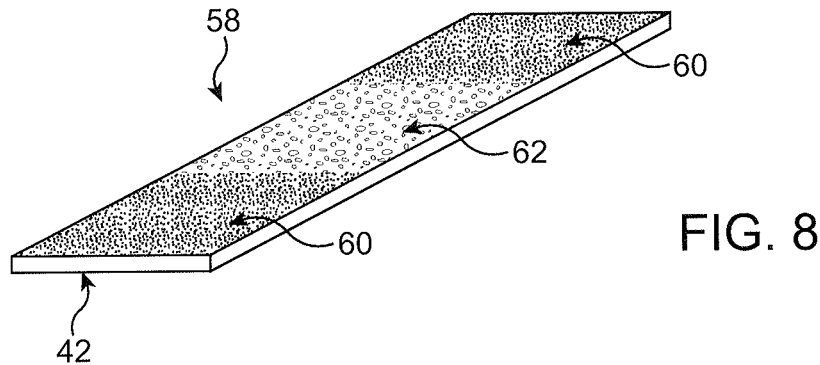
FIG. 8 is a perspective view of a portion of a flexible substrate and an abrasive surface tissue modifying member of a tissue modification device, according to an alternative embodiment of the present invention.

FIG. 8 shows a portion of another alternative embodiment of a flexible tissue modification device 58, in which abrasive materials 60, 62 are adhered to a surface of substrate. In some embodiments, only one type and/or grain of abrasive material 60 or 62 may be used, while other embodiments may include multiple types of material, multiple grains of material, or both. For example, in the embodiment shown, a finer grain of material 60 may be disposed at either end of a portion of coarser grain material 62. Such a variation in grains may provide varying degrees of tissue modification and/or the ability to remove greater amounts of tissue with a coarser grain 62 and provide a smoother finished surface to the tissue with the finer grain 60. In various embodiments, any abrasive materials 60, 62 may be used, and the materials may be adhered to substrate 42 via any method, such as adhering with adhesive or the like. One embodiment, for example, may include abrasive materials such as those described in U.S. patent application Ser. No. 10/277,776 (Publication No. 2003/0225412), titled "Surgical Ribbon File," and filed Oct. 21, 2002, the full disclosure of which is hereby incorporated by reference. In another embodiment, substrate 42 may be treated in such a way as to have an abrasive surface, such as by sand blasting.

Figure 9:
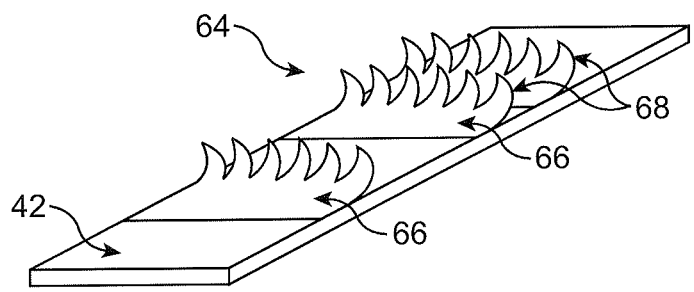
FIG. 9 is a perspective view of a portion of a flexible substrate and multiple tooth-like tissue modifying members of a tissue modification device, according to an alternative embodiment of the present invention.

Referring to FIG. 9, in another alternative embodiment, a flexible tissue modification device 64 may include multiple tissue modifying members 66, each including multiple, curved teeth 68. Cutting members 66 may be made of stainless steel or other material(s). In some embodiments, cutting members 66 may be configured to primarily cut and/or shred ligamentous tissue, such as ligamentum flavum.

Figure 10:
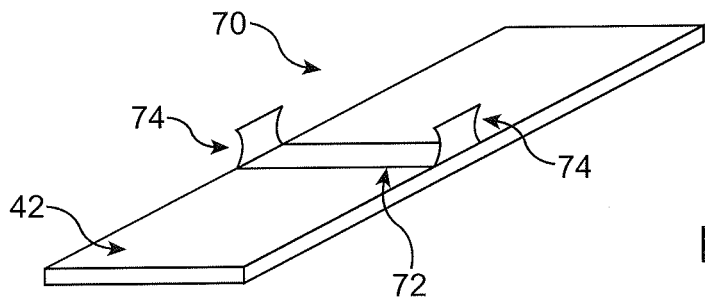
FIG. 10 is a perspective view of a portion of a flexible substrate and a two-blade tissue modifying member of a tissue modification device, according to an alternative embodiment of the present invention.

Referring to FIG. 10, in another alternative embodiment, a flexible tissue modification device 70 may include one or more tissue modifying members 72 coupled with a first major surface of a flexible substrate 42. Each tissue modifying member 72 may include a base 73 disposed between two blades 74, with a bend between base 73 and each blade 74. As will be described in greater detail below, each blade 74 may have a first end coupled with substrate 42 via base 73 and may extend to a second, cantilevered end. In some embodiments, each blade 74 may be substantially in-line (i.e., a side of blade 74 oriented at between about 0 degrees and about 45 degrees relative to a longitudinal axis of substrate 42) and may also be substantially vertical (i.e., a side of blade 74 forms an angle with the plane of substrate 42 of between about 45 degrees and about 90 degrees). Blades 74 may have any of a number of shapes, heights, lengths and the like, a number of embodiments of which will be described below. For example, blades 74 may be designed, in one embodiment, specifically for cutting or slicing ligamentous tissue, such as ligamentum flavum.

Figure 11:
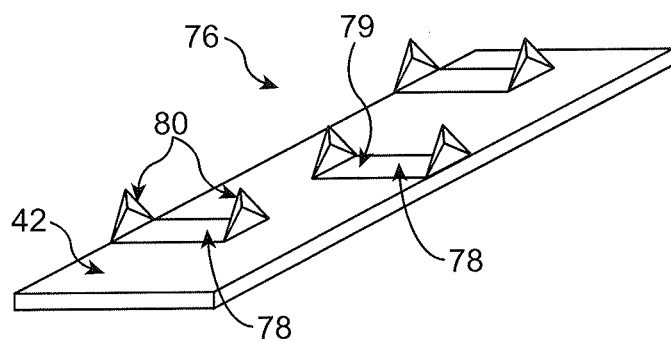
FIG. 11 is a perspective view of a portion of a flexible substrate and multiple shark-tooth-shaped tissue modifying members of a tissue modification device, according to an alternative embodiment of the present invention.

Referring to FIG. 11, in another alternative embodiment, a flexible tissue modification device 76 may include multiple, laterally offset tissue modifying members 78 disposed laterally across a first major surface of a substrate flexible portion 42. In one embodiment, for example, each tissue modifying member 78 may include a base 79 with two substantially vertical blades 80 disposed at its opposite ends. Any suitable number of tissue modifying members 78 may be used in a given embodiment, such as but not limited to between two members 78 (four blades 78) and eight members 78 (16 blades 78), in alternative embodiments. Blades 80 may each have a triangular or "shark-tooth" shape, with two sharp cutting edges and a pointed cantilevered tip. In alternative embodiments, any of a number of other blade configurations may be used, some of which are described in greater detail below. In one embodiment, blades 80 may be designed specifically for cutting or slicing ligamentous tissue, such as ligamentum flavum. Alternatively, or additionally, blades 80 may be configured to cut bone. In one embodiment, each blade 80 may have a height approximately equal to or greater than a thickness of a ligamentum flavum. Such a blade 80 may be positioned in the spine to extend through ligamentum flavum and contact bone. When reciprocated, such a blade 80 may cut ligamentum flavum alone or may cut ligamentum flavum tissue and then, when it is removed, may also cut bone. Such a blade height and configuration may facilitate lateral steering of device 76. Various alternative embodiments of tissue modification devices having vertically oriented blades are described in greater detail below, with reference to FIGS. 23-60.

Figure 12:
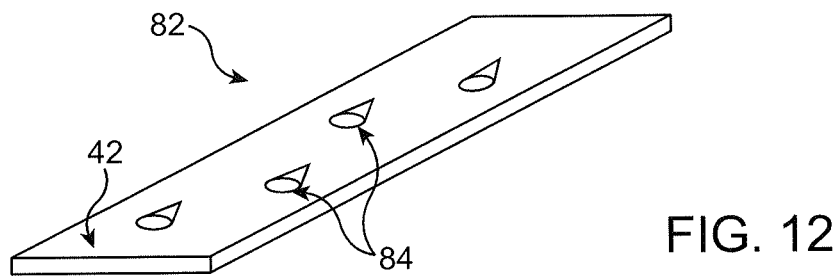
FIG. 12 is a perspective view of a portion of a flexible substrate and multiple cheese-grater-shaped tissue modifying members of a tissue modification device, according to an alternative embodiment of the present invention.

Referring to FIG. 12, in another alternative embodiment, a flexible tissue modification device 82 may include multiple tissue modifying members 84 formed as holes in substrate 42 with raised edges, such as are found on a cheese grater. The raised edges of cutting members 84 may be sharp, to provide cutting. Any number of tissue modifying members 84 may be included, they may have any desired size, and they may be formed on substrate in any pattern. In some embodiments, cut tissue may pass through the holes of cutting members 84 and thus through substrate 42. In some embodiments, a tissue capture device or member may be coupled with the back side of substrate 42 to collect cut tissue that passes through cutting members 84.

Figure 13:
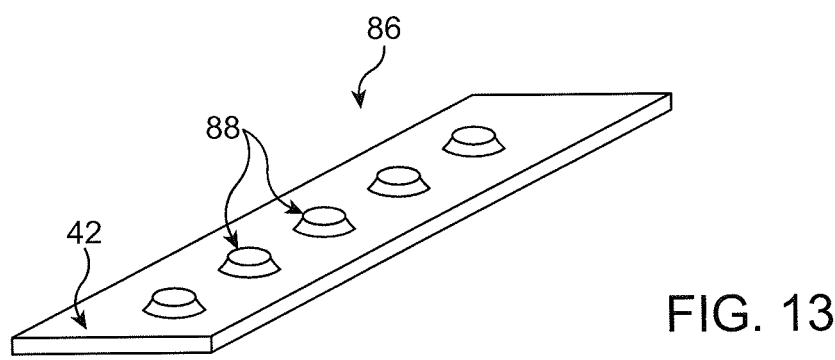
FIG. 13 is a perspective view of a portion of a flexible substrate and multiple raised tissue modifying members of a tissue modification device, according to an alternative embodiment of the present invention.

Referring to FIG. 13, in another alternative embodiment, a flexible tissue modification device 86 may include multiple tissue modifying members 88 formed as upward-facing holes in substrate 42. The raised edges of cutting members 88 may be sharpened, to provide cutting. Any number of tissue modifying members 88 may be included. In some embodiments, cut tissue may pass through the holes of cutting members 88 and thus through substrate 42. In some embodiments, a tissue capture device or member may be coupled with the back side of substrate to collect cut tissue that passes through cutting members 88.

Figure 14:
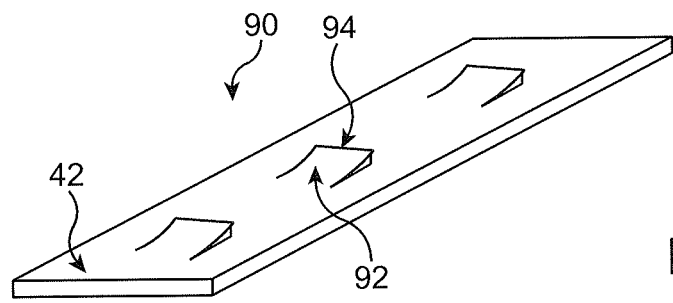
FIG. 14 is a perspective view of a portion of a flexible substrate and multiple raised-flap tissue modifying members of a tissue modification device, according to an alternative embodiment of the present invention.

Referring to FIG. 14, in another alternative embodiment, a flexible tissue modification device 90 may include multiple tissue modifying members 92 formed as raised flaps in substrate 42, with each flap 92 including a sharpened cutting edge 94. Any number of tissue modifying members 92 may be included. In some embodiments, cut tissue may pass underneath the flap-like cutting members 92 and thus through substrate 42. In some embodiments, a tissue capture device or member may be coupled with the back side of substrate to collect cut tissue that passes through cutting members 92.

Figure 15:
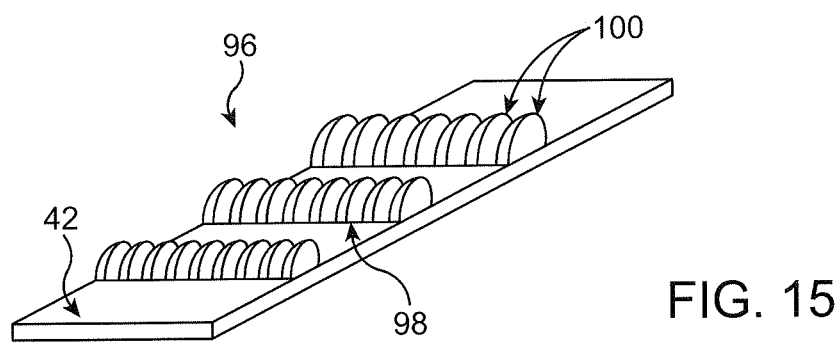
FIG. 15 is a perspective view of a portion of a flexible substrate and multiple rounded tissue modifying members of a tissue modification device, according to an alternative embodiment of the present invention.

Referring to FIG. 15, in another alternative embodiment, a flexible tissue modification device 96 may include multiple tissue modifying members 98 formed as rounded cutting devices coupled with substrate 42. In one embodiment, each cutting member 98 may include multiple ridges, divided by grooves. In one embodiment, cutting members 98 may have a spiral or screw-like configuration.

Figure 16:
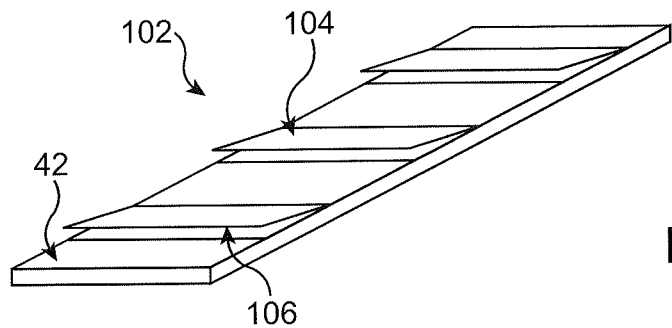
FIG. 16 is a perspective view of a portion of a flexible substrate and multiple raised-flap tissue modifying members of a tissue modification device, according to an alternative embodiment of the present invention.

Referring to FIG. 16, in another alternative embodiment, a flexible tissue modification device 102 may include multiple tissue modifying members 104 comprising thin, flap-like blades coupled with substrate 42, each cutting member 104 including a sharp blade edge 106. Any number, size and configuration of blades may be used.

Figure 17:
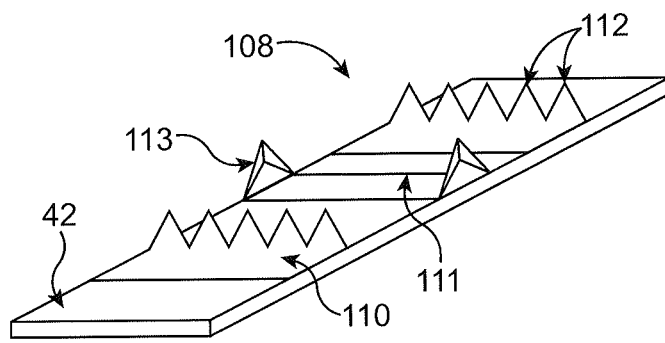
FIG. 17 is a perspective view of a portion of a flexible substrate and multiple, differently shaped tissue modifying members of a tissue modification device, according to an alternative embodiment of the present invention.

Referring to FIG. 17, in another alternative embodiment, a flexible tissue modification device 108 may include multiple different types of tissue modifying members 110, 111. For example, one embodiment may include one or more jagged tissue cutters 110 each having multiple, triangular, raised teeth 112, and one or more bladed tissue cutters 111, each having multiple blades 113. Teeth 112 and/or blades 113 may be configured specifically to cut ligamentum flavum tissue, bone, or both, in various embodiments.

Figure 18:
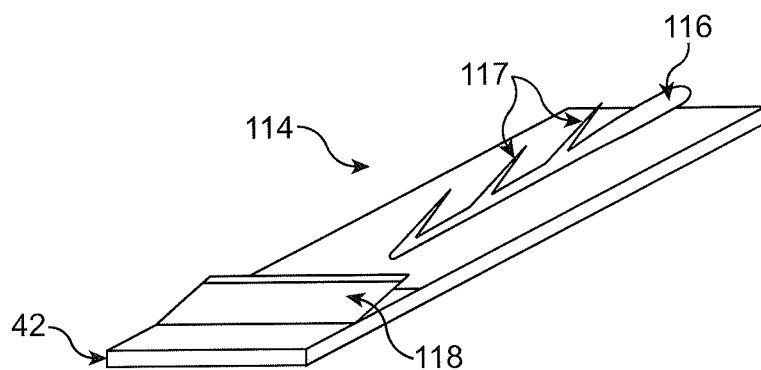
FIG. 18 is a perspective view of a portion of a flexible substrate and barbed-hook and raised-flap tissue modifying members of a tissue modification device, according to an alternative embodiment of the present invention.

Referring to FIG. 18, in another alternative embodiment, a flexible tissue modification device 114 may include substrate 42, a tissue engaging member 116 including multiple barbs 117 (or hooks, needles or the like), and one or more tissue cutting members 118, such as a raised blade. In various embodiments, tissue engaging member 116 may be configured to hook, snag, grab or otherwise engage soft tissue, such as ligamentum flavum, and pull or stretch such tissue as it is pulled or pushed across the tissue. Tissue cutting member 118 may follow behind tissue engaging member 116 and cut the stretched/pulled tissue. Such stretching or pulling of tissue before cutting may facilitate or enhance tissue cutting.

Figure 19:
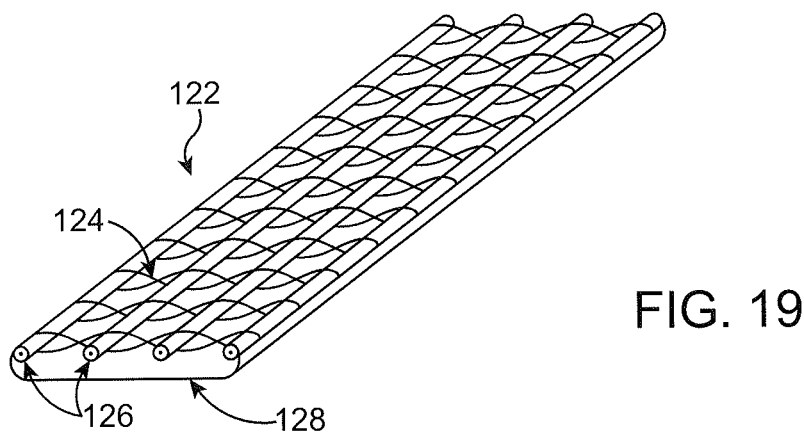
FIG. 19 is a perspective view of a portion of a wire mesh flexible tissue modification device, according to an alternative embodiment of the present invention.

Referring to FIG. 19, in another alternative embodiment, a flexible tissue modification device 122 may include a wire mesh 124 coupled with multiple supporting structures 126 and an atraumatic material 128 on one side. All components may be made of any suitable material, such as those listed previously.

Figure 20:
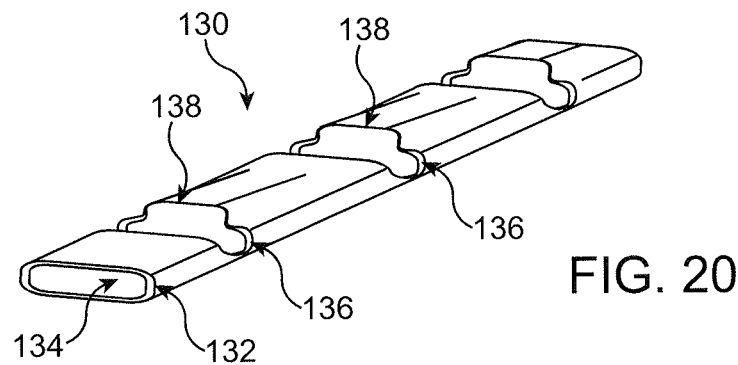
FIG. 20 is a perspective view of a portion of a flattened, hollow, flexible tissue modification device, according to an alternative embodiment of the present invention.

Referring to FIG. 20, in another alternative embodiment, a flexible tissue modification device 130 may comprise a hollow, flattened shaft 132, having central chamber or lumen 134, into which multiple grooves 136 may be cut. An edge of each groove 136 may be raised and sharpened to form a blade edge 138, thus forming a multiple, bladed tissue modifying members. Tissue cut by blades 138 may pass under blades 138 to collect within lumen 134 and may thus be transported out of the patient.

Figure 21:
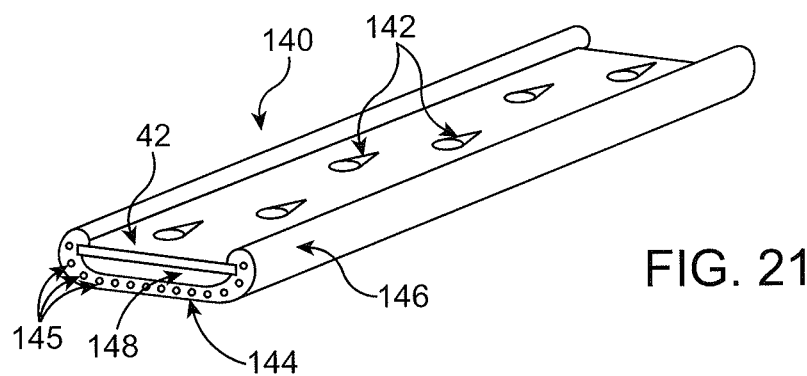
FIG. 21 is a perspective view of a portion of a flexible substrate and cheese-grater-shaped tissue modifying members coupled with a tissue capture member of a tissue modification device, according to an alternative embodiment of the present invention.

Referring to FIG. 21, in another alternative embodiment, a flexible tissue modification device 140 may include multiple tissue modifying members 142 formed as holes in substrate 42 with raised edges, such as are found on a cheese grater. The raised edges of cutting members 142 may be sharpened, to provide cutting. Any number of tissue modifying members 142 may be included. In some embodiments, cut tissue may pass through the holes of cutting members 142 and thus through substrate 42. In some embodiments, a tissue collection member 144, forming a tissue collection chamber 148, may be coupled with the back side of substrate 42 to collect cut tissue that passes through cutting members 142. Tissue collection member 144 may also serve as an atraumatic tissue protection member and may include, for example, side bumpers 146 to avoid damaging non-target tissue with sharp edges of device 140. In some embodiments, tissue collection member 144 may be strengthened by multiple fibers 145, such as wires or carbon fibers.

Figure 22:
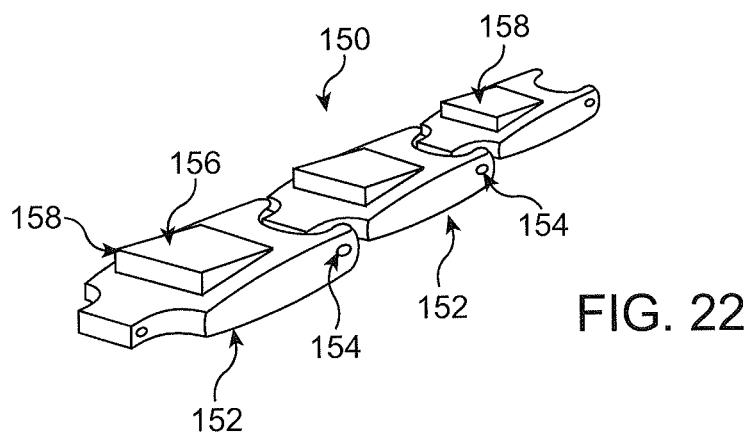
FIG. 22 is a perspective view of a portion of a moveable-link flexible tissue modification device, according to an alternative embodiment of the present invention.

Referring to FIG. 22, in another alternative embodiment, a flexible tissue modification device 150 may include multiple sections 152 linked together via linkages 154 to form a flexible device configuration analogous to that of some watch bands. A tissue modifying member 156 having a cutting edge 158 may be disposed on one side of each section 152 to cut tissue.

Figure 23:
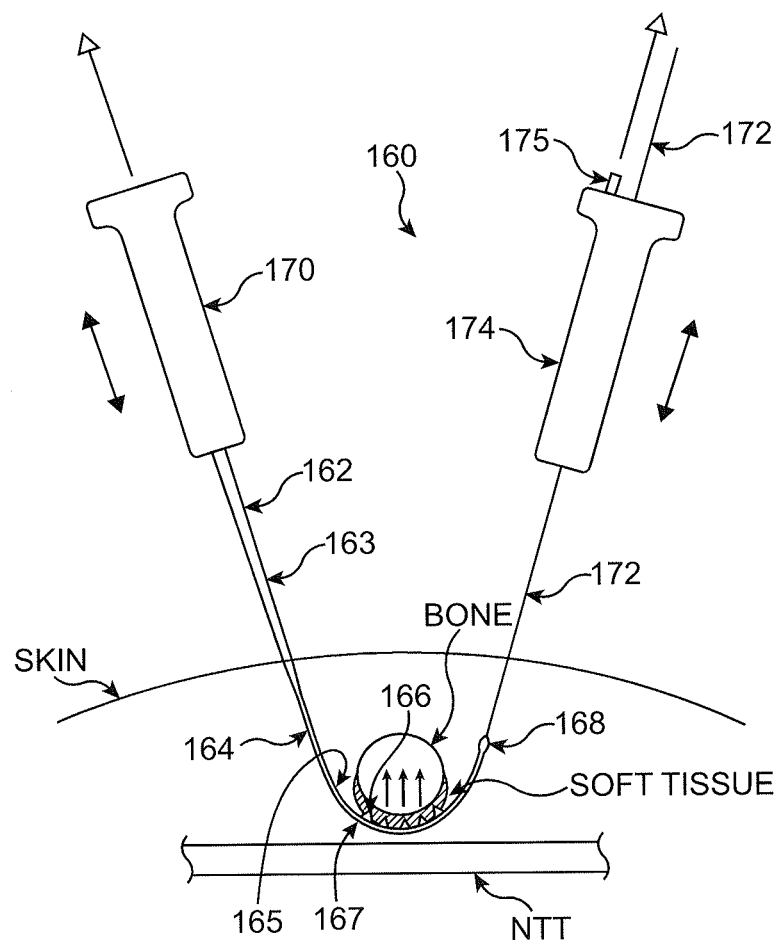
FIG. 23 is a side view of a tissue modification device in a position for performing a tissue modification procedure, showing a generic bone, soft tissue and non-target tissue, according to one embodiment of the present invention.

With reference now to FIG. 23, in another alternative embodiment, a tissue modification device 160 may suitably include a proximal handle 170 coupled with an elongate body 162 (or "shaft") having a proximal, rigid shaft portion 163, a distal flexible portion 164 having a first major surface 165 and an opposed second major surface 167, and multiple substantially in-line, substantially vertical blades 166 disposed laterally across first major surface 165. Second major surface 167 may be atraumatic, to inhibit injury to non-target tissues NTT. A guidewire coupler 168 may be formed in (or attached to) flexible portion 164 at or near its distal end, for coupling with a guidewire 172, which in turn may be coupled with a guidewire handle 174 (or "distal handle"), which may include a tightening lever 175 for tightening handle 174 around guidewire 172. In one embodiment, device 160 may have many of the characteristics and be used in much the same way as embodiments described above, such as device 10 of FIG. 2A. The number, height, length, configuration and placement of blades 166, however, may confer unique tissue cutting/removal characteristics to device 160.

In FIG. 23, device 160 is shown passing into a patient, along a curved path between a generic soft tissue/bone combination and nearby non-target tissue NTT, and back out of the patient. In one embodiment, device 160 may be passed into a patient, through an intervertebral space of the patient's spine (between ligamentum flavum and neural/neurovascular tissue), and back out of the patient, as described in detail above with reference to alternative embodiments. Once device 160 is in place for modifying a target tissue, such as soft tissue and/or bone, handles 170, 174 may be pulled (hollow-tipped arrows) to apply force and thus urge blades 166 into soft tissue (single-headed, solid-tipped arrows). Device 160 may then be reciprocated (double-headed, solid-tipped arrows), while maintaining some or all of the pulling force, to remove or otherwise modify the target soft tissue and/or bone. As mentioned previously, before reciprocating device 160 to remove tissue, in some embodiments the device may be used to stimulate nearby nerve tissue, such as with an electrode coupled with second major surface 167 and/or first major surface 167. Such nerve stimulation may help confirm that device 160 has been placed in a desired location for treatment and may be monitored using electromyography (EMG), visual observation of muscle twitch and/or the like. Second major surface 167 may be made atraumatic in a number of different ways, such as but not limited to forming second major surface 167 with an atraumatic material, smoothing surface 167 during the manufacturing process, coupling an atraumatic cover with surface 167 and/or coating surface 167 with a lubricious coating.

In various embodiments, device 160 may be optimized for removal of soft tissue (such as ligamentum flavum or other ligamentous tissue), bone or a combination of both. Such optimization, for example, may be achieved with various heights, lengths, edge types, numbers and/or placement of blades 166. In some embodiments, it may be possible to remove both soft tissue and bone with device 160, such as by continuing to reciprocate device 160 after soft tissue has been removed and/or by using different amounts of pulling force to remove different types of tissue. For example, in one embodiment, if a surgeon only desires to remove soft tissue, he/she may apply a first amount of pulling force. If, instead, the user desires to remove only bone tissue, it may be possible to apply sufficient force to cut immediately through ligament and address bone. In other embodiments, a user may apply a first amount of tension to device 160 to remove soft tissue and a second amount of tension to remove bone, within the same procedure. For example, it typically requires approximately 30,000 psi of force to cut cortical bone. Thus, in embodiments where it is desired to cut bone, at least some of blades 166 may have bone-cutting tips. In such an embodiment, first major surface 165, when bending over a bone surface, may have an active region with blades 166 that can be urged into soft tissue (such as ligament), and manual tension forces applied to device 160 divided by a combined surface area of the bone cutting tips of blades 166 within the active region may be at least 30,000 psi. In an alternative embodiment, at least some of blades 16 may have bone-protecting ends, and manual tension forces applied to device 160 divided by a combined surface area of the bone-protecting ends of blades 166 within the active region may be less than 30,000 psi. Such an embodiment may facilitate removal of soft tissue, if blades 166 ride or "skate" over the bone and are thus focused on soft tissue removal.

Referring to FIG. 24, in one embodiment a tissue modification device 180 may include a proximal handle 189 coupled with one end of an elongate body 182, which includes a proximal rigid shaft portion 183 and a distal flexible portion 184. Multiple substantially vertical, substantially in-line blades 186, 186' may be disposed on a first major surface 185 of flexible portion 184, while a second major surface 187 approximately opposite first major surface 185 is substantially atraumatic to inhibit damage to non-target tissues during a tissue modification procedure. (Again, by "substantially in-line," it is meant that a side of each blade is aligned at an angle of between about 0 degrees and about 45 degrees relative to the longitudinal axis of the elongate body. By "substantially vertical," it is meant that each blade forms an angle with the first surface of the elongate body of between about 45 degrees and about 90 degrees.) Flexible portion 184 may also include a guidewire coupler 188 at its distal end.

In various embodiments, a number of which are described further below, any suitable combination of blades 186, 186' may be included on a given tissue modification device. For example, device 180 includes four pointed-tip blades 186 and two flat-top blades 186' of various heights and lengths. Various blades may be configured to perform one or more of a number of functions. For example, pointed-tip blades 186 may be ideal for removing bone, while flat-top blades 186' may work best at removing soft tissue and riding along a bone surface, for example to help steer or guide device 180. In some embodiments, all blades on a device may be configured for optimal soft tissue cutting, such as cutting of ligamentum flavum tissue in the spine, while in other embodiments all blades may be configured for optimal bone cutting, such as vertebral bone. Other alternative embodiments may include a combination of blade shapes and configurations to provide multiple different types of cutting. Further discussion of blades combinations and configurations follows below.

With reference now to FIG. 25, an alternative embodiment of a tissue modification device 190 may include an elongate body having a longitudinal axis 191, a rigid shaft portion 193 and a flexible portion 194. Flexible portion 194 may have a lateral axis 195 and may include a guidewire coupler 198 at or near it distal end. In some embodiments, multiple blades 196, 196' may be disposed laterally across a first major surface 192 of flexible portion 194, with each set of two blades 196, 196' extending from a base 197 coupled with surface 192. The embodiment shown includes pointed-tip blades 196 and flat-top blades 196'. In the embodiment shown, and as described in further detail below in relation to an alternative embodiment, some or all blades 196' may be angled, relative to elongate body longitudinal axis 191. Angling blades 196' may cause or facilitate lateral movement of device 190 along a target tissue as device 190 is reciprocated back and forth to modify the tissue, thus providing for wider or more complete tissue removal.

Figure 26:
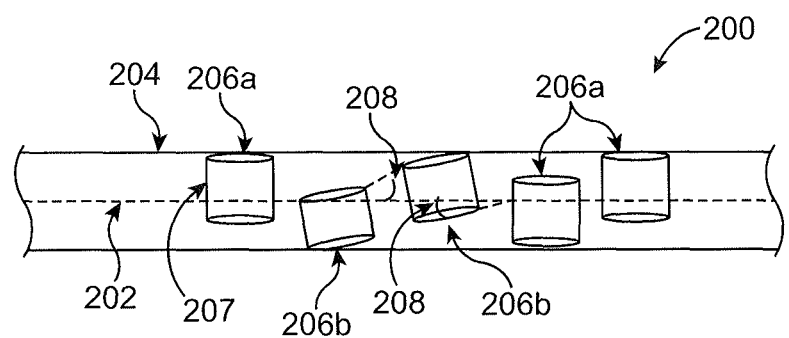
FIG. 26 is a top view of a flexible portion of a tissue modification device with vertically oriented blades, according to one embodiment of the present invention.

Referring to FIG. 26, a flexible portion 204 of an alternative embodiment of a tissue modification device 200 is shown in top view. In this embodiment, flexible portion 204 has a longitudinal axis 202, and multiple sets of blades 206, each set of two blades extending from an associated base 207, coupled with a first surface of flexible portion 204. The sets of blades 206 may be distributed axially along longitudinal axis 202 and may also be distributed laterally across the first major surface. In the embodiment shown, three blades 206a are aligned such that their sides are approximately in line with longitudinal axis 202, while two blades 206b are angled, such that each side forms an angle 208 with longitudinal axis 202. Again, such angled blades 206b may facilitate lateral movement or "steering" of device 200 along a target tissue such as soft tissue and/or bone. In various embodiments, all blades 206 may form an angle of about 0 degrees relative to longitudinal axis 202 (as with blades 206a), all blades may be angled (as with blades 206b), or device 200 may include a combination of angled and non-angled blades. In some embodiments, each blade side may form an angle of between about 0 degrees and about 45 degrees with longitudinal axis 202 of flexible portion 204. As mentioned previously, such blades 206 may be referred to as being "substantially in-line." In a more preferred embodiment, each blade side may form an angle of between about 0 degrees and about 30 degrees relative to longitudinal axis 202. In various alternative embodiments, any number or combination of blades, having any combination of angles, positions on flexible portion 204 or the like may be used.

In various embodiments, blades may be distributed in any of a number of suitable distances and configurations along the first major surface of flexible portion 204. For example, any number of blades 206 may be used in various embodiments, such as but not limited to between two and eight sets of two blades 206 each. In some embodiments, blades 206 are distributed axially along flexible portion 204 at distances selected to confer a desired amount of flexibility to flexible portion 204. Increased space between the sets of blades, for example, may increase the flexibility of flexible portions 204, while placing the sets of blades closer together along longitudinal axis 202 may decrease flexibility of flexible portion 204.

Figure 27A:
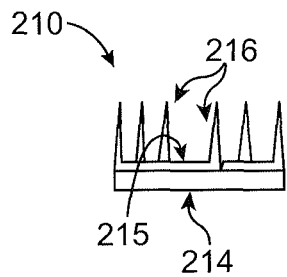
FIGS. 27A-27D are end-on views of flexible portions of various tissue modification devices with vertically oriented blades, according to various alternative embodiments of the present invention.

Referring now to FIG. 27A, one embodiment of a tissue modification device 210 is shown in end-on view at the location of a flexible portion 214 with multiple blades 216 coupled with one side. Each set of two blades 216, in this embodiment, extends from a base 215, and each base 215 is coupled with flexible portion 214. As seen in this figure, in some embodiments some or all blades 216 may be laterally offset, relative to one another, along flexible portion 214. Blades 216 of device 210 are substantially vertical, relative to the surface of flexible portion 214 to which they are attached, and they are also aligned at approximately a 0 degree angle relative to the longitudinal axis of flexible body 214. In device 210, blades form approximately a 90 degree angle with flexible body 214 and approximately a 0 degree angle with the longitudinal axis of flexible body 214.

Figure 27B:
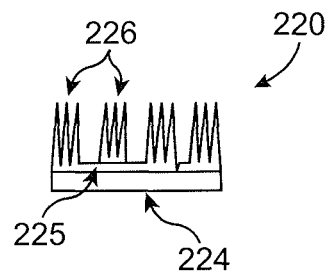

FIG. 27B shows an alternative embodiment of a tissue modification device 220, again in end-on view, where rows of closely spaced blades 226 are attached together on flexible portion 224, analogous to the way sharks' teeth are aligned in rows in a shark's mouth. In this embodiment, sets of six blades 226 (three on each side) extend from one base 225, and each base 225 is coupled with flexible portion 224.

Figure 27C:
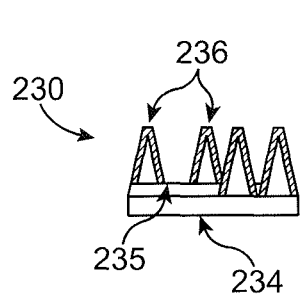

FIG. 27C shows an alternative embodiment of a tissue modification device 230 with four, flat-top blades 236 aligned at an angle relative to the longitudinal axis of flexible portion 234. In this embodiment, each set of two blades 236 extends from an associated base 235.

Figure 27D:
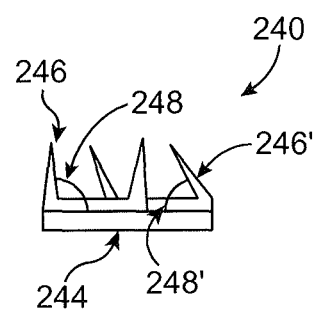

FIG. 27D shows another alternative embodiment of a tissue modification device 240, including two blades 246 that form an approximately 90 degree angle 248 with a first major surface of a flexible portion 244 and two blades 246' that form a more acute angle 248' with the first major surface. In various embodiments, the sides of each blade may form an angle with the flexible portion of between about 90 degrees and about 45 degrees, or more preferably between about 90 degrees and about 60 degrees. These angles 248, 248' may be referred to as "tilt," and in any given embodiment, all blades may be tilted (i.e., all form an angle of less than 90 degrees with the surface), no blades may be tilted (i.e., all form an angle of about 90 degrees with the surface), or some blades may be tilted and others may not, as in FIG. 27D.

Figure 28:
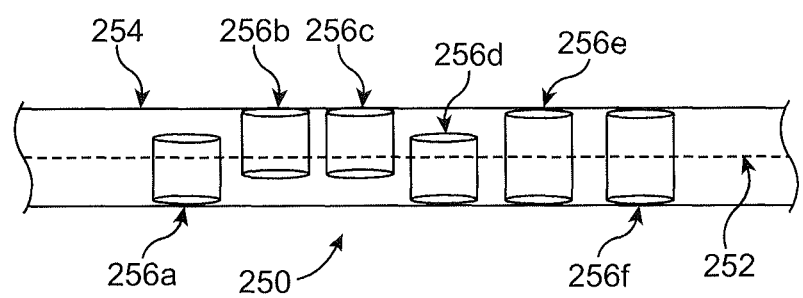
FIG. 28 is a top view of a flexible portion of a tissue modification device with vertically oriented blades, according to an alternative embodiment of the present invention.

Referring now to FIG. 28, as mentioned previously, in some embodiments, a tissue modification device 250 may have a flexible portion 254 including multiple blades 256, some of which may be laterally offset relative to one another and others of which may lie along the same line relative to one another. For example, device 250 includes multiple blades 256, all aligned at approximately 0 degrees relative to a longitudinal axis 252 of flexible portion 254. Blades 256a and 256d lie along the same line, relative to each other, as do blades 256b and 256c. Obviously, blades 256a and 256d are offset, relative to blades 256b and 256c. Blades 256e and 256f lie along the same line relative to one another and are placed close to opposite edges of flexible portion 254. In various embodiments, any combination of lateral placement of blades 256 along device 250 may be used. Offsetting blades 256 relative to one another may facilitate cutting or shredding of soft tissue, for example.

In some embodiments, blades 256 may be shaped and/or axially spaced to facilitate or enhance the collection of cut tissue between blades 256. (By "axially spaced," it is meant the longitudinal spacing along longitudinal axis 252.) In some embodiments, axial spacing of blades 256 may also be optimized to provide a desired flexibility to flexible portion 254.

Figure 29A:
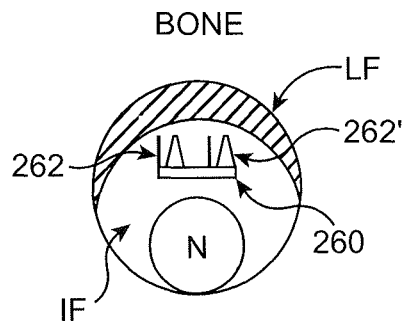
FIGS. 29A-29E are end-on views of a flexible portion of a tissue modification device with vertically oriented blades, demonstrating a method for moving the device back and forth laterally in an intervertebral foramen, according to one embodiment of the present invention.

With reference now to FIGS. 29A-29E, a method according to one embodiment is demonstrated for removing tissue using a tissue modification device 260. FIG. 29A is an end-on, diagrammatic representation of an intervertebral foramen IF, showing vertebral bone, ligamentum flavum LF and nerve root N, with device 260 passing through the foramen IF between nerve root N and ligamentum flavum LF. Device 260 may have some blades 262 vertically oriented and at approximately a 0 degree angle relative to the longitudinal axis of device 260, while other blades 262' may be angled, relative to the longitudinal axis.

Figure 29B:
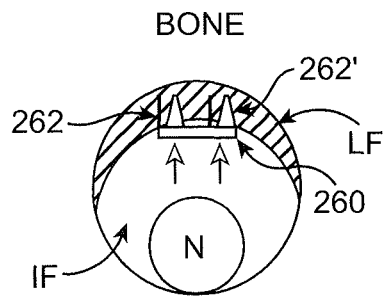

In FIG. 29B, device 260 has been pulled upward (hollow-tipped arrows) to urge blades 262, 262' into ligamentum flavum LF so that at least one of blades 262, 262' contacts vertebral bone. In some embodiments, some or all of blades 262, 262' may have a height approximately equal to or greater than a thickness of an average ligamentum flavum LF.

Figure 29C:
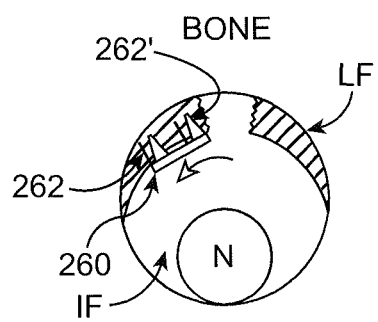

Referring to FIG. 29C, when device 260 is reciprocated back and forth along its longitudinal axis, ligamentum flavum LF tissue is removed in one area of the intervertebral foramen IF. As device 260 is reciprocated, angled blades 262' may steer or guide device 260 laterally in the intervertebral foramen IF (hollow-tipped arrow). In some embodiments, for example, device 260 may steer to one side when the device is pulled in one direction and steer to the other side when the device is pulled in the opposite direction.

Figure 29D:
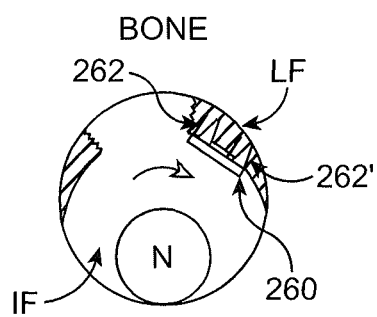

In FIG. 29D, device 260 has moved toward the opposite lateral side of the intervertebral foramen IF (hollow-tipped arrow) to remove additional ligamentum flavum LF tissue. In some embodiments, any or all blades 262, 262' of device 260 may have flat tops, which may help blades 262, 262' to slide or "skate" across the surface of bone as device 260 is reciprocated to cut through soft tissue. This sliding or skating motion may also help device 260 move from side to side within the intervertebral foramen IF.

Figure 29E:
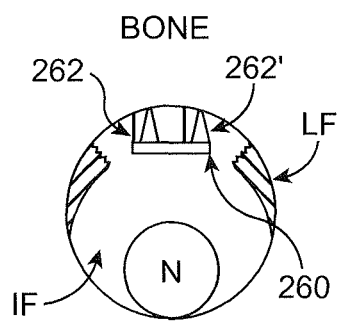
Figure 30:
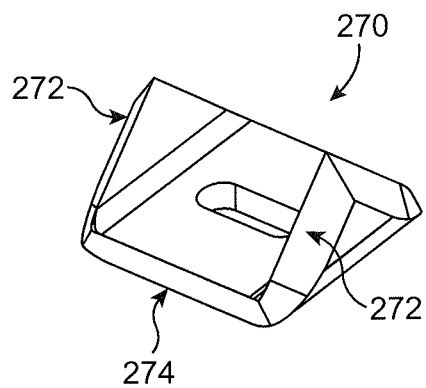
FIG. 30 is a perspective view of a double-blade member for attachment to a flexible portion of a tissue modification device, according to one embodiment of the present invention.

In FIG. 29E, much of the ligamentum flavum LF has been removed, and blades 262, 262' are in a position to treat bone. In some cases, a physician may choose to continue using device 260 to remove bone, while in other cases a physician may wish to remove mostly or exclusively ligamentum flavum LF tissue. In various embodiments, the physician may determine when a desired amount of soft tissue and/or bone is removed by using tactile feedback from device 260, by removing device 260 to examine tissue trapped in device 260, by radiographic visualization such as fluoroscopy, by use of one or more sizing probes or other instruments to gauge the size of the intervertebral foramen IF, or any combination of such methods.

When a desired amount of tissue has been removed, device 260 may be removed from the patient to complete the procedure. As mentioned, in some embodiments, device 260 may be used to remove only ligamentum flavum LF tissue and then removed from the patient to end the procedure. In alternative embodiments, device 260 (or a differently configured device) may be used to remove both soft tissue and bone. In yet another alternative embodiment, a first device (for example, device 260) may be used to remove ligamentum flavum LF tissue, the first device may be removed from the patient, and a second device may be inserted and used to remove bone. Thus, in some embodiments, two different devices may be used in one procedure, with one device optimized for soft tissue removal and another device optimized for bone removal.

With reference now to FIGS. 30-33, various embodiments of blade structures are shown. For example, in an embodiment as in FIG. 30, a blade structure 270 may include two blades 272 extending substantially vertically from a base 274. In some embodiments, each set of two blades 272 and their associated base 274 may be made from one piece of material, with each blade 272 bending upward from base 274. Base 274 may provide a surface for attaching blades 272 to one side of a tissue modification device, such as my welding, attaching via adhesive and/or the like. In one embodiment, blades 272 may have beveled cutting edges and pointed tips, as shown, although any of a number of other blade configurations may alternatively be used.

Figure 31:
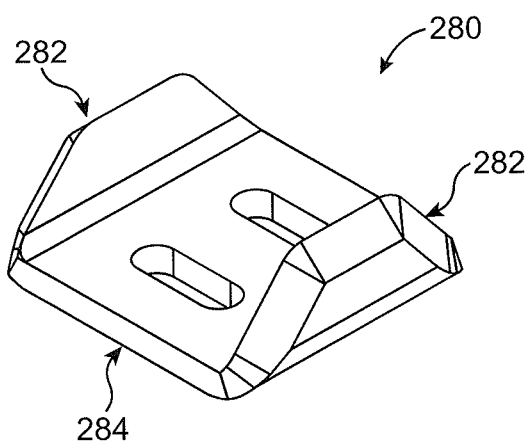
FIG. 31 is a perspective view of a double-blade member for attachment to a flexible portion of a tissue modification device, according to an alternative embodiment of the present invention.

In an alternative embodiment, as in FIG. 31, a blade structure 280 may again include two blades 282 extending substantially vertically from a base 284. In this embodiment, blades 282 have beveled edges and a flat, beveled top.

Figure 32:
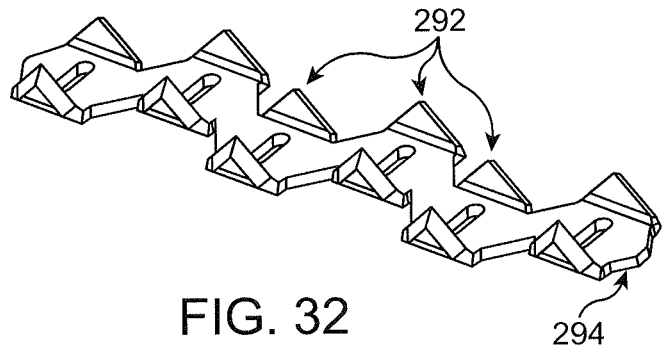
FIG. 32 is a perspective view of a twelve-blade member for attachment to a flexible portion of a tissue modification device, according to an alternative embodiment of the present invention.

In another alternative embodiment, as in FIG. 32, a blade structure 290 may include any number of blades 292 coupled with a base 294. In this embodiment, twelve blades 292 are coupled with base 294, and base 294 has a back-and-forth (or "zig-zag") configuration.

Figure 33:
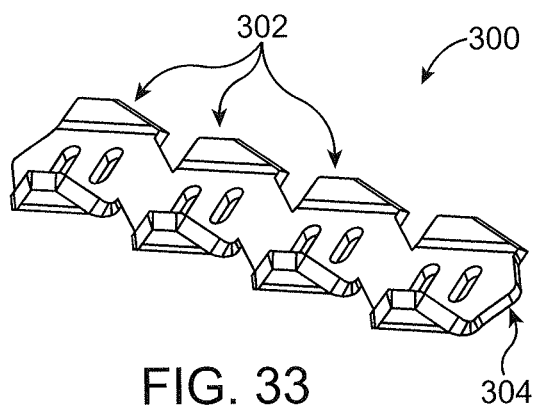
FIG. 33 is a perspective view of a eight-blade member for attachment to a flexible portion of a tissue modification device, according to an alternative embodiment of the present invention.

In another alternative embodiment, as in FIG. 33, a blade structure 300 may include eight, flat-top blades 302 (or any other suitable number) coupled with a base 304 having a diagonal configuration. When base 304 is attached to a surface of a tissue modification device, blades 302 may be angled and/or laterally offset due to the diagonal configuration of base 304.

Figure 34:
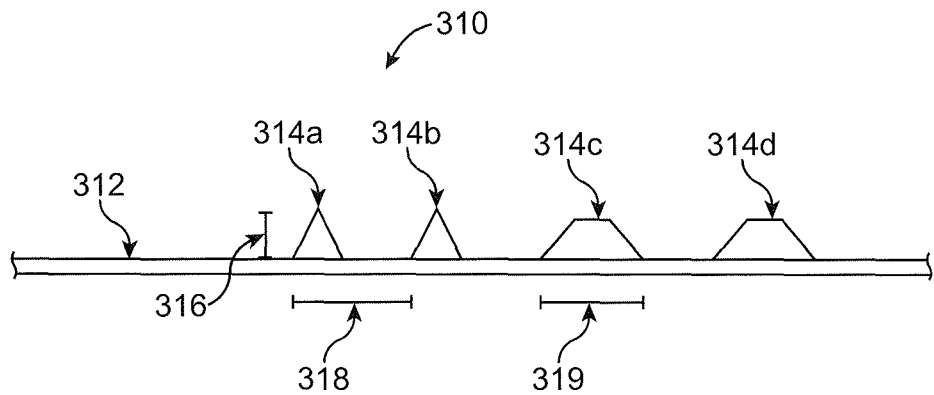
FIG. 34 is a side view of a flexible portion of a tissue modification device with vertically oriented blades, according to one embodiment of the present invention.

Referring now to FIG. 34, one embodiment of a tissue modification device 310 may include an elongate body flexible portion 312 and multiple blades 314 attached to one side of flexible portion 312 such that each blade 314 has a height 316 and a length 319, and such that a distance between two blades 314 defines a pitch 318. As mentioned previously, in various embodiments, blades 314 may have any of a number of shapes, such as pointed-tip 314a, 314b and flat-top 314c, 314d. Each blade 314 may also have a height 316, which may be defined as a distance between of first end of the blade 314, which is coupled with a first surface of flexible portion 312, and a second, cantilevered end of the blade 314. In some embodiments, for example, blades 314 have each have a height ranging from about about 0.5 mm to about 2.0 mm. In some embodiments, two or more blades may have different heights relative to one another. In one embodiment, for example, one or more sets of blades 314 may have a height optimized for addressing bone and one or more other sets of blades 314 may have a height optimized for addressing soft tissue. In one embodiment, shorter blades 314 may be positioned more distally on flexible portion 312, relative to higher blades 314 positioned more proximally. This placement of blades 314 may facilitate entry of device 310 into a tight anatomical location on a patient or around a tight corner.

Length 319 of each blade 314 may be defined as a distance between two blade edges. In various embodiments, blades 314 may have any suitable lengths, and a variety of blade lengths may be used in the same embodiment. Blades 314 may also have a pitch 318, defined as a distance from the beginning of an edge of one blade 314a to the beginning of an edge of a next adjacent blade 314b along device 310. In some embodiments, for example, pitch 318 may range from about 0.5 mm to about 4.0 mm. In various embodiments, any suitable combination of blade shapes, heights 316, lengths 319 and pitches 318 may be used.

Figure 35:
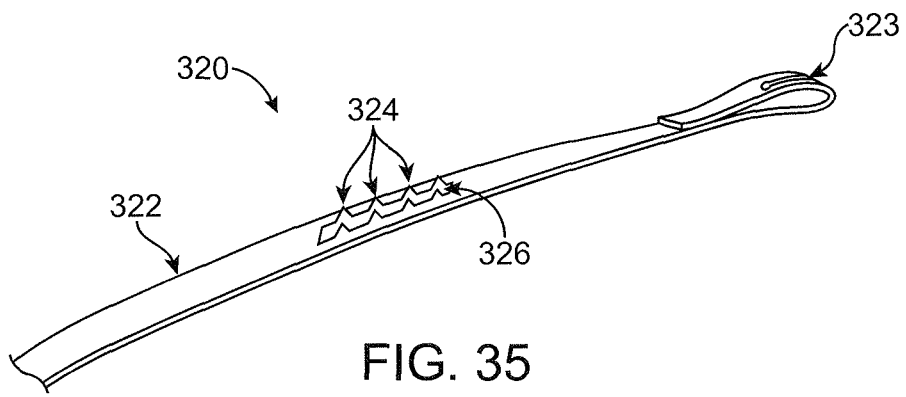
FIG. 35 is a perspective view of a flexible portion of a tissue modification device with vertically oriented blades, according to an alternative embodiment of the present invention.

With reference now to FIG. 35, in another embodiment, a tissue modification device 320 may include multiple blades 324 formed directly out of a flexible portion 322, thus creating an opening 326 in flexible portion 322. For example, blades 324 may be cut and bent out of flexible portion 322. Flexible portion 322 may also include a guidewire coupler 323. In this embodiment, flexible portion 322, blades 324 and guidewire coupler 232 are formed from one piece of material.

Figure 36:
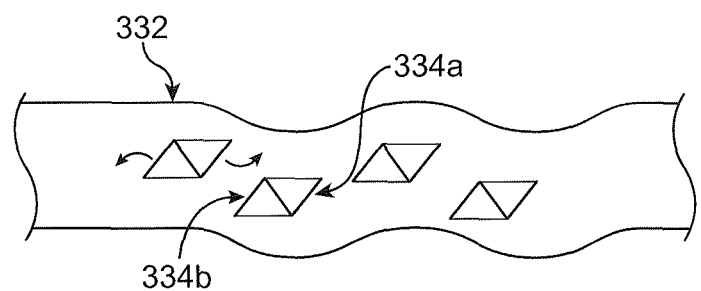
FIG. 36 is a top view of a flexible portion of a tissue modification device, demonstrating a method for forming vertically oriented blades, according to an alternative embodiment of the present invention.

Referring to FIG. 36, in another alternative embodiment, multiple substantially vertical, substantially in-line blades 334 may be formed in a flexible portion 332 of a tissue modification device by cutting multiple flaps in flexible portion 332 and pulling them up to form blades 334 (curved, hollow-tipped arrows). In some embodiments, flexible portion 332 may be curved.

Referring now to FIGS. 37-54, a number of different embodiments of blades, which may be included in various embodiments of tissue modification devices, are shown. This is not meant to be an all-inclusive list, but instead is provided for exemplary purposes. Thus, other blades shapes and configurations not shown in FIGS. 37-54 may also be used in various embodiments of tissue modification devices.

The blade embodiments shown and described below generally have more than one cutting edge, and generally each edge of each blade is a cutting edge. In various alternative embodiments, however, a blade may have multiple edges, but not all the edges need be cutting edges. For example, in some embodiments a blade may have a cutting edge on one side and a dull edge on an opposite side, thus acting as a one-direction cutting blade. In another embodiment, a blade may have a front edge, a back edge and a top edge, and only the front and back edges might be cutting edges, with the top edge being dull, for example to facilitate the blade's riding along a bone surface. Generally, any edge of a blade described below may be, in alternative embodiments, a cutting edge or a non-cutting edge. Cutting edges, generally, may have any of a number of different configurations, such as beveled, pointed, serrated, saw-toothed and the like. Non-cutting edges may also have any of a number of different configurations, such as squared, rounded, notched or the like.

Figure 37:
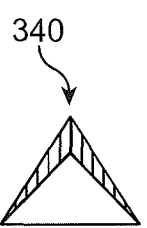
FIGS. 37-54 are side views of various configurations of blades for use with tissue modification devices, according to various alternative embodiments of the present invention.
Figure 38:
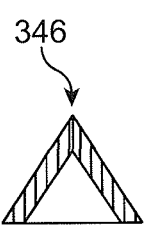
Figure 39:
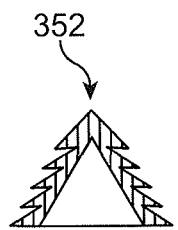
Figure 40:
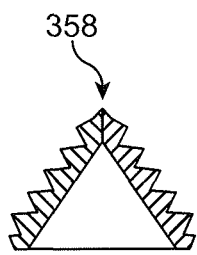

The blades of FIGS. 37-40 are all generally triangle-shaped. FIG. 37 shows a triangle-shaped, pointed-tip blade 340 with tapered cutting edges. FIG. 38 shows a triangle-shaped, pointed-tip blade 346 with straight cutting edges. FIG. 39 shows a triangle-shaped, pointed-tip blade 352 with downward-facing barbs on two cutting edges. FIG. 40 shows a triangle-shaped, pointed-tip blade 358 with saw-tooth cutting edges.

Figure 41:
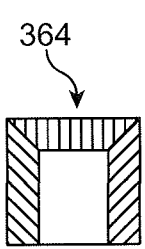
Figure 42:
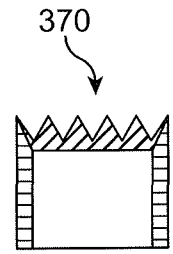

FIGS. 41 and 42 show square-shaped blades. FIG. 41 shows a square-shaped blade 364 with a flat-top cutting edge and straight vertical cutting edges. FIG. 42 shows a square-shaped blade 370 with straight vertical cutting edges and a crown-shaped (or serrated or saw-tooth) upper horizontal cutting edge.

Figure 43:
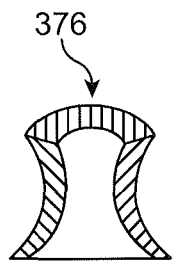
Figure 44:
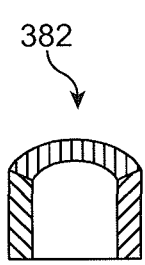
Figure 45:
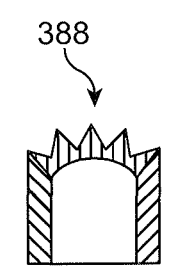

The blades in FIGS. 43-45 all have convex-shaped upper cutting edges. In FIG. 43, blade 376 has a convex upper cutting edge and concave lateral cutting edges. In FIG. 44, blade 382 has a convex upper cutting edge and straight lateral (or vertical) cutting edges. In FIG. 45, blade 388 has a convex, crown-shaped (or serrated or saw-tooth) upper cutting edge and straight lateral cutting edges.

Figure 46:
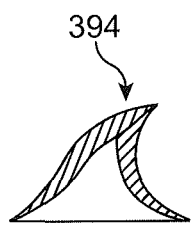
Figure 47:
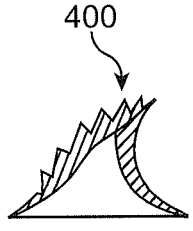
Figure 48:
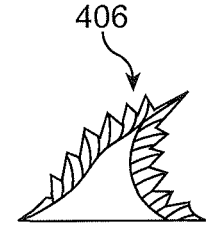

The blades in FIGS. 46-48 are all wave-shaped. The blade 394 of FIG. 46 has a wave shape and two smooth cutting edges. The blade 400 of FIG. 47 has a wave shape, one smooth cutting edge and one saw-tooth (or serrated) cutting edge. The blade 406 of FIG. 48 has a wave shape and two saw-tooth cutting edges.

Figure 49:
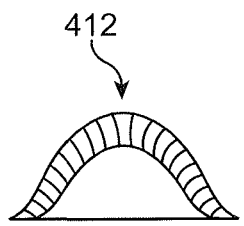
Figure 50:
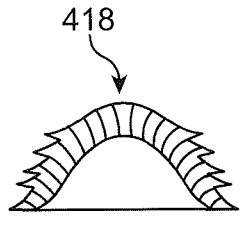
Figure 51:
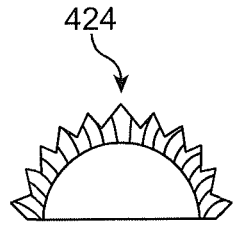

FIGS. 49-51 all show rounded blades. In FIG. 49, blade 412 is rounded with a smooth cutting edge. In FIG. 50, blade 418 is rounded with downward facing barbs along a portion of its cutting edges. In FIG. 51, blade 424 is rounded with a saw-tooth (or serrated) cutting edge.

Figure 52:
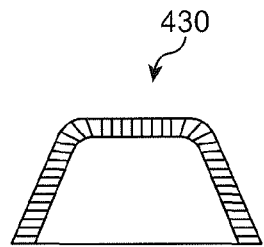
Figure 53:
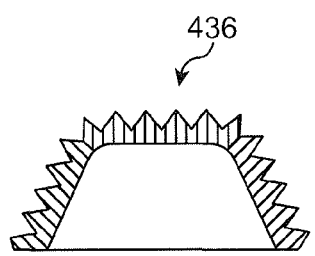
Figure 54:
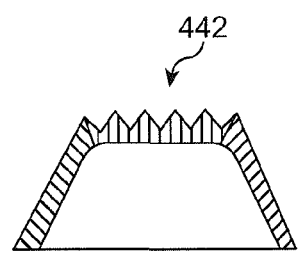

The blades of FIGS. 52-54 are all trapezoidal in shape. In FIG. 52, blade 430 has a trapezoidal shape and straight/smooth cutting edges. In FIG. 53, blade 436 has a trapezoidal shape and saw-tooth (or serrated) cutting edges. In FIG. 54, blade 442 has a trapezoidal shape and straight lateral cutting edges with a saw-tooth (or serrated) upper cutting edge. Again, the foregoing examples are provided for exemplary purposes, and in various embodiments, tissue modification devices may include any alternative blade shapes and configurations.

Figure 55:
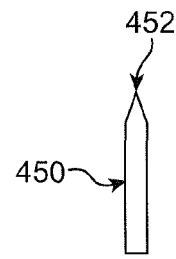
FIGS. 55-60 are cross-sectional views of various configurations of blades for use with tissue modification devices, according to various alternative embodiments of the present invention.
Figure 56:
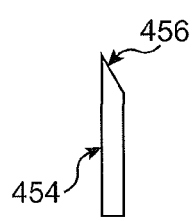
Figure 57:
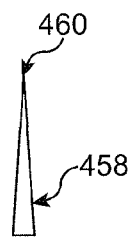
Figure 58:
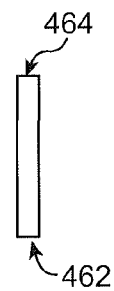

FIGS. 55-60 are cross-sectional views of a number of different blade embodiments, looking from an end-on perspective. According to various embodiments, blades may have any of a number of different upper cutting surfaces, and FIGS. 55-60 illustrate several examples of such surfaces. In FIG. 55, for example, blade 450 includes an upper cutting edge having a double-bevel configuration. The blade 454 in FIG. 56 has a single-bevel upper cutting edge 456. In FIG. 57, blade 458 has a tapered shape that ends in upper cutting edge 460.

Figure 59:
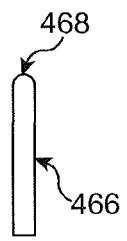
Figure 60:
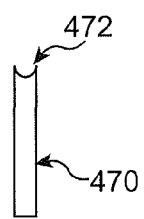

In some embodiments, a blade may have an upper surface that is not sharp or pointed. Such an upper surface may help such a blade to slide or skate off of a bony surface, thus facilitating steering of a tissue modification device. For example, in FIG. 58, blade 462 has a flat upper surface 464. In FIG. 59, blade 466 has a rounded (or convex) upper surface 468. In FIG. 60, blade 470 has a concave upper surface 472. Again, any other suitable blade shape may be used in various alternative embodiments.

In various embodiments, any given flexible tissue modification device may act on tissue in a number of different ways, such as by cutting, ablating, dissecting, repairing, reducing blood flow in, shrinking, shaving, burring, biting, remodeling, biopsying, debriding, lysing, debulking, sanding, filing, planing, heating, cooling, vaporizing, delivering a drug to, and/or retracting target tissue. For example, many of the devices described above may also optionally be loaded with a drug, bone wax, gel foam, or the like, which may be deposited during a tissue modification procedure. Any suitable drug may be delivered via the devices in various embodiments, such as but not limited to thrombin, NSAID, local anesthetic or opioid. In some embodiments, devices may also deliver an implant, such as a stent-like implant for maintaining patency of decompressed intervertebral foramen, a rivet, staple or similar device for retracting ligamentum flavum tissue, a tissue dressing, or the like. In some embodiments, devices may cool or freeze tissue for analgesia or to change the tissue's modulus of elasticity to facilitate tissue modification. Some embodiments of devices may also include a visualization and/or diagnostic component, such as an ultrasound, MRI, reflectance spectroscopy, fiber optic, endoscope, charge-coupled device (CCD), complementary metal-oxide semiconductor (CMOS) or other device.

Any of the devices described herein may also optionally include one or more components for neural identification and/or localization. For example, in some embodiments, a flexible tissue modification device may include one or more nerve stimulation electrodes on a backside or underside of the device (i.e., a side designed to be atraumatic and face non-target tissue). The electrode(s) may be used to confirm that the atraumatic side of the device is in contact with non-target neural tissue, thus also confirming that the tissue modification members of the device are facing target tissue. In some embodiments, the devices may also include one or more electrodes on an upper surface, at or near the tissue modification members, to further confirm a desired placement of the device. For further description of such neural localization devices and methods, reference may be made to U.S. patent application Ser. No. 11/457,416 (now U.S. Pat. No. 7,578, 819), which was previously incorporated by reference.

In various alternative embodiments, any of the tissue modification devices and method described above may be used in combination with one or more vertebral distraction devices. In one embodiment, for example, an interspinous implant such as the X STOP® implant (offered by St. Francis Medical Technologies, Inc., Alameda, Calif., www.sfmt.com) may be inserted between adjacent vertebrae, and then access devices and/or tissue removal devices described herein may be used to remove or otherwise modify spinal tissue. Such an implant may be inserted and left in place after a procedure, while in alternative embodiments a distraction device may be used only during a tissue removal procedure. Various embodiments and aspects of such distraction/tissue removal combinations are described in greater detail in U.S. Provisional Patent Application No. 60/884,37, titled "Spinal Stenosis Treatment Methods and Apparatus," filed Jan. 10, 2007, the full disclosure of which is herein incorporated by reference in its entirety.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

What is claimed is:

1. A method for modifying a target bone of a bone joint in a patient, the method comprising:
    advancing a guidewire into the body and adjacent to the target bone of a bone joint so that the guidewire passes along a path through the patient where the proximal end of the guidewire extends from a first position outside of the patient's body and the distal end of the guidewire extends from a second position outside of the patient;
    coupling the proximal end of the guidewire to a tissue modification device outside of the body after advancing the guidewire into the body, wherein the tissue modification device is for modifying bone tissue and comprises an elongate flexible body having a tissue-modifying active region;
    pulling the tissue modification device behind the guidewire along the path to position the active region of the tissue modification device adjacent to the target bone of the bone joint, wherein the proximal end of the guidewire remains within the body;
    urging the active region of the tissue modification device against the target bone by manually reciprocating the elongate body axially along the path while a portion of the guidewire remains within the body; and
        wherein coupling the proximal end of the guidewire comprises coupling the proximal end of the guidewire to a tapered distal end region of the tissue modification device.

2. The method of claim 1, wherein the target bone comprises spine.

3. The method of claim 1, wherein the target bone comprises hip.

4. The method of claim 1, wherein the target bone comprises bone of a sacro-iliac joint.

5. The method of claim 1, wherein urging comprises reciprocally applying pulling force at or near opposite ends of the elongate body.

6. The method of claim 1, further comprising reciprocating the elongate body to remove a portion of the target bone.

7. The method of claim 1, wherein pulling the tissue modification device comprises advancing the elongate body percutaneously into the patient by pulling the device behind the guidewire.

8. The method of claim 1, further comprising inhibiting damage to a non-target tissue with an atraumatic surface of the elongate body configured to contact the non-target tissue when the blades contact target tissue.

9. The method of claim 1, wherein urging the active region comprises reciprocating the elongate body axially along the path by alternately applying a manual pulling force to a handle at a distal end of the guidewire and applying a manual pulling force to a handle a proximal end of the tissue modification device.

10. The method of claim 1, wherein urging the active region comprises reciprocating the elongate body axially along the path by alternately applying a manual pulling force to a handle at a distal end of the guidewire and applying a manual pulling force to a handle a proximal end of the tissue modification device, wherein the distal handle and the proximal handle move in opposite directions relative to the outside of the patient's body such that one handle moves toward the body while the other handle moves away from the body.

11. The method of claim 1, wherein the tissue-modifying active region of the tissue modification device comprises a plurality of blades.

12. The method of claim 1, wherein the tissue-modifying active region of the tissue modification device comprises an abrasive surface.

13. The method of claim 1, wherein urging the active region of the tissue modification device against the target bone comprises abrading the target bone.

14. A method for modifying a target bone of a bone joint in a patient, the method comprising:
    advancing a guidewire into the body and adjacent to the target bone so that the proximal end of the guidewire extends from a first position outside of the patient's body and the distal end of the guidewire extends from a second position outside of the patient;
    coupling the proximal end of the guidewire to a tissue modification device outside of the body after advancing the guidewire into the body, wherein the tissue modification device is for modifying bone and comprises an elongate flexible body having a tissue modifying active region at or near a distal end of the tissue modification device;
    pulling the tissue modification device into the bone joint behind the guidewire to position the active region adjacent the target bone, wherein the proximal end of the guidewire remains within the body;
    abrading the target bone by alternately pulling on the proximal end of the tissue modification device and the guidewire to manually reciprocate and urge the active region against the bone while the proximal end of the guidewire remains within the body; and
    wherein coupling the proximal end of the guidewire comprises coupling the proximal end of the guidewire to a tapered distal end region of the tissue modification device.

15. The method of claim 14, wherein the target bone comprises spine.

16. The method of claim 14, wherein the target bone comprises hip.

17. The method of claim 14, wherein the target bone comprises bone of a sacro-iliac joint.

18. The method of claim 14, wherein pulling the tissue modification device comprises advancing the elongate body percutaneously into the patient by pulling the device behind the guidewire.

19. The method of claim 14, further comprising inhibiting damage to a non-target tissue with an atraumatic surface of the elongate body configured to contact the non-target tissue when the blades contact target tissue.

20. The method of claim 14, wherein abrading the target bone comprises reciprocating the elongate body axially by alternately applying a manual pulling force to a handle at a distal end of the guidewire and applying a manual pulling force to a handle a proximal end of the tissue modification device.

21. The method of claim 14, wherein the active region of the tissue modification device comprises a plurality of blades.

22. The method of claim 14, wherein the active region of the tissue modification device comprises an abrasive surface.

* * * * *